United States Patent
Zweckstetter et al.

(10) Patent No.: US 12,254,963 B2
(45) Date of Patent: Mar. 18, 2025

(54) METHOD FOR DETERMINATION OF THE ANISOTROPIC PARAMETERS FOR THE CONFIGURATION OF ORGANIC MOLECULES EMBEDDED IN ALIGNMENT MEDIA

(71) Applicants: Max-Planck-Gesellschaft zur Förderung der Wissenschaften e.V., Munich (DE); Deutsches Zentrum für Neurodegenerative Erkrankungen, Bonn (DE)

(72) Inventors: Markus Zweckstetter, Göttingen (DE); Nina Alexandra Klama, Göttingen (DE); Alain Ibanez De Opakua Lopez De Abi, Göttingen (DE)

(73) Assignees: MAX-PLACK-GESELLSCHAFT ZUR FORDERUNG DER WISSENSCHAFTEN E.V., Munich (DE); DEUTSCHES ZENTRUM FUR NEURODEGENRATIVE ERKANKUNG, Bonn (DE)

( * ) Notice: Subject to any disclaimer, the term of this patent is extended or adjusted under 35 U.S.C. 154(b) by 422 days.

(21) Appl. No.: 17/793,218

(22) PCT Filed: Jan. 12, 2021

(86) PCT No.: PCT/EP2021/050468
§ 371 (c)(1),
(2) Date: Jul. 15, 2022

(87) PCT Pub. No.: WO2021/144253
PCT Pub. Date: Jul. 22, 2021

(65) Prior Publication Data
US 2023/0067122 A1    Mar. 2, 2023

(30) Foreign Application Priority Data
Jan. 17, 2020   (EP) .................................. 20152457

(51) Int. Cl.
| | | |
|---|---|---|
| G16C 20/20 | (2019.01) | |
| G01N 24/08 | (2006.01) | |
| G16C 20/30 | (2019.01) | |
| G16C 20/50 | (2019.01) | |

(52) U.S. Cl.
CPC .......... *G16C 20/20* (2019.02); *G01N 24/087* (2013.01); *G16C 20/30* (2019.02); *G16C 20/50* (2019.02)

(58) Field of Classification Search
CPC ........ G16C 20/50; G16C 20/30; G16C 20/20; G01R 33/46; G01N 24/087
See application file for complete search history.

(56) References Cited

U.S. PATENT DOCUMENTS

| | | | | |
|---|---|---|---|---|
| 8,374,837 | B2* | 2/2013 | De Winter | G16C 20/30 703/11 |
| 9,317,664 | B2* | 4/2016 | Ahuja | G16B 50/00 |
| 10,684,287 | B1* | 6/2020 | Tang | G01N 33/68 |

FOREIGN PATENT DOCUMENTS

EP    3851840 A1    7/2021

OTHER PUBLICATIONS

Frank, A. et al., "Direct prediction of residual dipolar couplings of small molecules in a stretched gel by stochastic molecular dynamics simulations", Magnetic Resonance in Chemistry vol. 53, 2015.
(Continued)

*Primary Examiner* — An H Do
(74) *Attorney, Agent, or Firm* — WC&F IP

(57) ABSTRACT

A method for determination of molecular parameters for a configuration of a known single organic molecule embedded in an anisotropic environment generated by alignment media, said known single organic molecule comprising particles, is disclosed. The method comprising the steps of: a) Defining a three-dimensional grid that is aligned with the known atomic structure of the alignment medium; b) Placing
(Continued)

the particles of the known single organic molecule on the respective grid points of the three-dimensional grid in relation to at least one assigned atom of the alignment medium; c) Determining the interaction between the particles of the single organic molecule and the alignment medium for a set of orientations and a plurality of configurations of the particles; d) Calculating anisotropic parameters obtainable by measuring with nuclear magnetic resonance (NMR) spectroscopy by use of the determined interactions for each of the plurality of configurations of the organic molecule.

15 Claims, 47 Drawing Sheets

(56) References Cited

OTHER PUBLICATIONS

Schmidts, V., "Perspectives in the application of residual dipolar couplings in the structure elucidation of weakly aligned small molecules", Magnetic Resonance in Chemistry vol. 55, 2016.

Hansmann, S. et al., "Synthesis of Poly-y-S-2 methylbutyl-L-glutamate and Poly-y-S-2-methylbutyl-D-glutamate and Their Use as Enantiodiscriminating Alignment Media in NMR Spectroscopy", Chemistry—A European Journal vol. 23, 2017.

Berlin, K. et al., "Improvement and analysis of computational methods for prediction of residual dipolar couplings", Journal of Magnetic Resonance vol. 201, 2009.

Zweckstetter, M., "NMR: prediction of molecular alignment from structure using the PALES software", Nature Protocols vol. 3 No. 4, 2008.

Ibanez de Opakua, A., "Determination of Complex Small-Molecule Structures Using Molecular Alignment Simulation", Angewantde Chemie International Edition vol. 59, 2020.

Saupe, A. et al., "High-Resolution Nuclear Magnetic Resonance Spectra of Orientated Molecules", Physical Review etters vol. 11 No. 10, 1963.

Tjandra, N. et al., "Direct Measurement of Distances and Angles in Biomolecules by NMR in a Dilute Liquid Crystalline Medium", Science vol. 278, 1997.

Ibanaz de Opakua, A. et al., "Extending the applicability of P3D for structure determination of small molecules", German Center for Neurodegenerative Diseases.

* cited by examiner

RRS

RSS

RSR

RRR

IPC

R(1)R(2)S(3)

| Atom | n | RDC (Hz) |
|---|---|---|
| 1 | 1 | 13.6 |
| 2 | 1 | -5.9 |
| 3 | 1 | 12 |
| 5 | 1 | -4.9 |
| 4 | 2 | -4.3<br>12.6 |
| 7 | 2 | -17<br>2.8 |

Strychnine $R_{(7)}S_{(8)}S_{(12)}R_{(13)}R_{(14)}S_{(16)}$

| Atom | n | RDC (Hz) |
|---|---|---|
| 1 | 1 | -178.9 |
| 2 | 1 | -36.9 |
| 3 | 1 | -69.8 |
| 4 | 1 | -182.4 |
| 8 | 1 | 87.1 |
| 12 | 1 | 146.8 |
| 13 | 1 | 48.9 |
| 14 | 1 | 151.7 |
| 16 | 1 | -49.6 |
| 22 | 1 | -1.1 |

Caulamidine $S_{(10)}S_{(11)}S_{(23)}$

| Atom | n | RDC (Hz) |
|---|---|---|
| 5 | 1 | -163.4 |
| 6 | 1 | 121.3 |
| 8 | 1 | -187.1 |
| 11 | 1 | 185.5 |
| 17 | 1 | -53 |
| 18 | 1 | -283.5 |
| 20 | 1 | -52.2 |

CPDMPPPC

R(2)S(3)R(4)R(5)

| Atom | n | RDC (Hz) |
|---|---|---|
| 2 | 1 | 201.1 |
| 3 | 1 | 59.8 |
| 4 | 1 | 193.6 |
| 5 | 1 | 133.1 |
| 6-7 | 0 | 24.8 |
| 8-10' | 0 | -27.8 |
| 9-10' | 0 | -10 |

Parthenolide $R_{(3)}R_{(4)}S_{(7)}S_{(8)}E_{(5\text{-}6)}$

| Atom | n | RDC (Hz) |
|------|---|----------|
| 4    | 1 | 105.2    |
| 6    | 1 | 50.4     |
| 7    | 1 | 92.5     |
| 8    | 1 | 96.8     |
| 3-14 | 0 | -28.7    |
| 5-15 | 0 | -14.7    |

|  |  | SVD | | 1D | | 3D vdW | | PALES-3D | |
|---|---|---|---|---|---|---|---|---|---|
|  |  | R | $Q_s$ | R | $Q_s$ | R | $Q_s$ | R | $Q_s$ |
| DAHPA | RSR* | - | - | 0.888 ±0.004 | 0.495 ±0.009 | 0.882 ±0.004 | 0.489 ±0.010 | 0.843 ±0.004 | 0.598 ±0.010 |
| | RRR | - | - | 0.721 ±0.006 | 0.883 ±0.015 | 0.619 ±0.006 | 1.386 ±0.024 | 0.726 ±0.006 | 0.862 ±0.014 |
| | SRR | - | - | 0.784 ±0.005 | 0.742 ±0.011 | 0.740 ±0.006 | 0.825 ±0.014 | 0.781 ±0.005 | 0.757 ±0.011 |
| | RRS | - | - | 0.318 ±0.008 | 2.713 ±0.075 | 0.008 ±0.008 | 151.65 ±1064 | 0.268 ±0.008 | 3.345 ±0.104 |
| IPC | RRS* | 0.970 ±0.002 | 0.251 ±0.007 | 0.678 ±0.004 | 1.079 ±0.013 | 0.695 ±0.004 | 1.030 ±0.012 | 0.840 ±0.003 | 0.643 ±0.009 |
| | RSS | 0.923 ±0.002 | 0.420 ±0.007 | 0.666 ±0.004 | 1.142 ±0.014 | 0.709 ±0.004 | 1.007 ±0.012 | 0.763 ±0.004 | 0.857 ±0.011 |
| | RSR | 0.887 ±0.003 | 0.527 ±0.008 | 0.492 ±0.005 | 1.897 ±0.024 | 0.427 ±0.005 | 2.240 ±0.030 | 0.435 ±0.005 | 2.182 ±0.029 |
| | RRR | 0.929 ±0.002 | 0.395 ±0.007 | 0.545 ±0.005 | 1.575 ±0.019 | 0.391 ±0.005 | 2.393 ±0.035 | 0.460 ±0.005 | 1.971 ±0.026 |
| Strychnine | RSSRRS* | 1.000 ±0.001 | 0.014 ±0.007 | 0.638 ±0.009 | 1.217 ±0.029 | 0.628 ±0.009 | 1.244 ±0.029 | 0.883 ±0.005 | 0.538 ±0.015 |
| | RSRSRS | 0.941 ±0.004 | 0.121± 0.013 | 0.555 ±0.009 | 1.494 ±0.033 | 0.523 ±0.009 | 1.624 ±0.038 | 0.663 ±0.007 | 1.130 ±0.023 |
| | RSRSSS | 0.942 ±0.004 | 0.208 ±0.012 | 0.185 ±0.010 | 5.276 ±0.299 | 0.363 ±0.010 | 2.602 ±0.079 | 0.611 ±0.008 | 1.303 ±0.028 |
| | RSRRRS | 0.996 ±0.001 | 0.270 ±0.011 | 0.598 ±0.009 | 1.337 ±0.032 | 0.591 ±0.009 | 1.364 ±0.032 | 0.866 ±0.005 | 0.587 ±0.014 |
| | RSSSRS | 0.988 ±0.002 | 0.252 ±0.011 | 0.620 ±0.008 | 1.262± 0.028 | 0.591 ±0.009 | 1.368 ±0.030 | 0.776 ±0.007 | 0.811 ±0.018 |
| | RSRRSS | 0.903 ±0.005 | 0.359 ±0.014 | 0.334 ±0.010 | 2.920± 0.093 | 0.467 ±0.009 | 2.065 ±0.049 | 0.648 ±0.008 | 1.255 ±0.026 |
| | RSSSSS | 0.909 ±0.005 | 0.367 ±0.014 | 0.426 ±0.009 | 2.237± 0.057 | 0.625 ±0.008 | 1.433 ±0.028 | 0.604 ±0.008 | 1.362 ±0.028 |
| | RSSRSS | 0.859 ±0.006 | 0.087 ±0.016 | 0.486 ±0.009 | 2.000 ±0.046 | 0.634 ±0.008 | 1.482 ±0.028 | 0.626 ±0.008 | 1.367 ±0.028 |
| | SSRSSR | 0.963 ±0.003 | 0.162 ±0.012 | 0.269 ±0.010 | 3.576 ±0.147 | 0.324 ±0.010 | 2.924 ±0.102 | 0.681 ±0.008 | 1.075 ±0.023 |
| | SSSSSR | 0.994 ±0.001 | 0.479 ±0.010 | 0.501 ±0.009 | 1.758 ±0.040 | 0.530 ±0.009 | 1.647 ±0.036 | 0.713 ±0.007 | 1.008 ±0.020 |
| | SSRRSR | 0.982 ±0.002 | 0.465 ±0.011 | 0.637 ±0.008 | 1.278 ±0.025 | 0.625 ±0.008 | 1.336 ±0.027 | 0.803 ±0.006 | 0.798 ±0.016 |
| | SSSRSR | 0.965 ±0.003 | 0.616 ±0.012 | 0.617 ±0.008 | 1.332 ±0.027 | 0.603 ±0.008 | 1.392 ±0.028 | 0.758 ±0.006 | 0.911 ±0.017 |
| | RSRSSR | 0.986 ±0.002 | 0.288 ±0.010 | 0.590 ±0.008 | 1.369 ±0.028 | 0.712 ±0.007 | 1.022 ±0.021 | 0.843 ±0.006 | 0.707 ±0.016 |

Fig. 33 a)

|  |  | SVD | | 1D | | 3D vdW | | PALES-3D | |
|---|---|---|---|---|---|---|---|---|---|
|  |  | R | $Q_s$ | R | $Q_s$ | R | $Q_s$ | R | $Q_s$ |
| Caulamidine | SSS* | 1.000 ±0.001 | 0.018 ±0.006 | 0.971 ±0.002 | 0.240± 0.008 | 0.464 ±0.007 | 2.567 ±0.042 | 0.827 ±0.005 | 0.747 ±0.010 |
|  | SRS | 0.999 ±0.001 | 0.041 ±0.009 | 0.313 ±0.008 | 3.755± 0.117 | -0.132 ±0.008 | 7.082±0.468 | 0.137±0.008 | 7.217 ±0.479 |
|  | SRR | 0.998 ±0.001 | 0.058 ±0.009 | -0.601 ±0.006 | 2.495 ±0.027 | -0.730 ±0.005 | 1.265 ±0.013 | -0.611 ±0.006 | 2.229 ±0.024 |
|  | SSR | 0.938 ±0.003 | 0.352 ±0.009 | -0.300 ±0.008 | 4.384 ±0.111 | -0.587 ±0.007 | 1.695±0.022 | -0.459 ±0.007 | 2.770 ±0.044 |
| CPDMPPPC | RSRR* | - | - | 0.884 ±0.023 | 0.212 ±0.017 | 0.863 ±0.025 | 0.211 ±0.028 | 0.960 ±0.014 | 0.193 ±0.030 |
|  | RSRS | - | - | 0.825 ±0.027 | 0.551 ±0.018 | 0.833 ±0.026 | 0.678 ±0.014 | 0.821±0.026 | 0.600 ±0.016 |
|  | RSSR | - | - | -0.376 ±0.038 | 7.251 ±0.772 | -0.387 ±0.040 | 4.144 ±0.395 | -0.257 ±0.044 | 11.117 ±1.995 |
|  | RSSS | - | - | -0.195 ±0.044 | 5.014 ±1.128 | -0.153 ±0.043 | 4.611 ±1.456 | -0.335 ±0.043 | 3.430 ±0.374 |
|  | RRRR | - | - | 0.890 ±0.023 | 0.951 ±0.108 | 0.930 ±0.018 | 0.291 ±0.066 | 0.860 ±0.025 | 1.001 ±0.115 |
|  | RRRS | - | - | 0.636 ±0.038 | 0.529 ±0.018 | 0.738 ±0.033 | 0.588 ±0.013 | 0.785 ±0.030 | 0.559 ±0.016 |
|  | RRSR | - | - | -0.813 ±0.028 | 1.790 ±0.050 | -0.525 ±0.041 | 2.342 ±0.140 | -0.716 ±0.034 | 1.781 ±0.059 |
|  | RRSS | - | - | -0.976 ±0.011 | 1.388 ±0.014 | -0.868 ±0.020 | 1.327 ±0.018 | -0.305 ±0.042 | 1.966 ±0.199 |

Fig. 33 b)

|  |  | SVD | | 1D | | 3D vdW | | PALES-3D | |
|---|---|---|---|---|---|---|---|---|---|
|  |  | R | Q$_s$ | R | Q$_s$ | R | Q$_s$ | R | Q$_s$ |
| Parthenolide | RRSSE* | - | - | 0.988 ±0.016 | 0.165 ±0.072 | 0.996 ±0.011 | 0.355 ±0.063 | 0.990 ±0.015 | 0.161 ±0.073 |
| | RRSSZ | - | - | 0.177 ±0.090 | 10.14 ±55 | 0.025 ±0.091 | 100.54±4217 | 0.197 ±0.089 | 12.61 ±61 |
| | RRRRE | - | - | -0.043 ±0.088 | 8.104 ±55.475 | 0.142 ±0.087 | 1.692 ±4.715 | 0.121 ±0.087 | 2.034 ±26.182 |
| | RRRRZ | - | - | 0.101 ±0.087 | 2.368 ±47.213 | 0.104 ±0.087 | 2.293 ±12.618 | 0.157 ±0.086 | 1.512 ±11.829 |
| | RSSSE | - | - | -0.637 ±0.066 | 1.580 ±0.087 | -0.576 ±0.071 | 1.933 ±0.157 | -0.402 ±0.082 | 2.035 ±0.272 |
| | RSSSZ | - | - | -0.499 ±0.074 | 1.395 ±0.093 | -0.348 ±0.082 | 1.613 ±0.240 | 0.018 ±0.090 | 12.96 ±115 |
| | RRRSE | - | - | 0.064 ±0.090 | 4.470 ±75.211 | 0.274 ±0.086 | 0.941 ±0.498 | 0.278 ±0.085 | 0.993 ±0.450 |
| | RRRSZ | - | - | 0.916 ±0.036 | 0.580 ±0.043 | 0.753 ±0.057 | 0.406 ±0.048 | 0.479 ±0.076 | 0.569 ±0.264 |
| | RRSRE | - | - | -0.020 ±0.087 | 38.71 ±58 | 0.653 ±0.065 | 5.955 ±1.014 | -0.592 ±0.070 | 5.121 ±0.681 |
| | RRSRZ | - | - | 0.983 ±0.018 | 0.862 ±0.016 | 0.974 ±0.021 | 0.868 ±0.015 | 0.982 ±0.018 | 0.849 ±0.017 |
| | RSRRE | - | - | -0.421 ±0.081 | 1.432 ±0.132 | -0.661 ±0.068 | 1.384 ±0.061 | -0.719 ±0.064 | 1.624 ±0.084 |
| | RSRRZ | - | - | 0.142 ±0.086 | 29.35 ±192 | 0.514 ±0.076 | 0.761 ±0.291 | 0.532 ±0.075 | 0.676 ±0.262 |
| | RSRSE | - | - | -0.738 ±0.062 | 1.260 ±0.037 | -0.740 ±0.062 | 1.449 ±0.060 | -0.739 ±0.062 | 1.764 ±0.098 |
| | RSRSZ | - | - | -0.617 ±0.072 | 1.832 ±0.135 | -0.445 ±0.078 | 2.628 ±0.379 | -0.536 ±0.074 | 2.747 ±0.321 |
| | RSSRE | - | - | -0.532 ±0.073 | 1.513 ±0.099 | -0.241 ±0.083 | 2.500 ±1.116 | 0.017 ±0.086 | 20.40 ±91 |
| | RSSRZ | - | - | -0.899 ±0.038 | 1.063 ±0.007 | -0.930 ±0.032 | 1.111 ±0.010 | -0.843 ±0.046 | 1.140 ±0.017 |

Fig. 33 c)

Strychnine

$R_{(7)}S_{(8)}S_{(12)}R_{(13)}R_{(14)}S_{(16)}$

| | RDCs (Hz) | | | | | | | | | |
|---|---|---|---|---|---|---|---|---|---|---|
| | P3D PBLG | PBLG | PELG | PMMA | PIAF | PS | PA1 | PL1 | PALV | PADV |
| CH1 | -114.9 | -178.9 | -43.5 | 37.0 | 19.6 | -9.3 | 8.5 | 35.0 | 27.9 | 19.9 |
| CH2 | -118.1 | -36.9 | -15.3 | 22.8 | -3.3 | 0.8 | | -0.5 | -14.9 | -11.7 |
| CH3 | -185.5 | -69.8 | -12.8 | 15.7 | 5.6 | | -16.6 | -18.4 | -11.8 | -5.2 |
| CH4 | -115.7 | -182.4 | -43.5 | 37.8 | 21.2 | -10.5 | 10.6 | 39.5 | 28.0 | 21.5 |
| CH8 | 84.5 | 87.1 | 24.6 | -17.5 | -11.0 | 3.6 | | -5.7 | | |
| CH12 | 200.1 | 146.8 | 32.4 | -40.0 | -10.0 | 11.4 | | | -4.1 | -2.6 |
| CH13 | 15.6 | 48.9 | 12.2 | -11.0 | -5.7 | -3.6 | 3.6 | | -5.8 | -4.8 |
| CH14 | 184.1 | 151.7 | 31.5 | -38.7 | -11.5 | 12.0 | | | -8.4 | -5.4 |
| CH16 | -101.1 | -49.6 | -14.8 | 25.1 | -1.9 | 1.8 | | -6.4 | | |
| CH22 | -34.1 | -1.1 | 3.0 | -2.8 | 2.5 | -6.6 | 6.0 | | 1.0 | 0.0 |

| | P3D PBLG | PBLG | PBDG | PELG | PALF300 | PALF316 | PL1 | PALV | PADV | PPEMG |
|---|---|---|---|---|---|---|---|---|---|---|
| | | | | | RDCs (Hz) | | | | | |
| CH1 | 17.8 | 13.3 | 14.5 | 9.2 | 6.9 | 2.7 | 9.8 | -23.6 | 7.4 | 9.0 |
| CH2 | 2.9 | -7.4 | -5.2 | -12.1 | 5.0 | 4.7 | 34.2 | 13.8 | 1.0 | 12.0 |
| CH3 | 3.7 | 11.1 | 13.1 | 2.9 | 6.0 | -2.7 | 21.6 | 11.6 | 5.3 | 64.0 |
| CH5 | 0.7 | -5.5 | -5.3 | -7.3 | -10.2 | 0.1 | -25.2 | -10.3 | -14.0 | 52.0 |
| CH$_2$4 | 1.1 | -4.0 | -4.4 | -3.4 | -7.6 | -1.3 | -19.7 | 4.6 | -2.9 | -13.0 |
| | 10.8 | 10.9 | 14.3 | -2.4 | 19.0 | 5.5 | 56.2 | -3.8 | 10.0 | 40.0 |
| CH$_2$7 | -27.5 | -16.4 | -17.4 | -9.8 | -4.8 | 2.2 | -0.5 | 15.1 | -1.9 | |
| | -1.5 | 4.1 | 1.9 | 13.6 | 1.2 | -5.5 | -4.7 | 9.5 | 6.9 | |

|  | RDCs (Hz) | | | | | | | |
| --- | --- | --- | --- | --- | --- | --- | --- | --- |
|  | CH1 | CH2 | CH3 | CH4 | CH5 | CH9 | CH10 | CH11 |
| Conformer 1 (33%) | 34.53 | 34.65 | 36.78 | 34.34 | 43.22 | -13.40 | -11.59 | -16.83 |
| Conformer 2 (35%) | 53.20 | 48.10 | 51.00 | 49.61 | 42.23 | -25.31 | 52.39 | -8.60 |
| Conformer 3 (32%) | -0.53 | 1.27 | 0.60 | -1.66 | 59.48 | -27.44 | -10.79 | -19.65 |
| Weighted average | 29.85 | 28.68 | 30.18 | 28.17 | 48.08 | -22.06 | 11.06 | -14.85 |
| Experimental | 22.23 | 17.53 | 23.32 | 21.3 | 52.25 | -19.79 | 3.12 | -17.74 |

|  | RDCs (Hz) | | | | | | | |
| --- | --- | --- | --- | --- | --- | --- | --- | --- |
|  | CH1 | CH2 | CH3 | CH4 | CH5 | CH9 | CH10 | CH11 |
| Conformer 1 | 34.53 | 34.65 | 36.78 | 34.34 | 43.22 | -13.40 | -11.59 | -16.83 |
| Conformer 2 | 53.20 | 48.10 | 51.00 | 49.61 | 42.23 | -25.31 | 52.39 | -8.60 |
| Conformer 3 | -0.53 | 1.27 | 0.60 | -1.66 | 59.48 | -27.44 | -10.79 | -19.65 |
| Conformers 1/2 (w. a. 97/3%) | 35.09 | 35.05 | 37.21 | 34.80 | 43.19 | -13.76 | -9.67 | -16.58 |
| Conformers 1/3 (w. a. 59/41%) | 20.16 | 20.96 | 21.95 | 19.58 | 49.89 | -19.16 | -11.26 | -18.00 |
| Conformers 2/3 (w. a. 36/64%) | 18.81 | 18.13 | 18.74 | 16.80 | 53.27 | -26.67 | 11.95 | -15.67 |
| Conformers 1/2/3 (w. a. 29/22/49%) | 21.46 | 21.25 | 22.18 | 20.06 | 50.97 | -22.90 | 2.88 | -16.40 |
| Experimental | 22.23 | 17.53 | 23.32 | 21.3 | 52.25 | -19.79 | 3.12 | -17.74 |

METHOD FOR DETERMINATION OF THE ANISOTROPIC PARAMETERS FOR THE CONFIGURATION OF ORGANIC MOLECULES EMBEDDED IN ALIGNMENT MEDIA

The invention relates to a method for determination of molecular parameters for a configuration of a known single organic molecule embedded in an anisotropic environment generated by alignment media, said known organic molecule comprising particles. The invention further relates to a method for determining the relative configuration of organic molecules embedded in alignment media. The invention further relates to a data processing apparatus comprising means for carrying out the steps of the above methods, a computer program product comprising instructions which, when the computer program is executed by a computer, cause the computer to carry out the steps of the above methods, and a computer readable storage medium comprising instructions which, when executed by a computer, cause the computer to carry out the steps of the above methods.

NMR spectroscopy is a powerful technique for the assignment of the constitution and configuration of small molecules and natural products. Insufficient NMR data or misinterpretation of available data, however, has led to structural misassignments of many compounds (as disclosed e.g. in Nicolaou, K. C. & Snyder, S. A. Chasing molecules that were never there: Misassigned natural products and the role of chemical synthesis in modern structure elucidation. *Angew Chem Int Edit* 44, 2050-2050 (2005); and Liu, Y. et al. Unequivocal determination of complex molecular structures using anisotropic NMR measurements. *Science* 356, eaam5349 (2017)), which in-turn can lead to incorrect conclusions around structure-activity relationships or other important criteria.

To overcome these problems, methods based on anisotropic NMR parameters are known. Anisotropic NMR-based parameters are sensitive reporters of the global orientation of molecular bonds and chemical shielding tensors and thus provide a robust means for structure assignment/validation of complex organic molecules. Access to anisotropy-based NMR parameters requires the generation of anisotropic environments in solution through the use of dedicated alignment media.

A. Saupe and G. Englert: High-resolution nuclear magnetic resonance spectra of oriented media. Physical Review Letters Vol. 11, No. 10, 15.11.1963, pp. 462-464 discloses a method for determining the orientation of molecules by use of a NMR spectra.

Residual dipolar couplings (RDCs) are powerful anisotropy-based NMR data, which represent dipole-dipole interactions scaled by the degree of molecular alignment.

N. Tjandra, A. Bax: Direct Measurement of Distances and Angles in Biomolecules by NMR in a Dilute Liquid Crystalline Medium. Science, Vol. 278 (5340), 07.11.2997, p. 1111-1114 discloses the determination of a molecular alignment tensor from residual dipolar couplings RDCs measured by NMR.

K. Berlin, D. P. O'Leary, D. Fushman: Improvement and analysis of computational methods for prediction of residual dipolar couplings. Journal of Magnetic Resonance, Vol. 201 (2009) p. 25-33 describes a method for computing the molecular alignment tensor and predicting residual dipolar couplings by reformulating the planar barrier model as a numerical integration problem and by using a convex hull rather than a detailed representation of the surface of a molecule.

RDCs provide a spatial view of the relative orientations of bonds irrespective of internuclear distances. For structure elucidation of small molecules and natural products, experimentally observed RDCs are compared with values expected on the basis of the proposed molecular constitution and configuration. In the absence of a connection between the atomic structure of the alignment medium and the expected RDCs, this comparison is based on a mathematical minimization procedure (as disclosed in Y. Liu, R. D. Cohen, G. E. Martin, R. Th. Williamson: A Practical Strategy for the Accurate Measurement of Residual Dipolar Coupling in Strongly Aligned Small Molecules. Journal of Magnetic Resonance, 2018, Vol. 291, p. 63-72). Consequently, utilization of RDCs for structural assignment strongly depends on the number and quality of experimentally observed RDCs, as well as the quality of the structure proposed for the small molecule. The technique therefore fails in cases where internuclear vectors are nearly parallel to each other or if they are located in a single plane. Measurement of RDCs in different alignment media may increase the amount of data available to determine the correct constitution and configuration. In addition, restraints based on residual chemical shift anisotropy (RCSA) minimize degeneracies when used in combination with RDCs, but RCSAs are more prone to measurement error than RDCs.

J. L. Lorieau: Mollib: a molecular and NMR data analysis software. Journal of Bio-molecular NMR (2017) 69, p. 69-80 describes the techniques for analysis of molecular structures, in particular the formulas for calculating the RDCs and residual anisotropic chemical shift (RACS), wherein the RDC and RACS values are fit to a molecular structure using a Singular Value Decomposition (SVD).

A. Navarro-Vázquez: MSpin-RDS. A program for the use of residual dipolar couplings for structure elucidation of small molecules. Magn. Reson. Chem. 2012, 50, p. 575-579 also discloses the computation of alignment tensors using SVD in detail.

The connection between the atomic structure of an alignment medium, the molecular structure of small molecules, and molecule-specific anisotropy-based NMR parameters has remained enigmatic.

It is an object of the present invention to provide a method for determination of the anisotropic parameters for a configuration of organic molecules embedded in alignment media and a related data processing apparatus, computer program product and computer readable storage medium.

The object is achieved by the method according to claim 1 and the related dependent claims.

The anisotropic parameters for configurations of organic molecules embedded in alignment media are determined by the steps of:
a) Defining a three-dimensional grid that is aligned with the known atomic structure of the alignment medium;
b) Placing the particles of the known single organic molecule on the respective grid points of the three-dimensional grid in relation to at least one assigned atom of the alignment medium;
c) Determining the interaction between the particles of the single organic molecule and the alignment medium for a plurality of configurations of the organic molecule;
d) Determining anisotropic parameters obtainable by measuring with nuclear magnetic resonance (NMR) spectroscopy by use of the determined interactions for each of the plurality of configurations of the particles.

The steps c) and d) can be repeated for different orientations of the organic molecules in order to achieve a set of anisotropic NMR parameters each related to a specific configuration. The configurations can be generated by computational chemistry methods.

Friedrich, N. O. et al. Benchmarking Commercial Conformer Ensemble Generators. *J Chem Inf Model* 57, 2719-2728 (2017) discloses methods for generation of configurations of organic molecules.

A particle representing each configuration of the organic molecule is then placed on a point of the grid and rotated through a set of rotational angles. This procedure is repeated for all points on the three-dimensional grid.

The provision of a three-dimensional grid aligned with the atomic structure of the alignment medium and the positioning of the particles of the organic molecules on an assigned grid point of the grid has the effect, that a very uniform distribution with a defined reference to the atom of the alignment medium interacting with a particle is ensured and thus even small deviations from the isotropic distribution can be easily detected. The anisotropic NMR parameters can then be determined for a set of configurations, wherein the rotational state of the particles are well defined in the homogenous grid. The interaction between the particles of the organic molecule and the alignment medium is determined for each configuration with the same position and the same set of predefined orientations of the particle on the grid relative to the related atoms of the alignment medium. The positioning of the particles on the three-dimensional grid has the effect of a highly homogenous distribution of the particles resulting in a very sensitive method.

The molecular alignment simulation according to the present invention accurately predicts RDCs in small molecules dissolved in organic solvents from the three-dimensional structure of the alignment medium. The technique overcomes current limitations in the use of RDCs for determination of complex molecular structure and establishes a quantitative correlation between anisotropy-based NMR parameters, the atomic structure of the alignment medium and the constitution and configuration of small molecules.

Correct structural assignment of small molecules and natural products is critical for drug discovery and organic chemistry. Anisotropy-based nuclear magnetic resonance (NMR) spectroscopy is a powerful tool for structural assignment of organic molecules, but relies on utilization of a medium that disrupts the isotropic motion of molecules in organic solvents.

The present invention allows a quantitative correlation between the atomic structure of the alignment medium, the molecular structure of the small molecule and mole-cule-specific anisotropic NMR parameters. The quantitative correlation makes use of an accurate three-dimensional molecular alignment model that predicts residual dipolar couplings of small molecules aligned for example by poly(γ-benzyl-L-glutamate).

The technique facilitates reliable determination of the correct diastereomer and enables unequivocal, rapid determination of complex molecular structures from extremely sparse NMR data.

In a preferred embodiment, the determination of the interaction between the organic molecule and the alignment medium in step c) comprises evaluating of the steric effects and/or evaluating of the van der Waals forces and/or evaluating of the electrostatic forces acting between a respective organic molecule and the alignment medium. The determination of the anisotropic parameters for a specific configuration of organic molecules can be improved by evaluating the electrostatic forces in addition to the evaluation of the steric effects and/or evaluating of the van der Waals forces.

In a further improved embodiment, the method comprises the additional steps of:

e) Comparing anisotropic parameters measured by nuclear magnetic resonance (NMR) spectroscopy for the organic molecule embedded in the alignment medium with the anisotropic parameters calculated for each of the possible configurations of the organic molecule, and f) Determining the configuration of the organic molecule Thus, the set of anisotropic parameters determined by simulation with the steps a) to d) for a set of configurations of the organic molecule are compared with the anisotropic parameters measured by use of nuclear magnetic resonance (NMR) spectroscopy. The configuration of the measured organic molecule can be determined as the configuration related to the set of simulated anisotropic parameters showing the best fit to the measured anisotropic NMR parameters.

Preferably, the determination of the interaction in step c) comprises determining potential energies between the organic molecule and the related atoms of the alignment medium by calculating a respective equation of steric obstruction and/or van der Waals interaction and/or continuum electrostatics.

The potential energies determined in step c) can be converted into probabilities for the orientation of the respective organic molecule in front of the alignment medium by use of the Boltzmann equation.

In a preferred embodiment, the organic molecule is placed in step b) outside the radius defined by the van der Waals force of the related atom of the alignment medium in its three-dimensional atomic structure for determining the interaction of the organic molecule and the related atom of the known alignment medium in step c).

Alignment tensors of the organic molecule can be calculated for the respective points of the three-dimensional grid by use of the probabilities for orientation of the particles of the organic molecule.

The object is further solved by the method for determining the configuration of organic molecules embedded in alignment media comprising the additional step of comparing anisotropic NMR parameters determined by the simulation method described above with anisotropic molecular parameters measured by NMR spectroscopy.

This allows to determine the configuration of the organic molecule embedded in an alignment medium as the configuration of the organic molecule with the best fit of simulated and measured NMR parameters.

Preferably, the step of comparing comprises calculating a quality parameter (RQ) with a term comprising the Pearson correlation coefficient (R) and a scaled quality factor, wherein the configuration related to the highest quality parameter is determined as the configuration of the organic molecule. The use of a quality parameter combining the Pearson correlation coefficient and a scaled quality factor provides a stable result for a full range of organic molecules.

The quality parameter (RQ) can be calculated, for example, by the formula $(R+1)^2/Qs$, wherein R is the Pearson correlation coefficient of the linear fitting of the observed residual dipolar couplings (RDCs) measured by nuclear magnetic resonance (NMR) spectroscopy ($D^{exp}$) versus the calculated residual dipolar couplings (RDCs) obtained by simulation ($D^{calc}$), and wherein the scaled quality factor Qs is calculated by the slope of the fitting for the quality factor $Q=\text{rms}(D^{exp}-D^{calc})/\text{rms}(D^{exp})$, with rms indicating the root-mean-square.

The object can be further achieved by a data processing apparatus comprising means for carrying out the steps of the above specified methods, a computer program product comprising instructions which, when the computer program is executed by a computer, cause the computer to carry out the steps of the above specified methods and a computer readable storage medium comprising instructions which, when executed by a computer, cause the computer to carry out the steps of the above specified method.

The invention is further explained by way of examples using the attached drawings. The drawings shows:

FIG. 1—Schematic diagram of the method for determination of the anisotropic parameters for the configuration of an organic molecule embedded in an alignment medium;

FIG. 2—Three-dimensional molecular alignment simulation;

FIG. 3—Diastereomers of DAHPA;

FIG. 4—Diastereomers of IPC;

FIG. 5—Diastereomers of strychnine;

FIG. 6—Diastereomers of caulamidine;

FIG. 7—Diastereomers of CPDMPPPC;

FIG. 8—Diastereomers of parthenolide;

FIG. 9—Correct diastereomers of DAHPA with experimental RDCs;

FIG. 10—Correct diastereomers of IPC with experimental RDCs;

FIG. 11—Correct diastereomers of strychnine with experimental RDCs;

FIG. 12—Correct diastereomers of caulamidine with experimental RDCs;

FIG. 13—Correct diastereomers of CPDMPPPC with experimental RDCs;

FIG. 14—Correct diastereomers of parthenolide with experimental RDCs;

FIG. 15—Visualization of the alignment of the hygrophorone DAHPA in the anisotropic environment of a PBLG particle;

FIG. 16—Comparison of the orientation of the alignment tensor of DAHPA predicted by the present invention and prior art methodology;

FIG. 17a)-b)—Correlation between RDCs predicted by the method of the present invention and experimental values for 4 RDCs and 8 RDCs;

FIG. 18a)-c)—Influence of structural dynamics of PBLG on RDC prediction along a 1 ns molecular dynamic simulation FIG. 19—Structure of the correct diastereomer together with the experimental RDCs and the Pearson's correlation coefficient between measured RDCs and RDCs predicted by the present invention for the different diastereomers of the small molecule DAHPA; prior art methodology (SVD) cannot be used with only 4 RDCs;

FIG. 20—Structure of the correct diastereomer together with the experimental RDCs and the Pearson's correlation coefficient between measured RDCs and RDCs predicted by the present invention and prior art methodology for the different diastereomers of the small molecule IPC;

FIG. 21—Structure of the correct diastereomer together with the experimental RDCs and the Pearson's correlation coefficient between measured RDCs and RDCs predicted by the present invention and prior art methodology for the different diastereomers of the small molecule strychnine;

FIG. 22—Structure of the correct diastereomer together with the experimental RDCs and the Pearson's correlation coefficient between measured RDCs and RDCs predicted by the present invention and prior art methodology for the different diastereomers of the small molecule caulamidine;

FIG. 23—Structure of the correct diastereomer together with the experimental RDCs and the Pearson's correlation coefficient between measured RDCs and RDCs predicted by the present invention for the different diastereomers of the small molecule CPDMPPPC; prior art methodology (SVD) cannot be used with only 4 RDCs;

FIG. 24—Structure of the correct diastereomer together with the experimental RDCs and the Pearson's correlation coefficient between measured RDCs and RDCs predicted by the present invention for the different diastereomers of the small molecule parthenolide; prior art methodology (SVD) cannot be used with only 4 RDCs;

FIG. 25—Unequivocal structure elucidation of small molecules by calculating a quality parameter (RQ);

FIG. 26—Shape representation of the distribution of partial charges in DAHPA, IPC, strychnine, CPDMPPPC, caulamidine and parthenolide;

FIG. 27—Visualization of the orientation of the alignment tensors predicted by the present invention for the correct diastereomer of IPC with those derived by the prior art;

FIG. 28—Visualization of the orientation of the alignment tensors predicted by the present invention for the correct diastereomer of strychnine with those derived by the prior art;

FIG. 29—Visualization of the orientation of the alignment tensors predicted by the present invention for the correct diastereomer of caulamidine with those derived by the prior art;

FIG. 30—Visualization of the orientation of the alignment tensors predicted by the present invention for the correct diastereomer of CPDMPPPC with those derived by the prior art;

FIG. 31—Visualization of the orientation of the alignment tensors predicted by the present invention for the correct diastereomer of parthenolide with those derived by the prior art;

FIG. 32—Influence of the structures of the small molecules on alignment tensor prediction;

FIG. 33a)-c)—Tables of the R and Qs quality parameters for different diastereomers and molecular alignment models;

FIG. 34—Representation of the basic units of anisotropic media used for the alignment of strychnine (s) and (−)-IPC (i);

FIG. 35—Strychnine structure together with the CH carbon labels and the correct configuration, as well as the respective lists of RDCs in the different alignment media;

FIG. 36—(−)-IPC structure together with the CH carbon labels and the correct configuration, as well as the respective lists of RDCs in the different alignment media;

FIG. 37a)—Matrix of Pearson's correlation R between P3D-calculated RDCs and the experimental RDCs in different alignment media for strychnine;

FIG. 37b)—Comparison of the orientation of the P3D-predicted alignment tensor with alignment tensors derived by SVD from experimental RDCs of the different alignment media for strychnine;

FIG. 38a)—Matrix of Pearson's correlation R between P3D-calculated RDCs and the experimental RDCs in different alignment media for (−)-IPC;

FIG. 38b)—Comparison of the orientation of the P3D-predicted alignment tensor with alignment tensors derived by SVD from experimental RDCs of the different alignment media for (−)-IPC;

FIG. 39*a*)—Correlation between P3D-simulated RDCs (DP3D) and experimental RDCs (Dexp) with different alignment media for strychnine;

FIG. 39*b*)—Diastereomer discrimination power of different alignment media for strychnine based on the P3D simulation and using the RQ ratio for judging the quality of correlation;

FIG. 39*c*)—Comparison of the orientation of the P3D-predicted alignment tensor of strychnine with alignment tensors derived by SVD from the experimental RDCs using PALES observed in different alignment media;

FIG. 39*d*)—Oriented structures of strychnine according to the PBLG-based P3D simulation and the different experimentally analyzed alignment media;

FIG. 40*a*)—Sucrose structure with the CH carbons labeled;

FIG. 40*b*)—List of P3D-simulated RDCs for the 3 conformers together with the average weighted RDCs and the experimental RDCs;

FIG. 40*c*)—Correlations between the experimental RDCs (Dexp) and the P3D-simulated RDCs for the 3 conformers and the weighted average;

FIG. 40*d*)—RQ ratios of the 3 different conformers in reference to the weighted average;

FIG. 40*e*)—Comparison of the orientation of the P3D-predicted alignment tensors for the 3 conformers;

FIG. 41*a*)—List of P3D-calculated RDCs for the 3 conformers together with the average weighted RDCs from the RQ maximization for 2- and 3-conformer ensembles and the experimental RDCs;

FIG. 41*b*)—Correlation between the experimental RDCs (Dexp) and the P3D-calculated RDCs for the weighted average of the RQ maximization for 2- and 3-conformer ensembles;

FIG. 41*c*)—RQ ratios of the three different conformers in reference to their weighted average as 2- and 3-conformer ensembles. Error bars were calculated as the propagation of R and Qs errors and these errors are calculated from the std of 100 repetitions including noise in the RDCs.

FIG. 1 shows a schematic diagram of the method for determination of the anisotropic parameters for a configuration of an organic molecule embedded in alignment media.

In the step a) a three-dimensional grid is defined, that is aligned with the known atomic structure of the alignment medium. Thus, each atom of the alignment medium is e.g. placed inside a cube of a grid.

In the step b), the particles of the organic molecule of interest are placed on the respective grid points of the three-dimensional grid in relation to at least one assigned atom of the alignment medium.

In the step c), the interaction between the particles of the organic molecule and the alignment medium is determined for the plurality of possible configurations of the organic molecule. To this end, particles representing each configuration of the organic molecule are placed as described in the step b), and rotated through a set of rotational angles. This procedure is repeated for all points on the three-dimensional grid. The provision of a homogenous grid aligned with the atomic structure of the alignment medium and the constant position of each particle on a respective grid point for each configurations safeguards a high accuracy of the determined anisotropic parameters calculated for the simulated model.

In the step d), the anisotropic parameters, obtainable by measuring with nuclear magnetic resonance (NMR) spectroscopy, are calculated by use of the interactions determined in step c) for each of the plurality of configurations of the organic molecule.

In the following, the three-dimensional molecular alignment model considered for the method is described in more detail:

To establish a correlation between the structure of the alignment medium and the configuration of small molecules and RDCs, an atomic structure-based alignment model according to the method of the present invention is provided (in the following briefly "P3D"). P3D uses grid-based sampling of solute positions/orientations in front of particles that form the alignment medium. Highly uniform grid-based sampling of solute positions/orientations overcomes the challenge of simulating very weak degrees of molecular alignment, which are required to retain the high resolution of NMR spectra of organic molecules, i.e. deviations from isotropic sampling amounting to only ~0.1% and thus corresponding to the alignment of only 1 out of 1000 solute molecules. Grid-based alignment simulation is available in the prior art e.g. with the soft-ware PALES, which predicts RDCs in biomolecules. In contrast to the prior art PALES implementation, which represents the alignment medium only as an infinite wall/cylinder, i.e. not in atomic detail, the newly developed P3D model is based on the three-dimensional structure of the alignment particle.

FIG. 2 shows an exemplary three-dimensional molecular alignment simulation using the three-dimensional structure of the alignment particle.

In the P3D simulations, the small molecule is moved outward from the center of the alignment particle until all of its atoms are outside the van der Waals radius of all at-oms of the alignment particle. Then the alignment particle is sampled along the main axis, while its curved edge is sampled in angular steps with the angle between two points remaining constant for increasing distances from the surface of the alignment particle. For each point on the grid and a predefined set of orientations, the potential energies between the alignment particle and the small molecule are calculated by solving the equations of continuum electrostatics. Potential energies are subsequently converted to probabilities for molecular orientations of the small molecule in front of the alignment particle using the Boltzmann equation. With these different weights for each of the points on the three-dimensional grid, the alignment tensor is calculated, and from it, the RDCs. This is also shown in FIG. 2.

For implementation of the three-dimensional alignment simulation, for example, poly(γ-benzyl-L-glutamate) (PBLG) can be selected. PBLG has a well-defined α-helical structure and forms a lyotropic liquid crystalline phase, which is widely used for measurement of RDCs in small molecules. The three-dimensional model of the PBLG particle is built by poling the α-helical building block along its helical axis, as shown in FIG. 2. Subsequently, the PBLG structure is energy minimized and equilibrated in a chloroform box, e.g. using the molecular simulation software GROMACS.

In the following, the evaluation criteria for RDC simulation is described.

To analyze the structure of small molecules using RDCs, robust measures for the comparison of experimentally observed RDCs ($D^{exp}$) with values calculated from the molecular structure ($D^{calc}$) are desired. Traditionally, these include the Pearson correlation coefficient R of the linear fitting of the $D^{exp}$ vs $D^{calc}$ representation and the RDC quality factor $Q=rms(D^{exp}-D^{calc}/rms\ D^{exp})$ with rms indicating root-mean square.

Preferably, an additional quality parameter, which combines the Pearson correlation coefficient R and the scaled quality factor $Q_s$ into one parameter termed $RQ=(R+1)^2/Q_s$ is used for the comparison. To decrease the influence of the magnitude of alignment, the quality factor is calculated with RDCs scaled by the slope of the fitting $Q_s$. The use of R+1 in RQ avoids negative values, while the square enhances the relative importance of R. This RQ parameter increases the discriminative power for the RDC-based distinction of multiple configurations, because wrong diastereomers can produce small $Q_s$ values and at the same time large negative R values when using molecular alignment simulation (negative R values generally do not occur in SVD analysis), especially with a small number of RDCs. The RQ parameter will approach zero for poor predictions of molecular alignment. For the comparison of different diastereomers of one compound, the values are preferably normalized to the largest RQ value observed for any of the possible diastereomers.

The method according to the present invention P3D is in the following evaluated on the basis of RDCs measured for six molecules dissolved in chloroform and weakly aligned in PBLG: the fungicidal cycloheptenone 4,6-diacetylhygrophorone A (DAHPA), isopinocampheol (IPC), the two alkaloids strychnine and caulamidine, 2-(4-chlorophenyl)-5-(dimethylphosphoryl)-4-phenyl-pyrrolidin-3-carboxylate (CPDMP-PPC), and the sesquiterpene lactone parthenolide. The six small molecules have different numbers of diastereomers ranging from 4 for DAHPA to 16 for parthenolide.

The plurality of possible diastereomers of these six small molecules are shown in FIGS. 3 to 8.

The 3D coordinates of the different diasteromers of the six molecules are generated through computational chemistry methods on the basis of the corresponding constitution and respective relative configuration.

FIGS. 9 to 14 show the correct diastereomers of DAHPA, IPC, Strychnine, Caulamidine, CPDMPPPC and Parthenolide together with the experimental RDCs.

The molecular simulation predicts the PBLG-induced alignment as described in the following example:

The natural product DAHPA, extracted from the mushroom genus *Hygrophorus*, has two stereogenic centers in the cycloheptenone ring (C4 and C5; FIG. 9) and one exocyclic center at C6, thus potentially eight stereoisomers. The absolute configuration of DAHPA is unknown. The four relative configurations 4R,5S,6R, 4R,5R,6R, 4S,5R,6R and 4R,5R,6S are termed RSR, RRR, SRR and RRS (see FIG. 3).

FIG. 15 shows a visualization of the alignment of the hygrophorone DAHPA in the anisotropic environment of a PBLG particle. The PBLG-induced alignment of the correct diastereomer of DAHPA (RSR) is simulated using the method of the present invention P3D. The predicted orientation of DAHPA in the frame of the diagonalized alignment tensor is shown in FIG. 15. The axis corresponding to the largest eigen-value of the alignment tensor ($S_{zz}$) is oriented along the alkyl chain of DAHPA (FIG. 3).

FIG. 16 shows a comparison of the orientation of the alignment tensor of DAHPA predicted by the present invention and prior art methods. The visualization of the alignment tensor axes in the context of a two-dimensional world map shows that the orientation of the $S_{zz}$-axis predicted by P3D is highly similar to the orientation derived by SVD-based minimization. The angle between the P3D-predicted and SVD-derived $S_{zz}$-axis is 2.5°. Good agreement is also observed between the simulated and SVD-derived orientations of the other two alignment tensor axes (FIG. 16). Because the $S_{yy}$- and $S_{xx}$-axis correspond to smaller eigenvalues (in this order), their orientation shows a larger spread (see for example the variation in the SVD-derived orientation of the $S_{xx}$-axis).

FIGS. 17A) and B) show the correlation between RDCs predicted by the present in-vention P3D ($D^{calc}$) and experimental values ($D^{exp}$; A, 4 one-bond CH RDCs; B, 4 one-bond+4 long-range CH RDCs). The CH RDCs are calculated on the basis of the alignment tensor predicted by the method according to the present invention P3D and compared to the experimental values.

For the example, linear fitting of the $D^{exp}$ vs $D^{calc}$ representation resulted in a Pearson correlation coefficient of 0.84 when considering only the four one-bond CH RDCs (FIG. 17A) and supplementary tables in FIG. 33a) to c)). Inclusion of the small, long-range CH RDCs did not affect the value of the Pearson correlation coefficient (FIG. 17B)). Similar Pearson correlation coefficients were also obtained when experimental RDCs were compared to those predicted for the structures generated by the cheminformatics software RDkit using either the Merck Molecular Force Field (MMFF) or the Universal Force Field (UFF) (see FIG. 32)).

The comparison of the predicted and SVD-derived alignment tensor orientation in FIG. 16, and the $D^{exp}$ vs $D^{calc}$ representations in FIGS. 17A) and B), suggest that RDC calculation is sensitive to the precise parameters of the alignment tensor, in particular the orientation of the alignment tensor axes. In addition, the RDC strongly depends on the orientation of the individual internuclear vector relative to the molecular alignment tensor, while the alignment tensor itself depends less on the local structure but is mostly influenced by the overall conformation of the molecule. Despite these challenges in the prediction of RDCs by molecular alignment simulation, the good fit between the experimental RDCs and those simulated for the correct diastereomer of DAHPA demonstrates that the developed three-dimensional alignment model accurately predicts PBLG-induced alignment of DAHPA.

The alignment simulation according to the present invention P3D is robust against changes in PBLG structure.

The P3D simulation is based on the atomic structures of both the small molecule and the alignment particle (FIG. 2). To evaluate the influence of changes in the atomic structure of PBLG on RDC prediction, a 1 ns molecular dynamics simulation of a PBLG particle in a box of chloroform was performed.

FIG. 18 shows the influence of structural dynamics of PBLG on RDC prediction along a 1 ns molecular dynamic simulation. FIG. 18a) shows an overall view of the PBLG structure and FIG. 18b) the central part of the PBLG structure.

FIG. 18c) shows the variation R of $D^{exp}$ vs $D^{calc}$ Pearson correlation coefficients due to structural changes of the PBLG particle during the 1 ns molecular dynamic simulation of PBLG shown in FIGS. 6a) and b). The PBLG particle was aligned along the z-axis and one-bond CH RDCs were predicted by P3D according to the present invention using the 100 Å central part for each 10 ps snapshot and compared with the experimental RDCs of DAHPA, IPC, strychnine, caulamidine, CPDMPPPC and parthenolide. The superposition of all PBLG central part structures from FIG. 18b) are shown inside the plot.

From the simulation, snapshots of the PBLG particle were taken every 10 ps (FIG. 18a)-b). For each snapshot, P3D simulations were performed for DAHPA, followed by comparison of predicted RDCs with $D^{exp}$. Despite pronounced changes in the structure of the PBLG particle (FIG. 18b), only small variations in the RDCs predicted for DAHPA (and the other five molecules; see below) and thus the calculated Pearson correlation coefficient were observed (FIG. 18c). The analysis indicates that changes in the conformation of PBLG, such as bending of the PBLG particle and variation with the side chain orientations (FIG. 18a)-b)), do not strongly affect P3D simulations and thus the ability of molecular alignment simulations for structural analysis of small molecules.

By way of example, the identification of the correct diastereomer of DAHPA (out of all six small molecules; FIG. 19-24) from 4 CH RDCs is described in the following.

The complete relative configuration of DAHPA is difficult to establish using scalar couplings and NOEs, because of its quaternary carbon C5. Encouraged by the high quality of the alignment prediction for the RSR diastereomer (FIGS. 15-18), P3D simulations by use of the method according to the present invention are performed for the other three diastereomers of DAHPA (FIG. 19) and predicted their RDCs (FIG. 19, upper right). Linear fitting of the $D^{exp}$ vs $D^{calc}$ representation resulted in the Pearson correlation coefficients 0.73, 0.78 and 0.27 for RRR, SRR and RRS, respectively (FIG. 19; Table 1 in FIG. 33a)-b)). The values are lower than the Pearson correlation coefficient of the RSR diastereomer (R=0.84).

To support the identification of the RSR configuration as the correct diastereomer, we calculated the RQ ratio for the four diastereomers using the four CH RDCs (FIG. 25; Table 1 in FIGS. 33a)-c)). Consistent with the ranking by the Pearson correlation coefficient, the largest RQ ratio was obtained for the RSR diastereomer. Notably, for SVD-based analysis of the alignment tensor of a non-symmetric molecule such as DAHPA at least five linearly independent RDCs are required. In contrast to the P3D-based analysis, SVD-based ranking of the four diastereomers of DAHPA therefore strictly depends on the contribution of the small long-range RDCs, which are—because of their small size—difficult to measure reliably. The analysis demonstrates that molecular alignment simulation unequivocally determines the correct diastereomer of DAHPA from only four one-bond CH RDCs.

The steric obstruction dominates PBLG-induced alignment of DAHPA as explained in the following.

To gain insight into the forces influencing the small molecule alignment generated by PBLG, we preformed additional molecular alignment simulations of the four diastereomers of DAHPA. In these additional simulations, we did not use continuum electrostatics to calculate the interaction energies between the PBLG atoms and the DAHPA atoms, but instead calculated their van der Waals interaction. Notably, both the PBLG particle and DAHPA were represented in atomic detail, i.e. full three-dimensional simulations were performed. The results from these simulations were termed "3D vdW".

Linear fitting of the $D^{exp}$ vs $D^{calc}$ representation for the "3D vdW" simulations resulted in the Pearson correlation coefficients 0.89, 0.62, 0.74 and 0.01 for the RSR, RRR, SRR and RRS diastereomers of DAHPA, respectively (Table 1 in FIGS. 33a)-c)). The corresponding RQ ratios were 1.0, 0.261, 0.506 and 0.001 (Table 1 in FIG. 33a)-c)). Thus, for all four diastereomers the Pearson correlation coefficients obtained from the "3D vdW" simulation are similar to those derived from the P3D simulation. In addition, the Pearson correlation coefficients obtained for the configuration RSR, i.e. for the correct diastereomer, are very similar in the case of the "3D vdW" and the P3D simulation.

Motivated by the importance of van der Waals interactions for the alignment of DAHPA and the small influence of changes in PBLG structure on RDC prediction (FIG. 18), RDCs are also predicted in DAHPA using the previously developed one-dimensional obstruction model (termed "1D"). The 1D model does not take into account the atomic structure of the alignment medium and only considers steric obstruction. Indeed, the RDC prediction quality achieved by the 1D model for DAHPA aligned by PBLG was similar to the "3D vdW" and the P3D simulation (Table 1 in FIGS. 33a)-c)).

The similarities in the alignment predictions observed for the three distinct alignment models suggest that steric obstruction dominates the weak, PBLG-generated alignment of DAHPA. Inspection of the overall shape of the DAHPA structure supports this interpretation: the alkyl chain gives DAHPA a highly anisotropic, hammer-like shape (upper left in FIG. 26). When the DAHPA molecule approaches the PBLG-particle in such a way that the stalk of the "hammer" is orthogonal to the surface of the PBLG particle, it will result in steric clash. DAHPA will thus preferentially align with its alkyl chain along the surface of the PBLG particle. This is indeed what is observed and shown in FIG. 15.

A three-dimensional alignment simulation is required to predict RDCs in IPC.

As shown in FIG. 10, IPC is a small molecule, having three chiral centers (C1 (alternatively C5), C2 and C3) and potentially eight stereoisomers. The levorotatory compound is used as reference (1R,2R,3S) and the other three diastereomers are 1R,2S,3S, 1R,2S,3R and 1R,2R,3R subsequently termed RRS, RSS, RSR and RRR (FIGS. 4 and 10).

Eight individual CH RDCs can be used to test the quality of the P3D alignment simulation. Linear fitting of the $D^{exp}$ vs $D^{calc}$ representation for the P3D prediction of the correct diastereomer (RRS) resulted in a Pearson correlation coefficient of 0.84 (FIG. 20; Table 1 in FIGS. 33a)-c)). Smaller R values were obtained for the other three diastereomers (FIG. 20).

The result of a prediction of the RDCs of IPC using the "3D vdW" as well as the 1D obstruction model is described in the following.

Using these two alignment models, which do not consider continuum electrostatics, the Pearson correlation coefficient for the correct diastereomer (RRS) of IPC was 0.67 and 0.68, respectively (Table 1 in FIGS. 33a)-c)). Very similar R values were also observed for the RSS configuration. Comparison of RQ values further high-lighted that the simplified alignment models are not sufficient to represent the alignment mechanism of IPC in PBLG (Table 1 in FIGS. 33a)-c)). Indeed, the "3D vdW" calculation gave the highest RQ ratio for the RSS configuration (Table 1 in FIGS. 33a)-c)), i.e. it would select a wrong diastereomer.

Inspection of the properties of IPC in terms of the partial charge distribution and over-all shape supports the importance of continuum electrostatics for the PBLG-generated alignment of IPC. IPC is strongly polarized, but has a rather spherical shape when compared to DAHPA (FIG. 26). In contrast to DAHPA, the full P3D alignment model is therefore required to predict RDCs in IPC with high accuracy and enable identification of the correct diastereomer.

The alignment simulation empowers reliable RDC-based determination of molecular structure.

To further evaluate the robustness and reliability of the P3D calculations according to the present invention for the prediction of alignment tensors and RDCs of small molecules aligned by PBLG, molecular alignment simulations are performed for the diastereomers of strychnine, caulamidine, CPDMPPPC and parthenolide.

FIG. 11 shows that strychnine has six chiral centers (C7, C8, C12, C13, C14 and C16) but from the expected 64 combinations only 26 are possible. The 13 diastereomers generated are 7R,8S,12S,13R,14R,16S, 7R,8S,12R,13S, 14R,16S, 7R,8S,12R,13S,14S,16S, 7R,8S,12R,13R,14R, 16S, 7R,8S,12S,13S,14R,16S, 7R,8S,12R,13R,14S,16S, 7R,8S,12S,13S,14S,16S, 7R,8S,12S,13R,14S,16S, 7S,8S, 12R,13S,14S,16R, 7S,8S,12S,13S,14S,16R, 7S,8S,12R, 13R,14S,16R, 7S,8S,12S,13R,14S,16R and 7R,8S,12R,13S, 14S,16R, subsequently termed RSSRRS, RSRSRS, RSRSSS, RSRRRS, RSSSRS, RSRRSS, RSSSSS, RSSRSS, SSRSSR, SSSSSR, SSRRSR, SSSRSR and RSRSSR (see FIG. 5).

Figure 1:
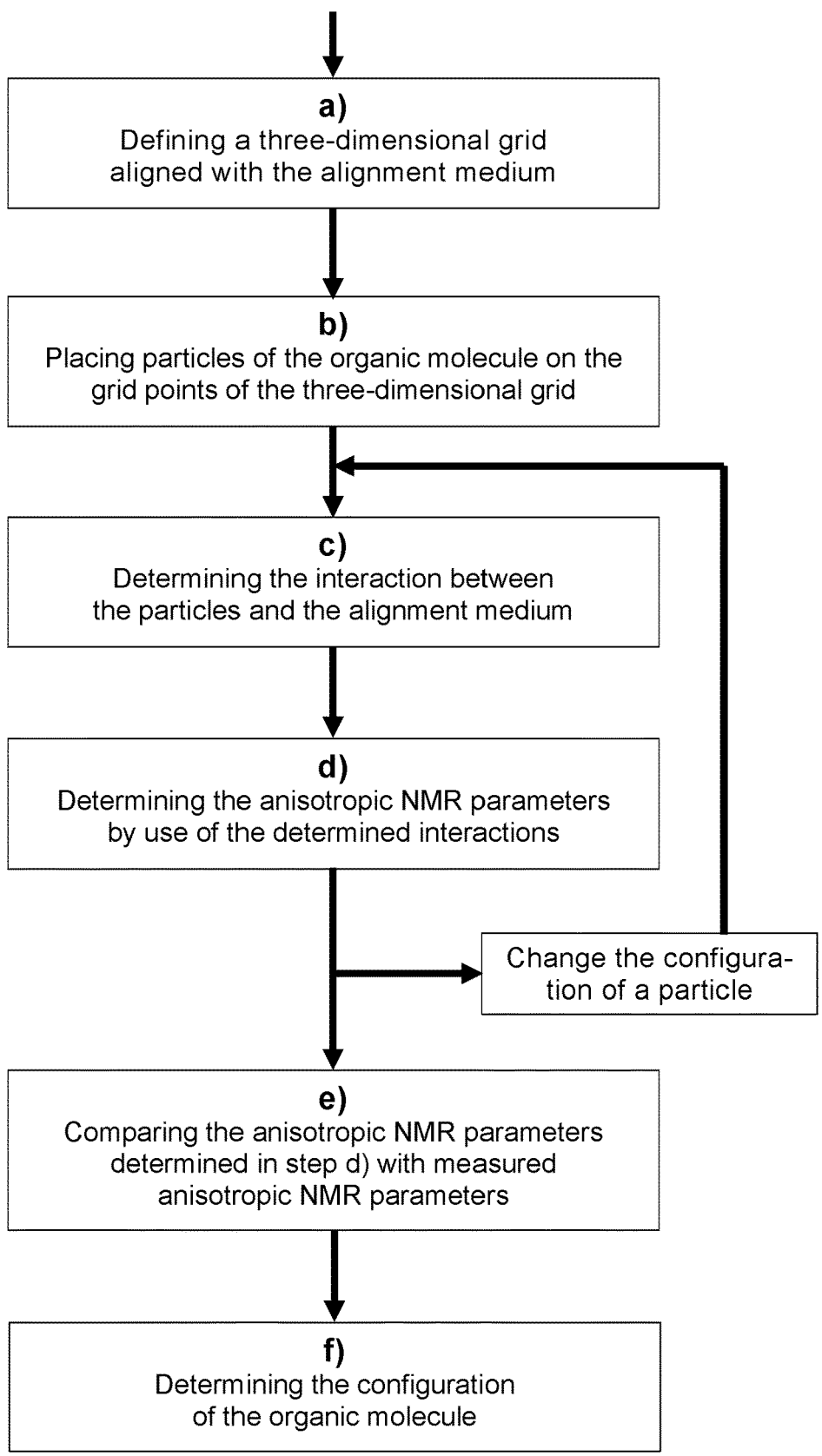
Figure 2:
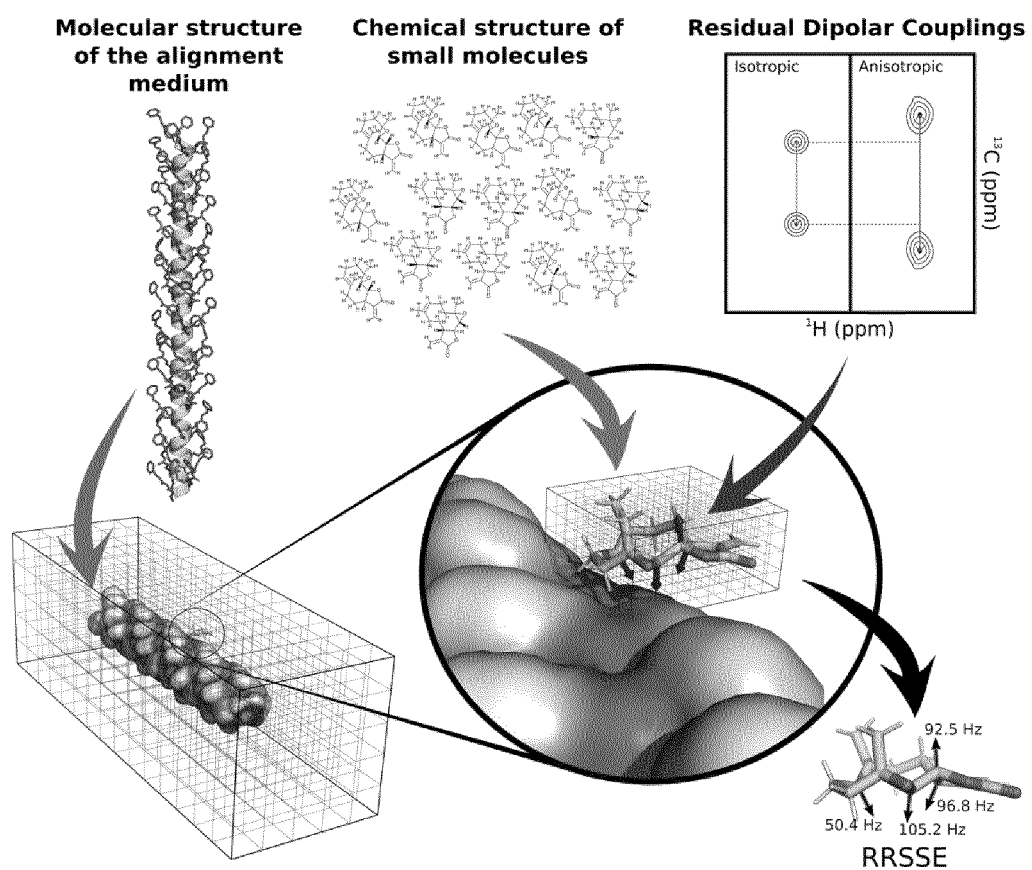
Figure 3:
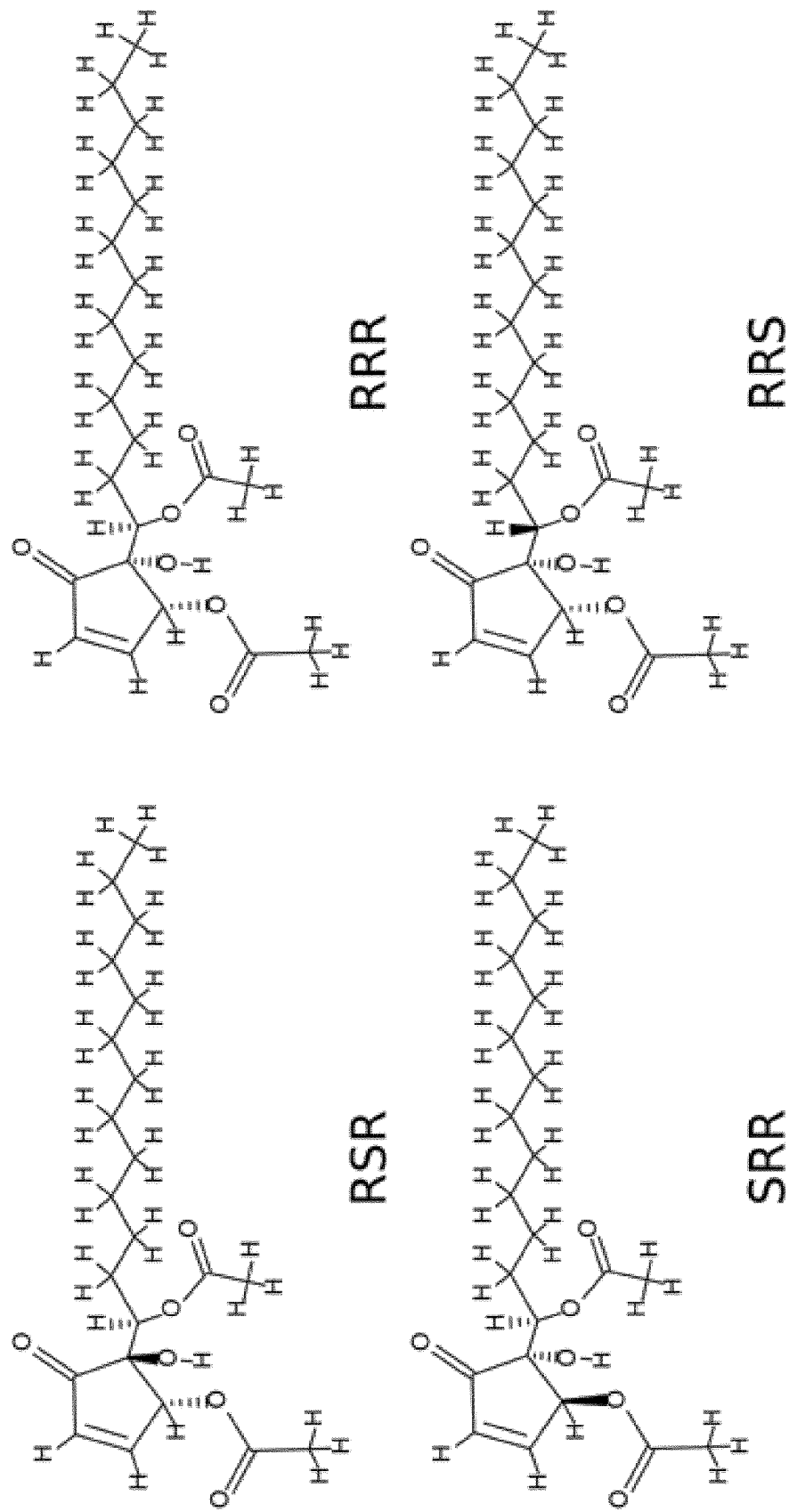
Figure 4:
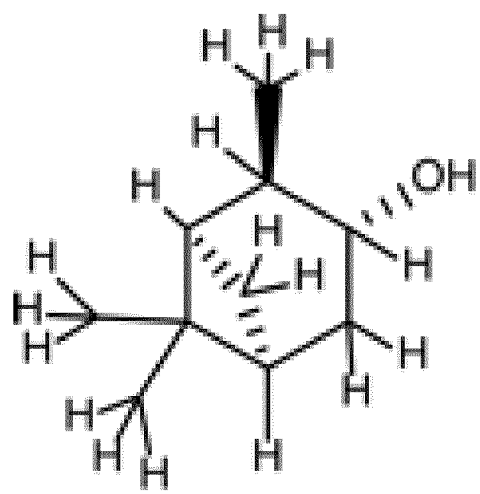
Figure 4:
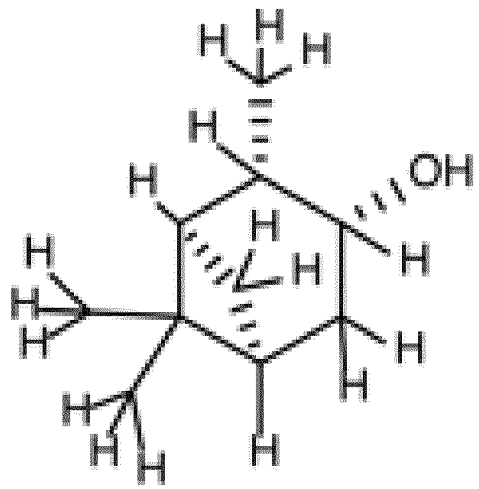
Figure 4:
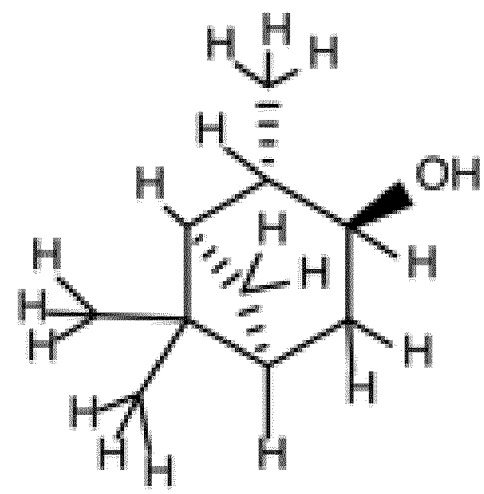
Figure 4:
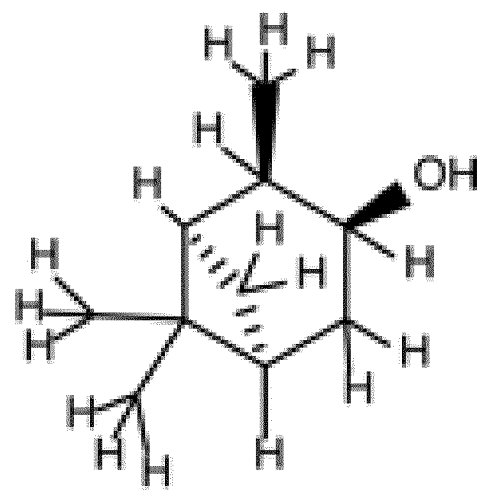
Figure 5:
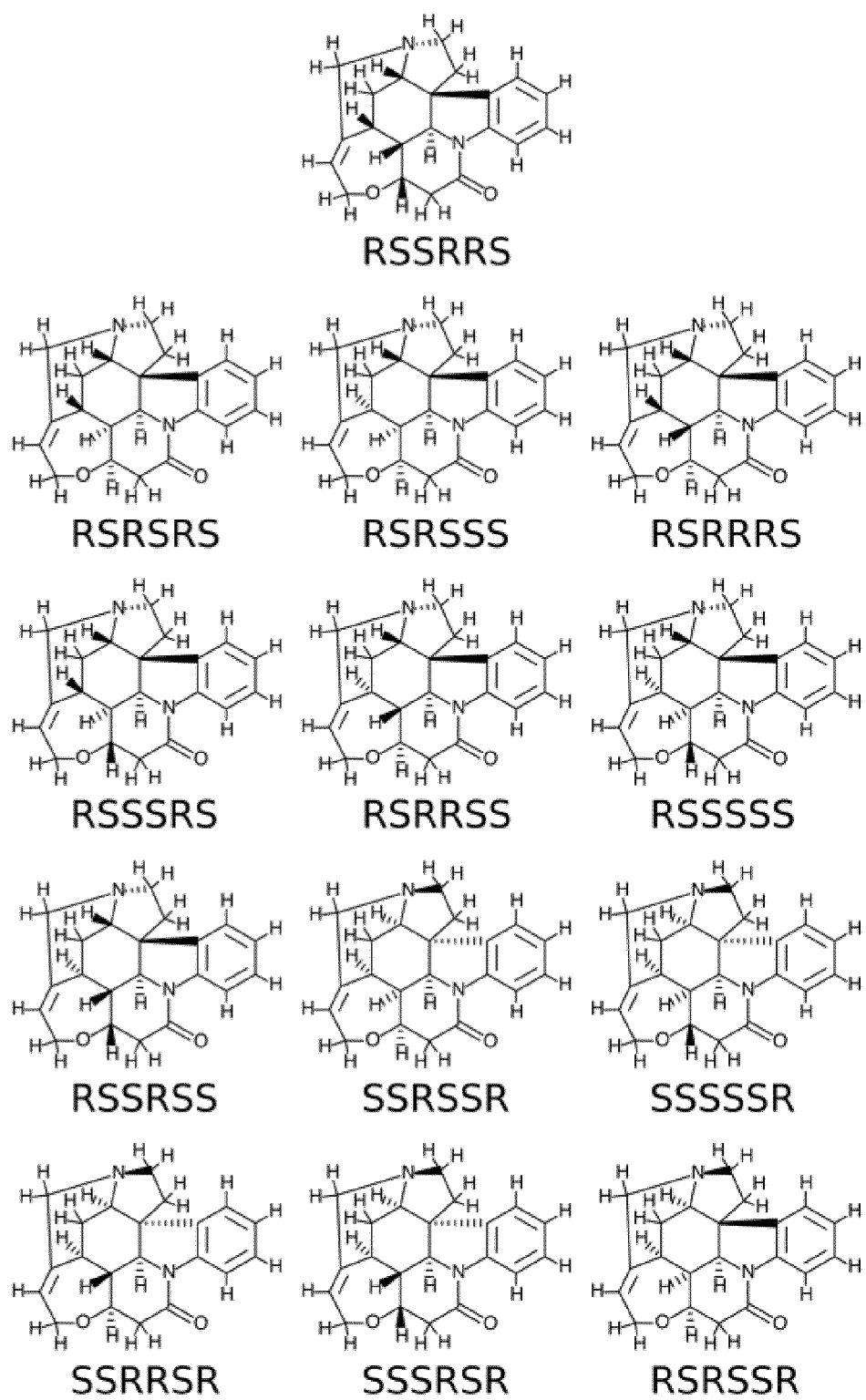
Figure 6:
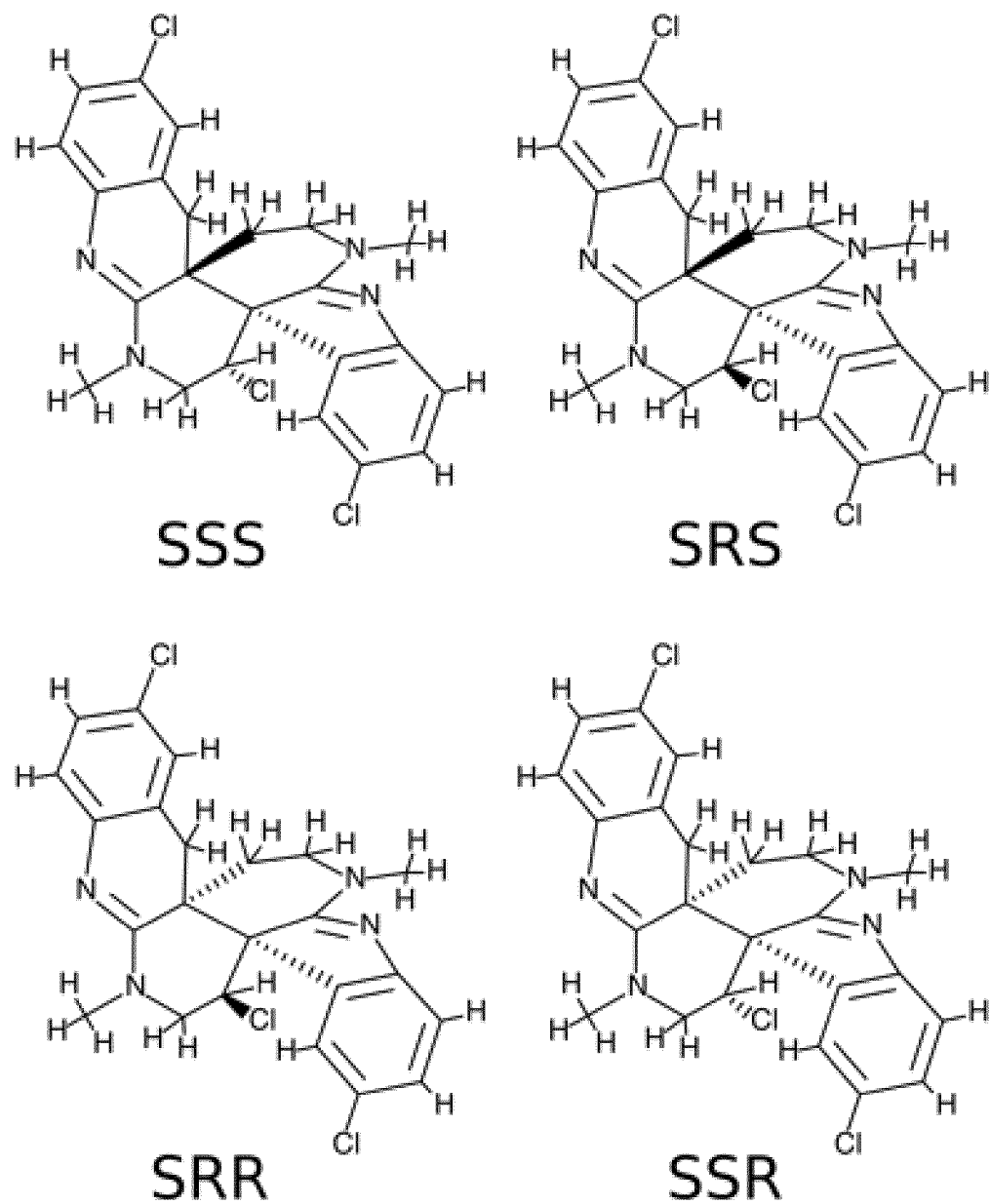
Figure 7:
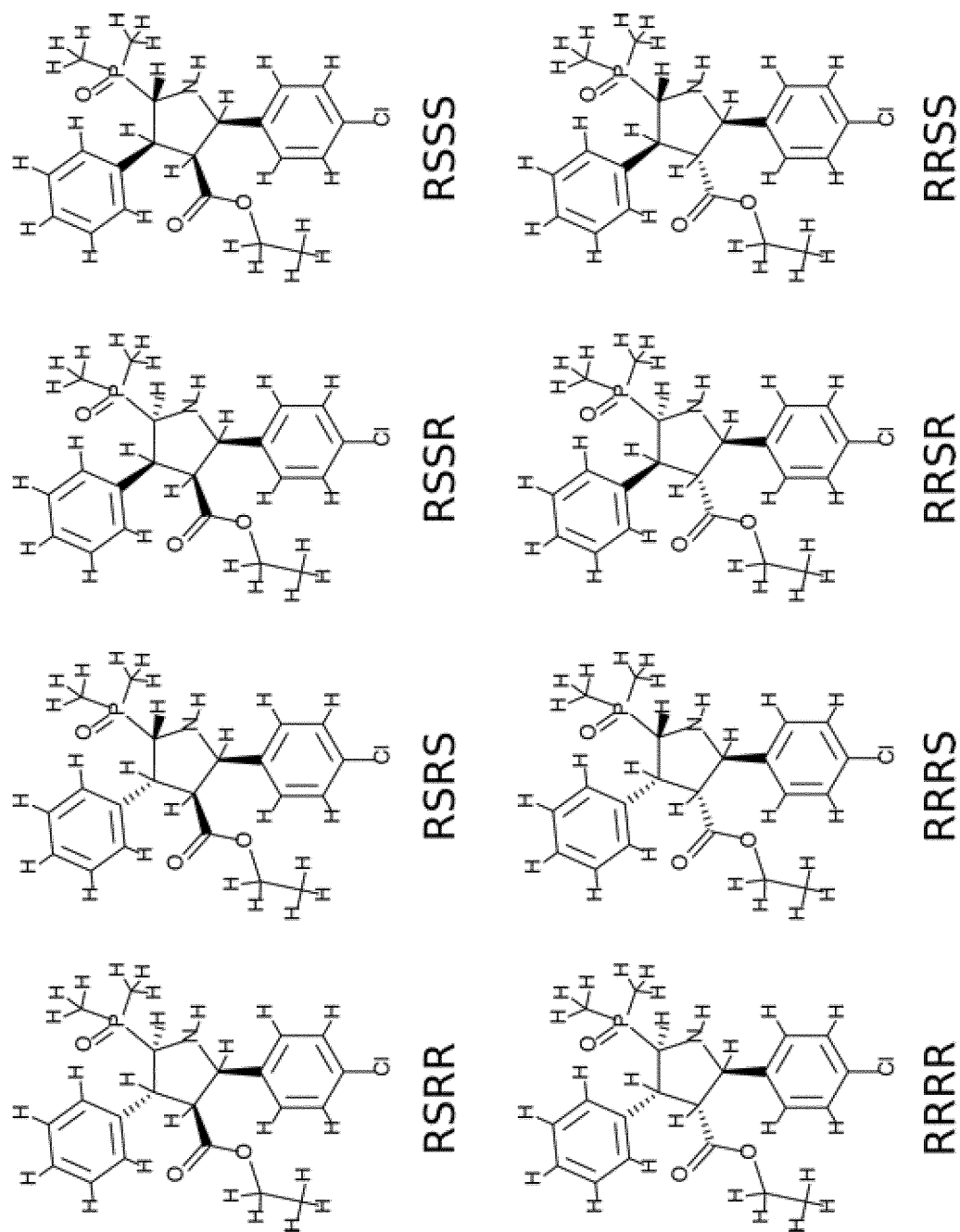
Figure 8:
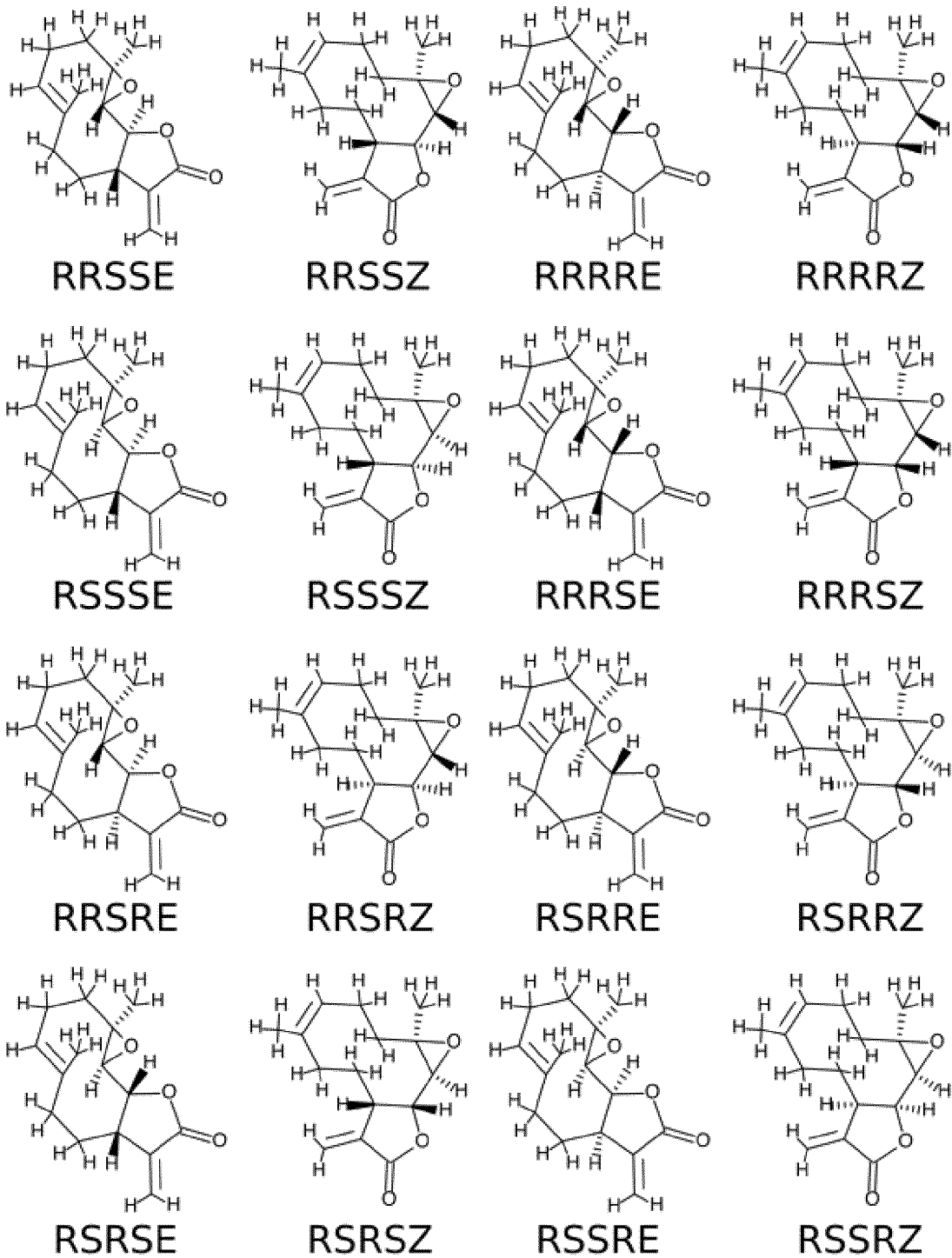
Figure 9:
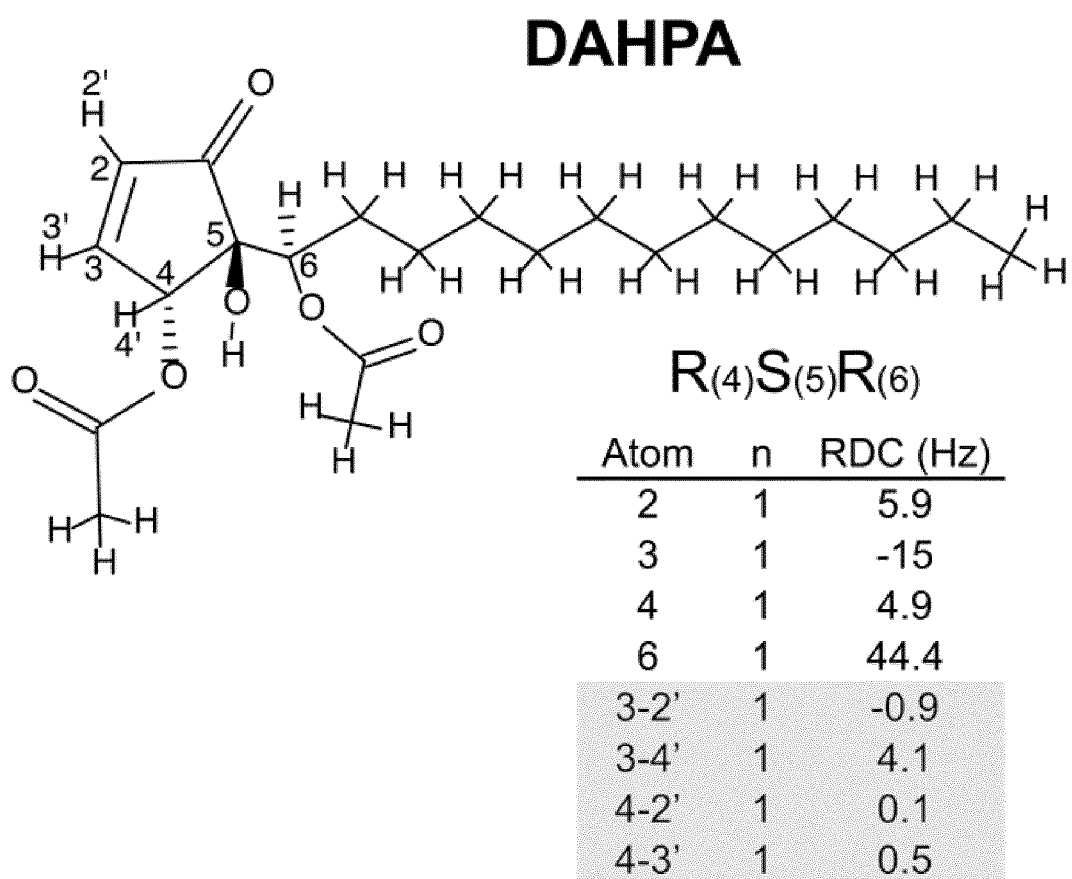
Figure 10:
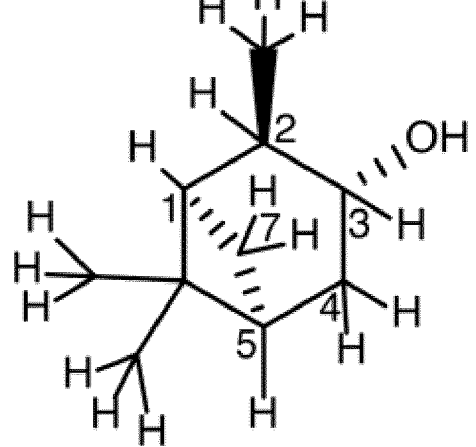
Figure 11:
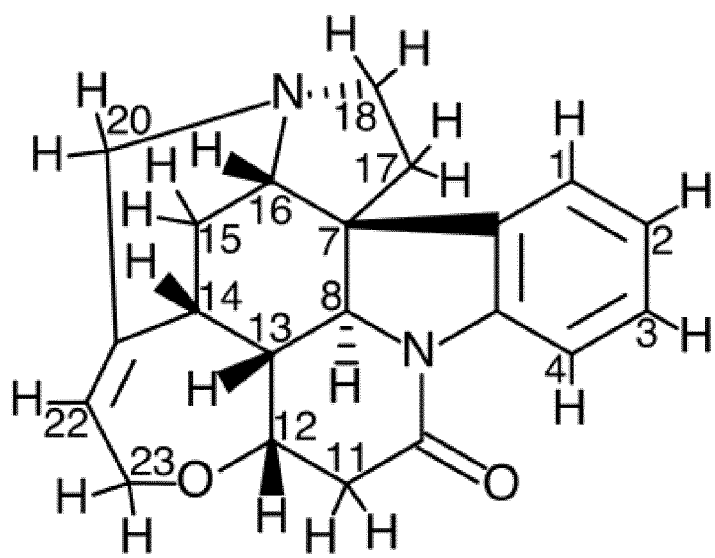
Figure 12:
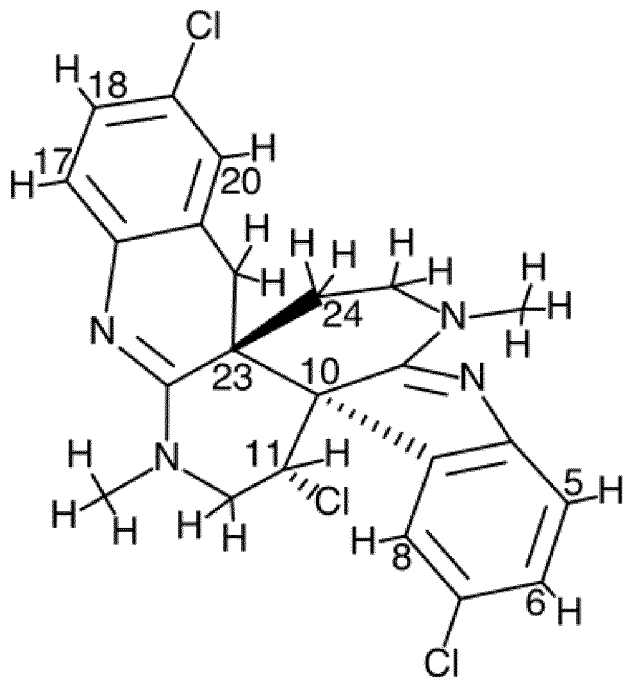
FIG. 12 shows that caulamidine has three stereogenic centers in the heterocyclo-hexane ring (C10, C11 and C23) generating eight stereoisomers, four enantiomers of the other four. The diastereomers we use are 10S,11S,23S, 10S,11R,23S, 10S,11R,23R and 10S,11S,23R, subsequently termed SSS, SRS, SRR and SSR (see FIG. 6).
Figure 13:
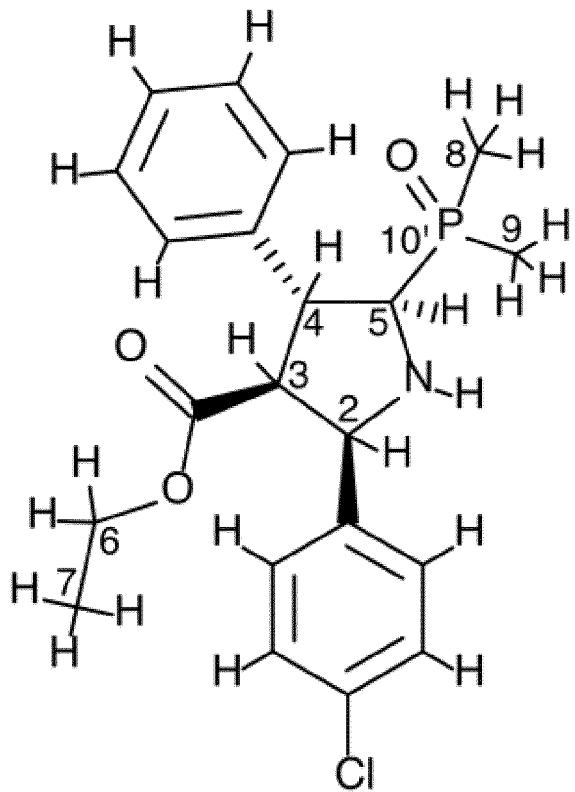
FIG. 13 shows that CPDMPPPC has four chiral centers (C2, C3, C4 and C5) with 16 stereoisomers possible. The eight non-enantiomeric cases are 2R,3S,4R,5R, 2R, 3S, 4R, 5S, 2R, 3S, 4S, 5R, 2R,3S,4S,5S, 2R,3R,4R,5R, 2R, 3R, 4R, 5S, 2R,3R,4S,5R and 2R,3R,4S,5S, subsequently termed RSRR, RSRS, RSSR, RSSS, RRRR, RRRS, RRSR and RRSS (see FIG. 7).
Figure 14:
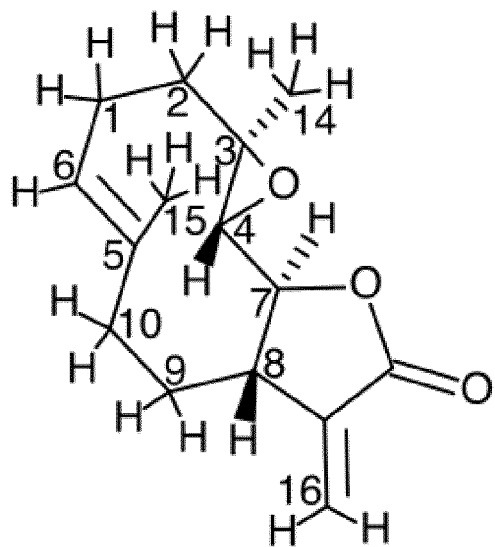

FIG. 14 shows that parthenolide has four chiral centers (C3, C4, C7 and C8) and one geometric isomerism (between C5 and C6) generating 32 stereoisomers. The 16 relative configurations are 3R,4R,7S,8S,E, 3R,4R,7S,8S,Z, 3R,4R, 7R,8R,E, 3R,4R,7R,8R,Z, 3R,4S,7S,8S,E, 3R,4S,7S,8S,Z, 3R,4R,7R,8S,E, 3R,4R,7R,8S,Z, 3R,4R,7S,8R,E, 3R,4R,7S, 8R,Z, 3R,4S,7R,8R,E, 3R,4S,7R,8R,Z, 3R,4S,7R,8S,E, 3R,4S,7R,8S,Z, 3R,4S,7S,8R,E and 3R,4S,7S,8R,Z, which are termed RRSSE, RRSSZ, RRRRE, RRRRZ, RSSSE, RSSSZ, RRRSE, RRRSZ, RRSRE, RRSRZ, RSRRE, RSRRZ, RSRSE, RSRSZ, RSSRE and RSSRZ (see FIG. 8).

Figure 21:
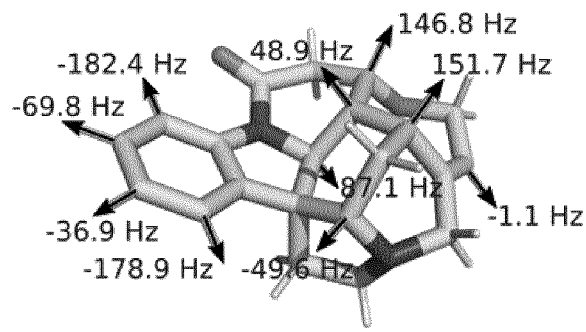
Figure 21:
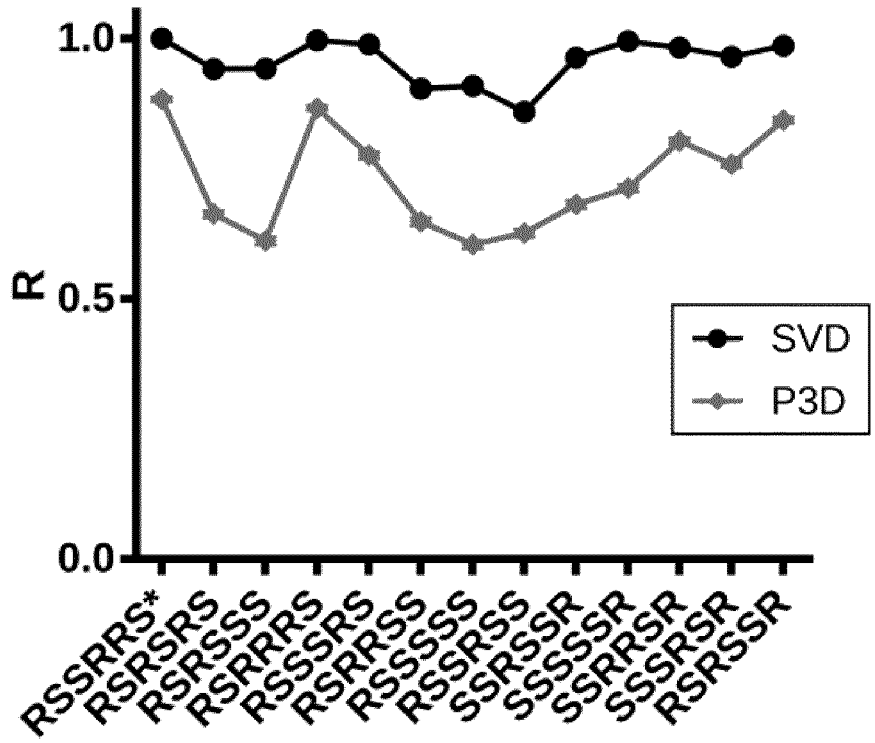
Figure 21:
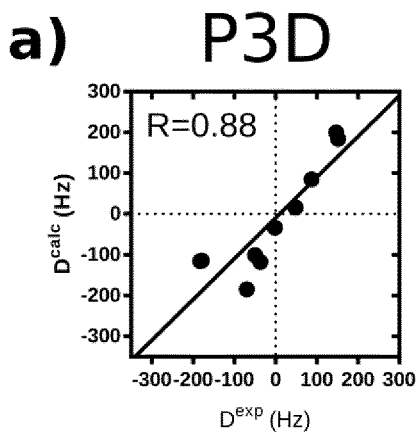
Figure 21:
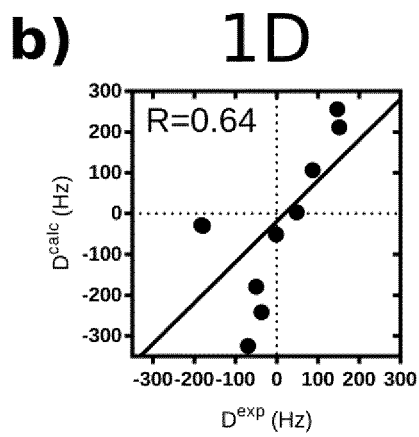

For determination of the relative configuration of strychnine, ten one-bond CH RDCs were measured. Because of the—for a small molecule—quite large number of CH RDCs, the comparison of $D^{exp}$ with values best-fitted to the structure using SVD can exclude many of the 13 possible diastereomers (black line in FIG. 21). RSSRRS, the correct diastereomer, has the highest R value (Table 1 in FIG. 33a)-c)). Most similar in terms of SVD-derived RDCs is the diastereomer RSRRRS (FIG. 21, Table 1 in FIG. 33a)).

The P3D prediction of the PBLG-induced RDCs according to the method of the pre-sent invention for the RSSRRS diastereomer of strychnine and comparison to the experimental RDCs resulted in a Pearson correlation coefficient of 0.88 (FIG. 21a); Table 1 in FIG. 33a)). In contrast, the one-dimensional prediction using the prior art method of the 1D-PALES software resulted in a Pearson correlation coefficient of R=0.64 (FIG. 21b).

The RDCs predicted by P3D for the other diastereomers displayed lower agreement with the experimental RDCs, with the exception of the RSRRRS configuration. Calculation of the RQ ratios and considering the experimental RDC errors supported the P3D-based selection of the RSSRRS configuration (FIG. 25, Table 1 in FIG. 33a)-c)), i.e. the correct diastereomer of strychnine. RDCs predicted on the basis of either the "3D vdW" or the 1D obstruction model correlated significantly worse with the experimental RDCs (Table 1 in FIG. 33a)-c)). Similar to IPC, this is likely due to the non-uniform charge distribution of strychnine (FIG. 26) and thus the importance of electrostatic interactions to the weak alignment of strychnine by PBLG.

Figure 22:
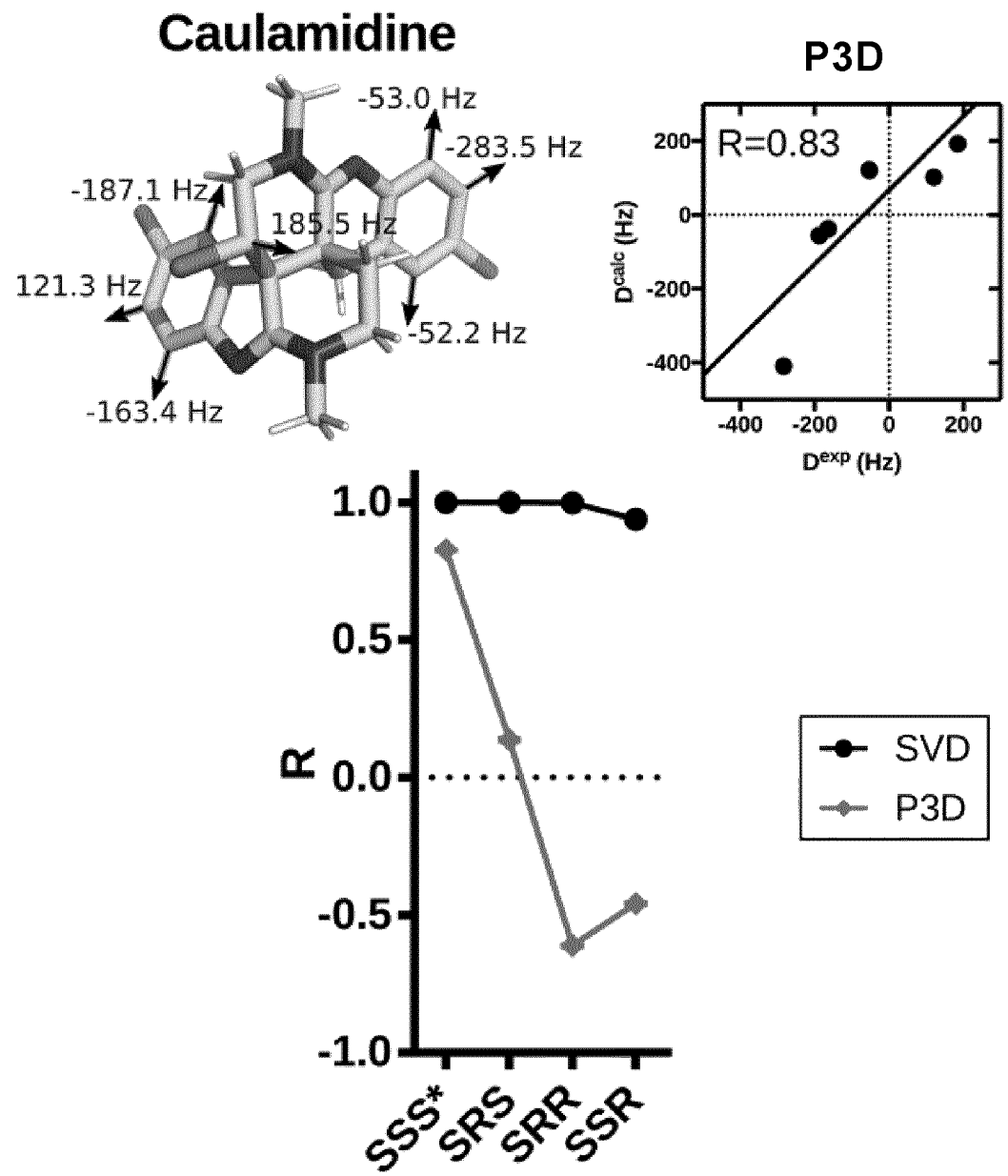

In the case of caulamidine, only the CH RDCs predicted by P3D for the correct diastereomer (SSS) correlate with the experimental values (FIG. 22; Table 1 in FIG. 33b). The RDCs predicted for the other three diastereomers resulted in low Pearson correlation coefficients (FIG. 22) and low RQ ratios (FIG. 25; Table in FIG. 33a)-c)). In contrast, three out of the four diastereomers had Pearson correlation coefficients close to 1.0 in the SVD-based analysis (black line in FIG. 22; Table in FIG. 33b). Comparison of the four diastereomers on the basis of SVD-derived RQ ratios selected the correct diastereomer, although the error estimates for the SRS and SRR diastereomers were large (black line in FIG. 25).

Figure 23:
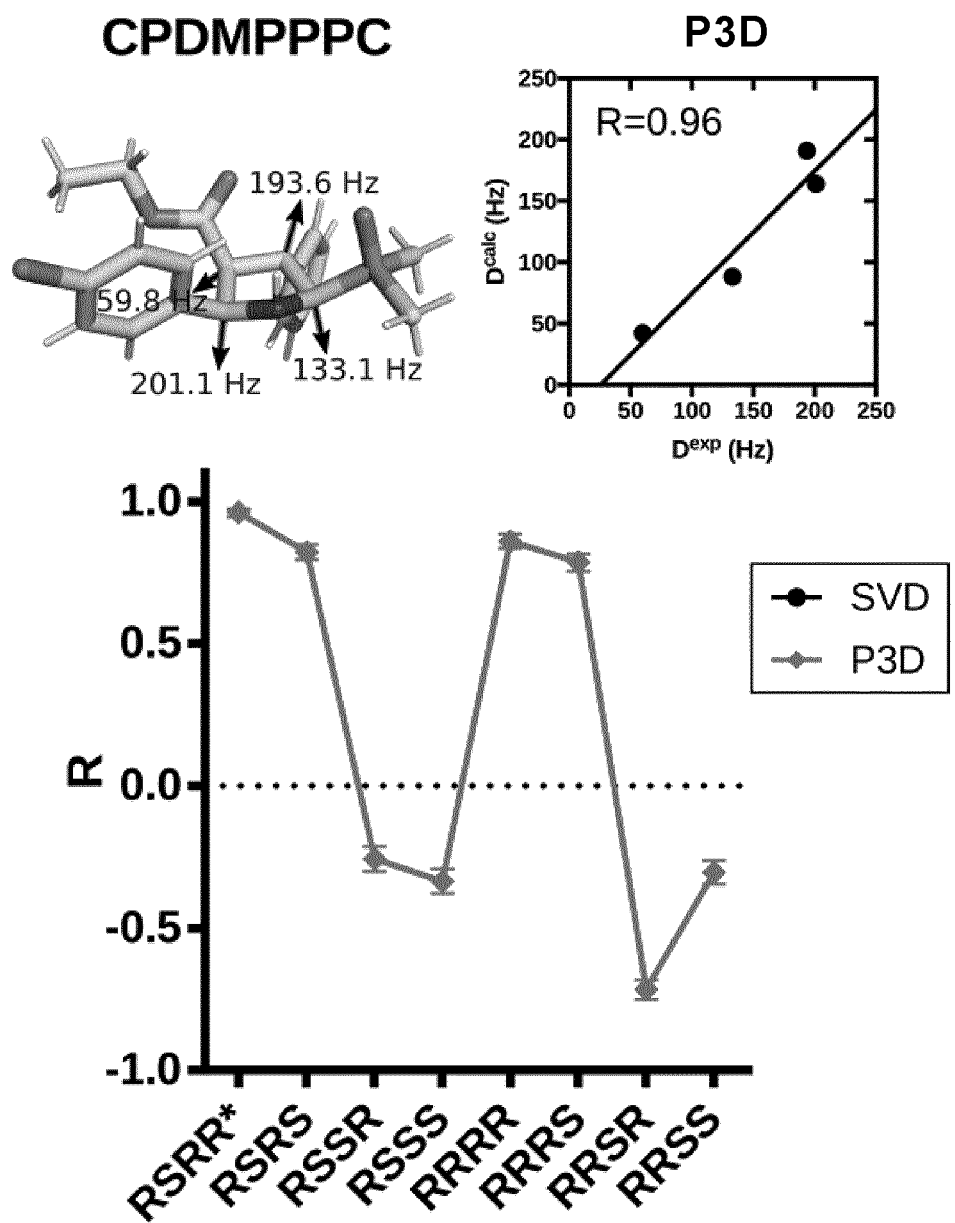

In the case of CPDMPPPC, only four one-bond CH RDCs are known, i.e. less than the minimum number required for SVD. The RDCs predicted by P3D for the RSRR diastereomer were very similar to the experimental values with a Pearson correlation coefficient of 0.96 (FIG. 23; Table in FIG. 33b)). Alignment simulation of the RSRS, RRRR and RRRS stereoisomers also resulted in high Pearson correlation coefficients, while the other four diastereomers displayed negative R values (Table in FIG. 33a)-c)). Calculation of RQ ratios for the eight different diastereomers unequivocally identified the RSRR diastereomer to be correct (FIG. 25; Table in FIG. 33b)).

In the following, an analysis from 16 to 1 diastereomer using 4 RDCs is explained.

The method according to the present invention is performed with a particularly challenging problem, the determination of the correct molecular structure of parthenolide.

Only four one-bond CH RDCs are available, in order to identify the correct configuration from a total of 16 different diastereomers. Parthenolide was subjected to P3D alignment simulation according to the present invention, followed by calculation of RDCs and linear fitting of $D^{exp}$ vs $D^{calc}$. Similar to the other five molecules, the orientation of the axis corresponding to the largest eigenvalue ($S_{zz}$) was predicted with high accuracy for parthenolide.

FIGS. 27 to 31 show visualizations of the orientations of the alignment tensors predicted by the present invention for the correct diastereomers of the small molecules Parthenoide, IPC, Strychnine, Caulamidine and CPDMPPPC with those derived by the prior art.

In the case of strychnine and CPDMPPPC, the SVD-derived orientation of the $S_{yy}$-axis was closer to the P3D-derived orientation of the $S_{xx}$-axis and vice versa. This is related to the definition of the parameters of the alignment tensor, i.e. the largest eigenvalue is labelled as $S_{zz}$, followed by the second largest eigenvalue $S_{yy}$, and then $S_{xx}$. When $S_{yy}$ and $S_{xx}$ have similar magnitude, inaccuracies in RDCs or alignment simulation can result in a "swap" of the $S_{yy}$- and $S_{xx}$-axis, which however has only a small influence on the back-calculation of RDCs from the alignment tensor.

Figure 24:
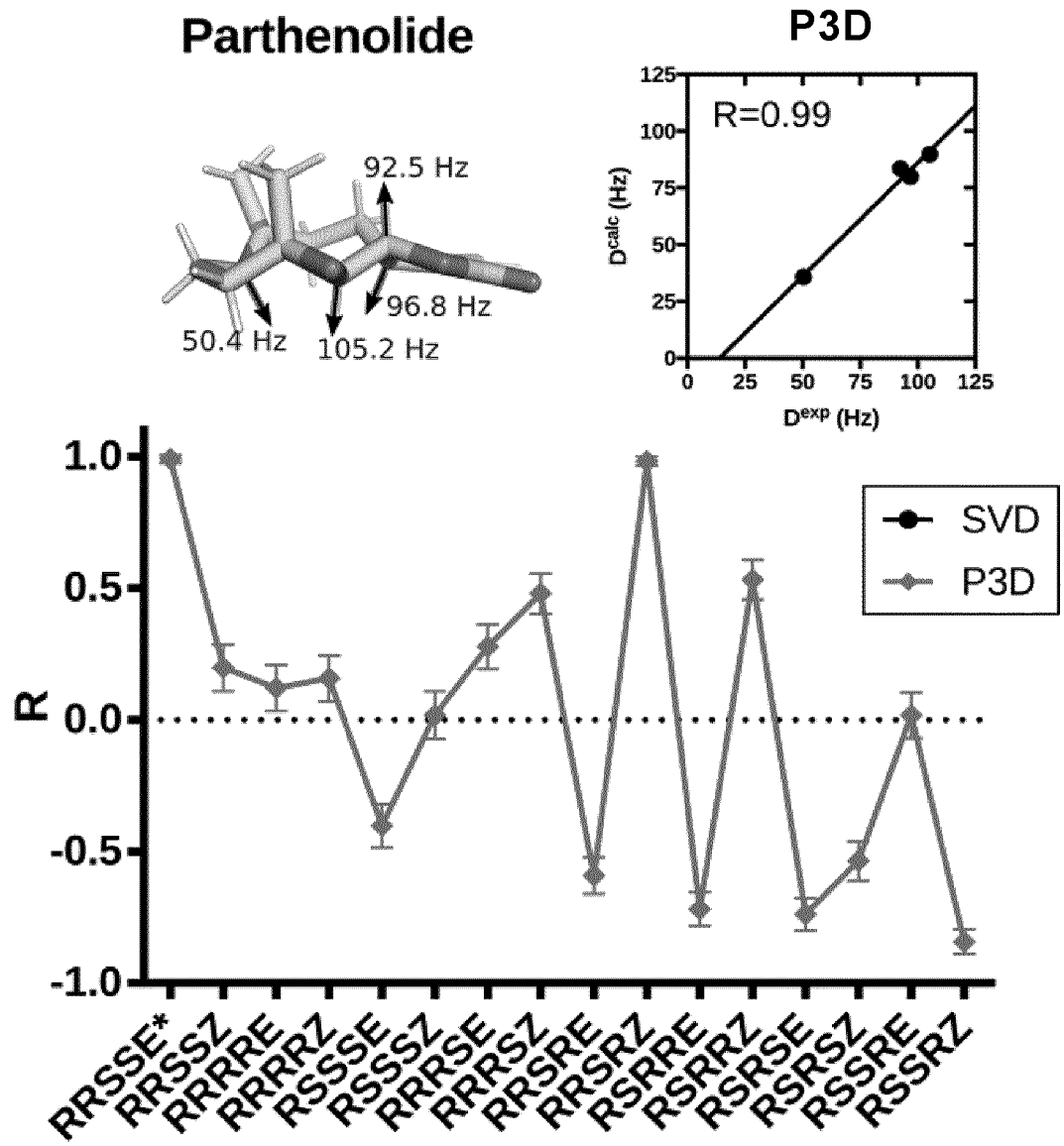

RDCs predicted by P3D for the correct diastereomer (RRSSE) of parthenolide were nearly identical to the experimental values with a Pearson correlation coefficient of 0.99 (FIG. 24; Table in FIG. 33c)). From the other 15 diastereomers analyzed by P3D, only the RRSRZ configuration gave a Pearson correlation coefficient well above 0.5. Inclusion of the magnitude of alignment predicted by P3D through the use of the RQ ratio further enhanced the discrimination (FIG. 25; Table in FIG. 33c)). Thus, the correct diastereomer of parthenolide was selected from 16 possible diastereomers using only four one-bond CH RDCs.

The unequivocal determination of complex small molecule structures using molecular alignment simulation is explained by use of the following Figures in more detail.

FIGS. 3 to 8 represent diastereomers of DAHPA, IPC, strychnine, caulamidine, CPDMPPPC and parthenolide.

FIGS. 9 to 14 show correct diastereomers of DAHPA, IPC, strychnine, caulamidine, CPDMPPPC and parthenolide with experimental RDCs and with additional RDCs needed for SVD-based analysis.

FIGS. 19 to 24 are shown for comparison of experimentally observed RDCs with RDCs predicted by molecular simulation for different diastereomers. For each small molecule (DAHPA, IPC, strychnine, caulamidine, CPDMPPPC and parthenolide) the structure of the correct diastereomer together with the experimental RDCs is shown. The correlation between RDCs predicted by P3D ($D^{calc}$) according to the present invention for the correct diastereomer of each molecule and the experimental values ($D^{exp}$) is displayed next to the structure. Pearson correlation coefficients obtained by linear fitting of the $D^{exp}$ vs $D^{calc}$ representations for different diastereomers are shown inside the correlation plot. In a separate plot, R values obtained from P3D simulations are shown in red, while Pearson correlation coefficients obtained through best-fitting experimental RDCs to different diastereomers are shown in black (SVD). Correct diastereomers are labeled with *. The error bars are calculated from the standard deviation of 100 repetitions including noise in the RDCs (6.5 Hz for caulamidine, strychnine and parthenolide; the noise applied to the RDCs of the other compounds was taken from the errors shown in the respective publications).

Figure 15:
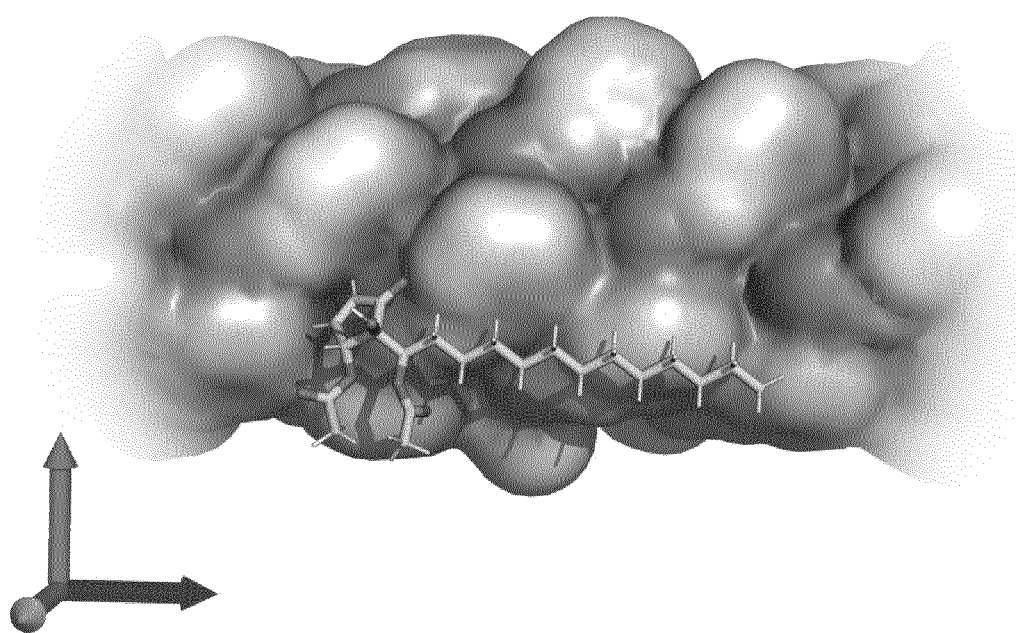

For DAHPA, for example, FIG. 15 shows a visualization of the alignment of the hygrophorone DAHPA in the anisotropic environment of a PBLG particle. The visualization is obtained by molecular simulation predicting the PBLG-induced alignment of a natural product. The orientation predicted by the method according to the present invention P3D which is implemented into the computer program "PALES" for DAHPA is shown in the frame of the diagonalized alignment tensor ($S_{zz}$-, $S_{yy}$-, and $S_{xx}$-axis shown in black, green and red, respectively). The $S_{zz}$-axis is parallel to the main axis of PBLG, which is oriented along the magnetic field.

Figure 16:
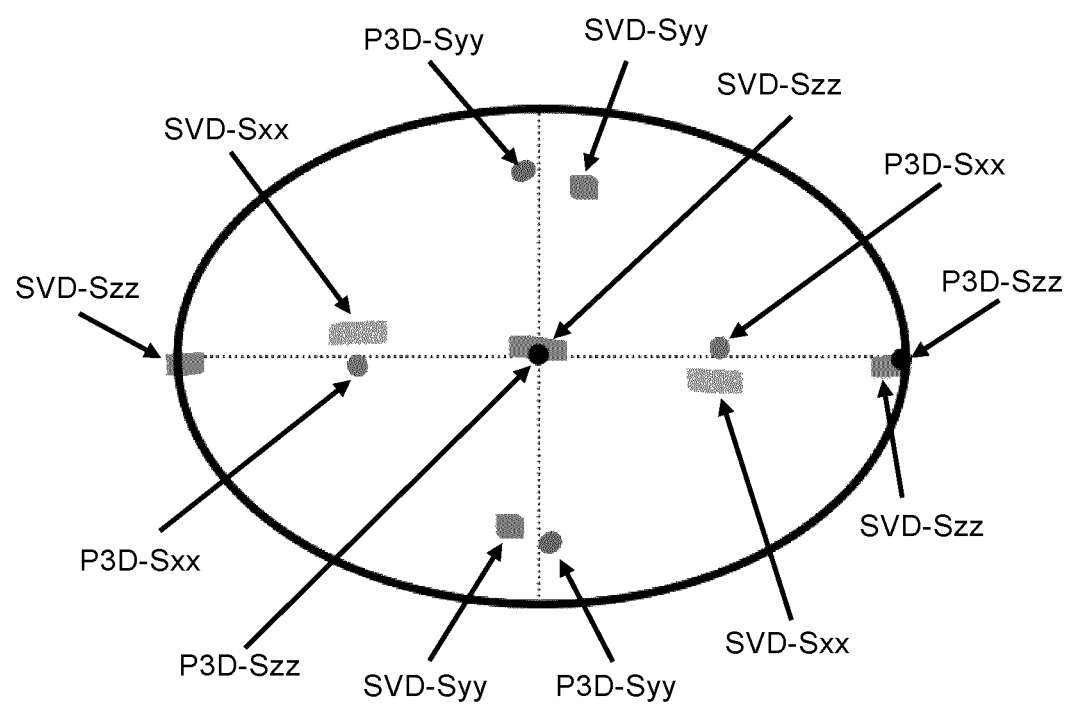
Figure 17:
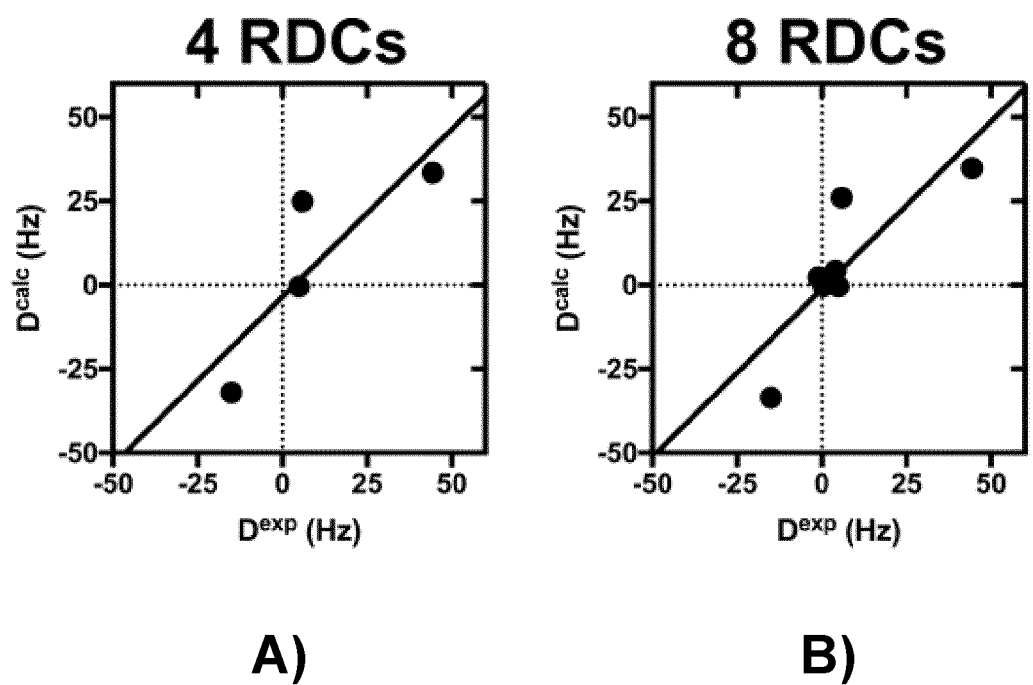
Figure 18:
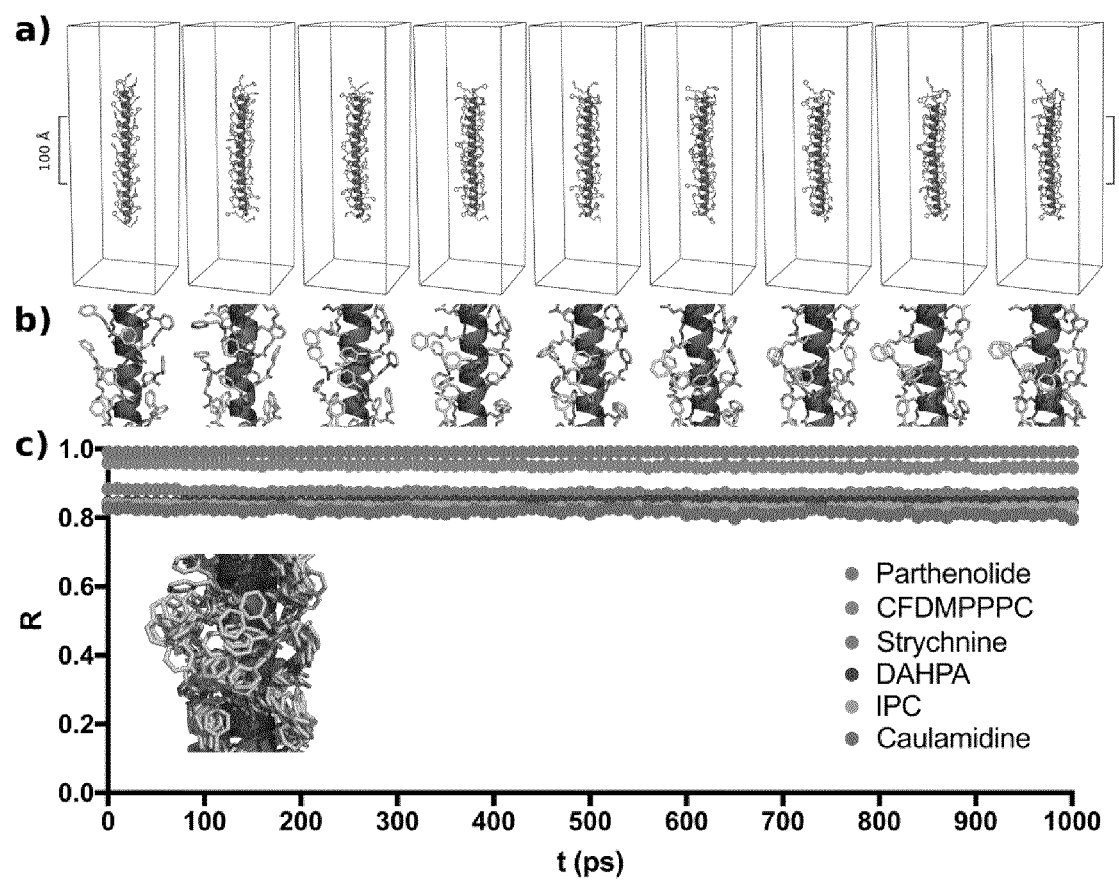
Figure 19:
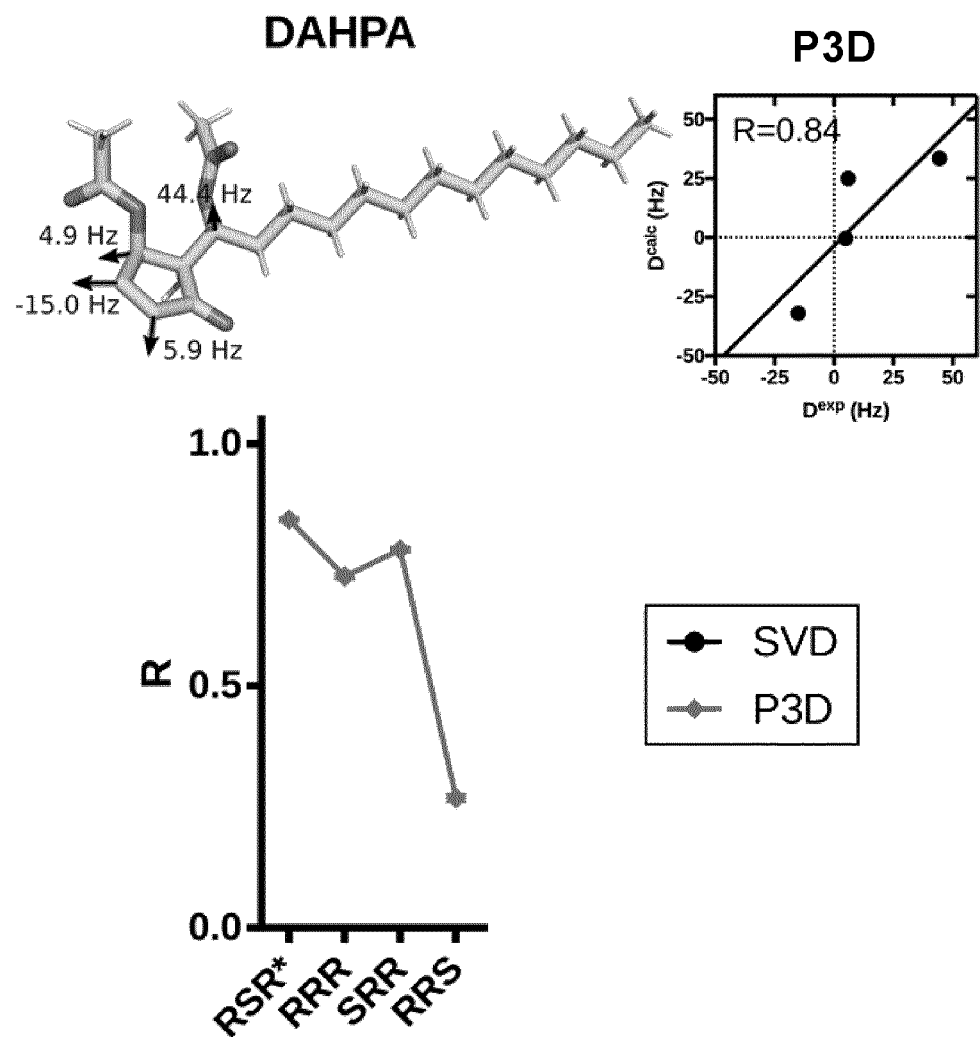
Figure 20:
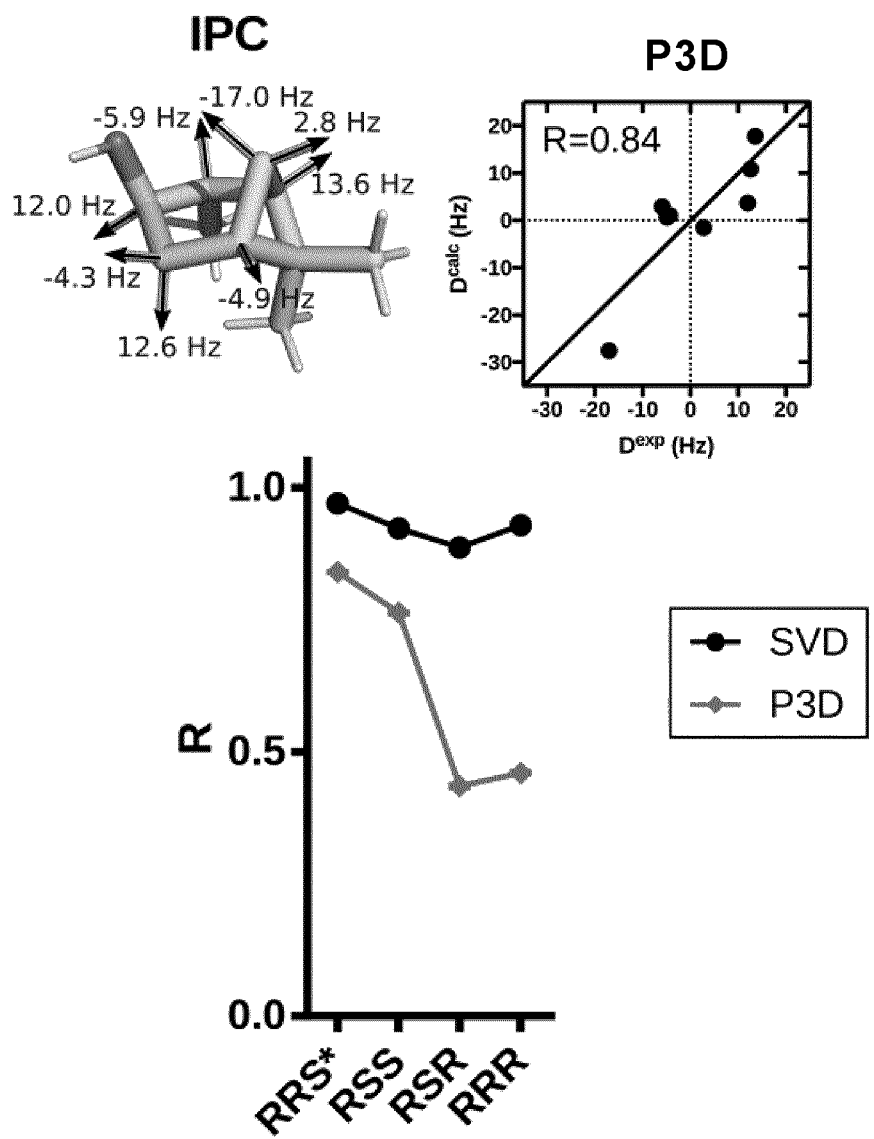

FIG. 16 shows a comparison of the orientation of the alignment tensor of DAHPA predicted by P3D (black, green, red) with the orientation derived by SVD (grey, olive, orange) from the experimental RDCs (one-bond and long-range CH RDCs were used for SVD). The orientation of the three axes corresponding to the eigenvalues $S_{zz}$, $S_{yy}$ and $S_{xx}$ of the diagonalized alignment tensor are projected onto a two-dimensional world map. In the case of the P3D predicted alignment tensor according to the pre-sent invention, the spread was derived from the 1 ns molecular dynamics simulation of PBLG (see FIG. 18). The accuracy of the SVD-derived alignment tensor orientations was estimated using a Monte Carlo noise method, in which random noise was added to the experimental RDCs according to their estimated accuracy followed by repeated SVD calculations.

Figure 25:
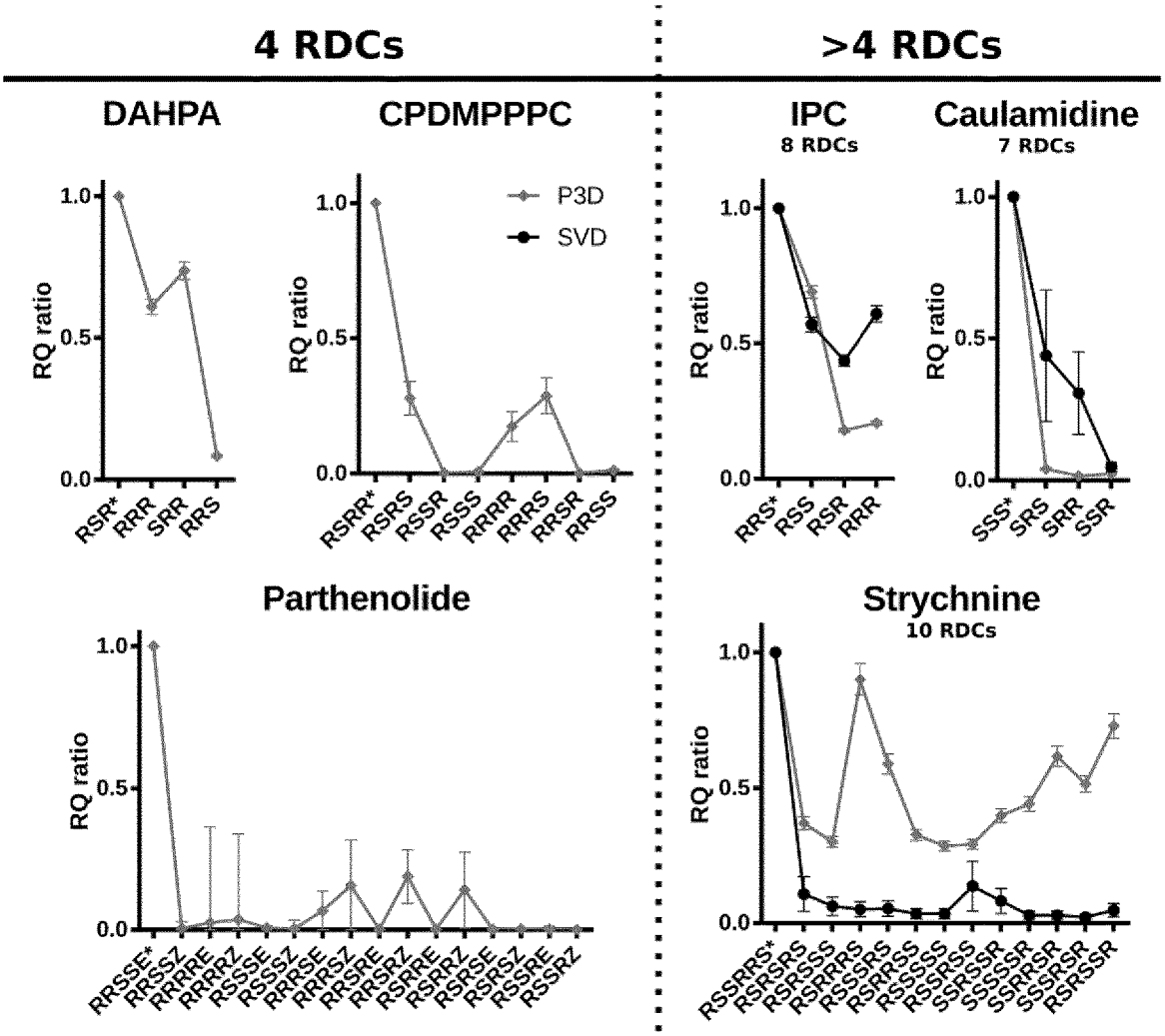

FIG. 25 represents an unequivocal structure elucidation of small molecules. RQ ratios were calculated as the ratio between the RQ value of each diastereomer and the RQ value of the correct structure. Correct diastereomers are labeled with *. RQ ratios for P3D according to the present invention are shown in red and for SVD-based analysis in black. Error bars are calculated as the propagation of the R and Qs errors (Table in FIG. 33*a*)-*c*)).

Figure 26:
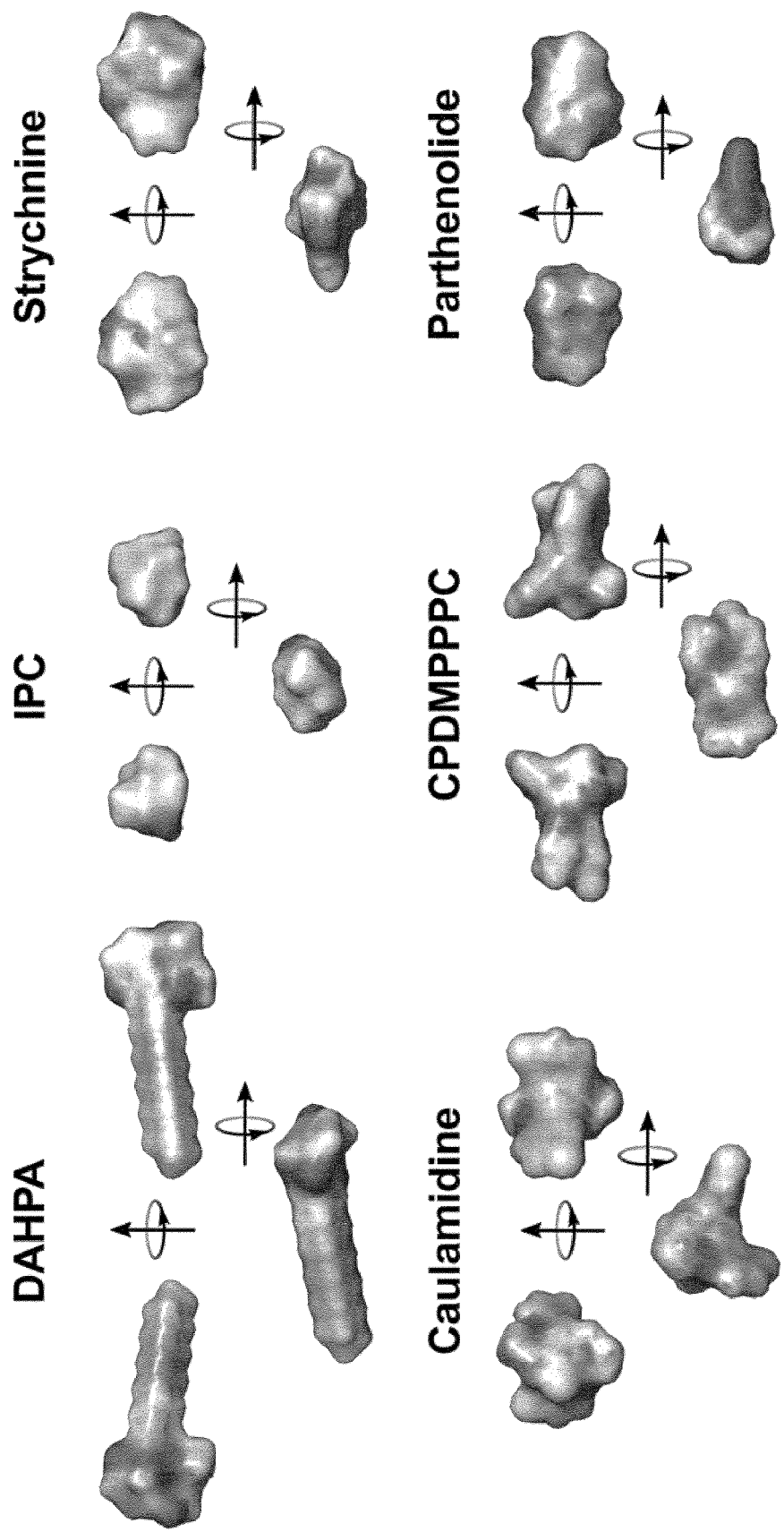
Figure 27:
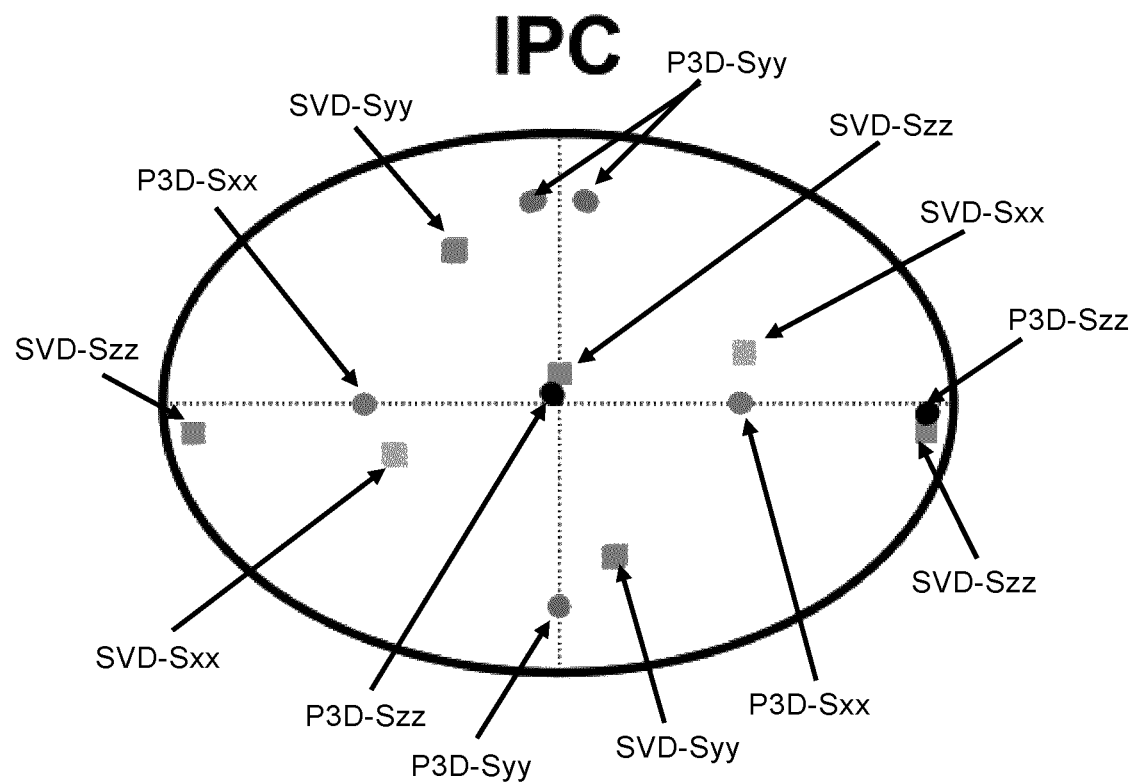
Figure 28:
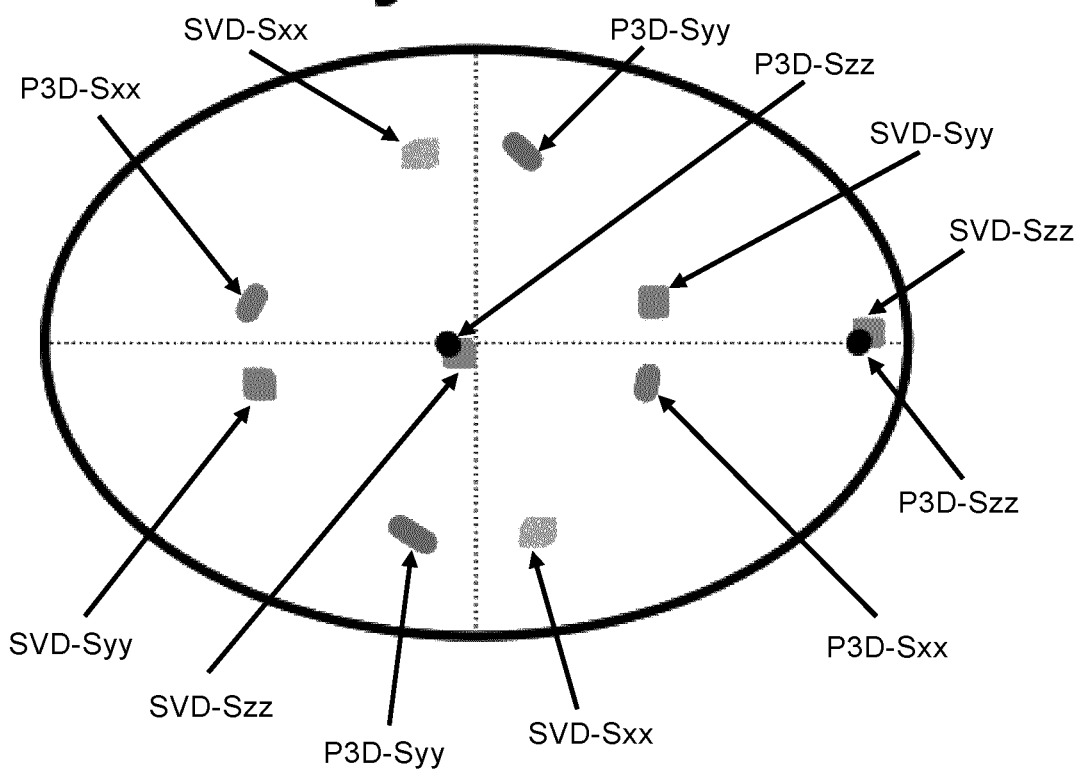
Figure 29:
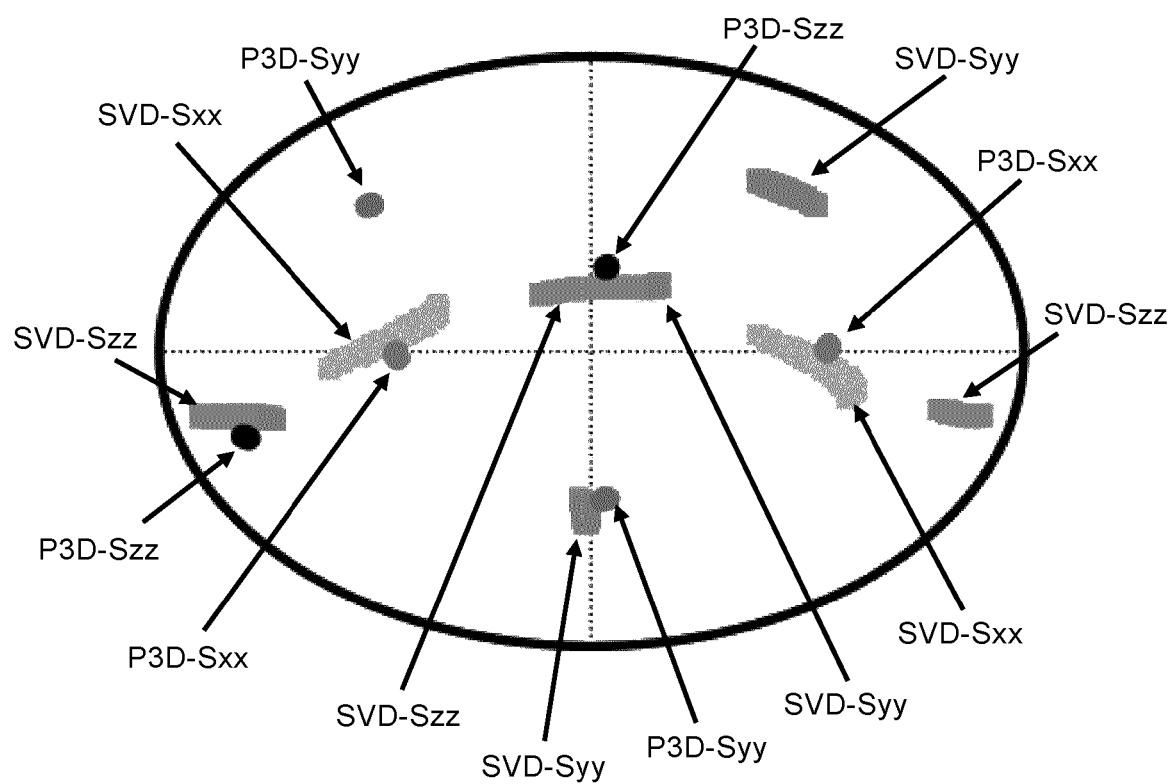
Figure 30:
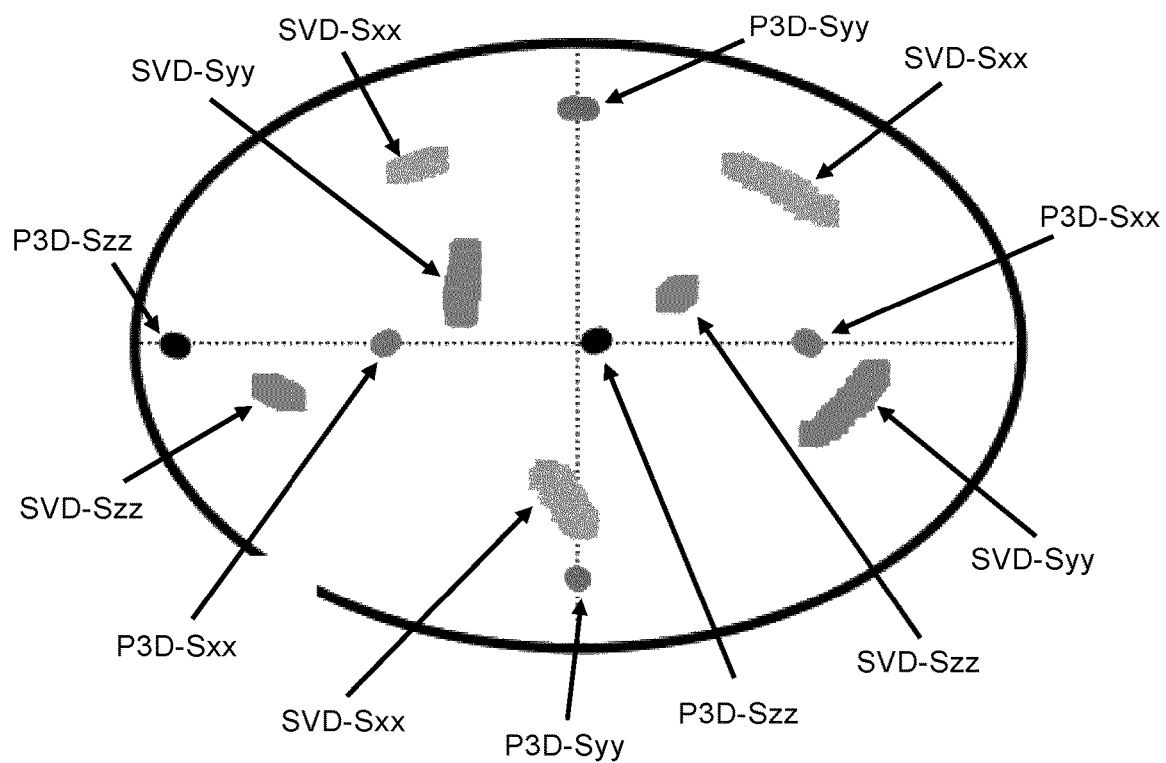
Figure 31:
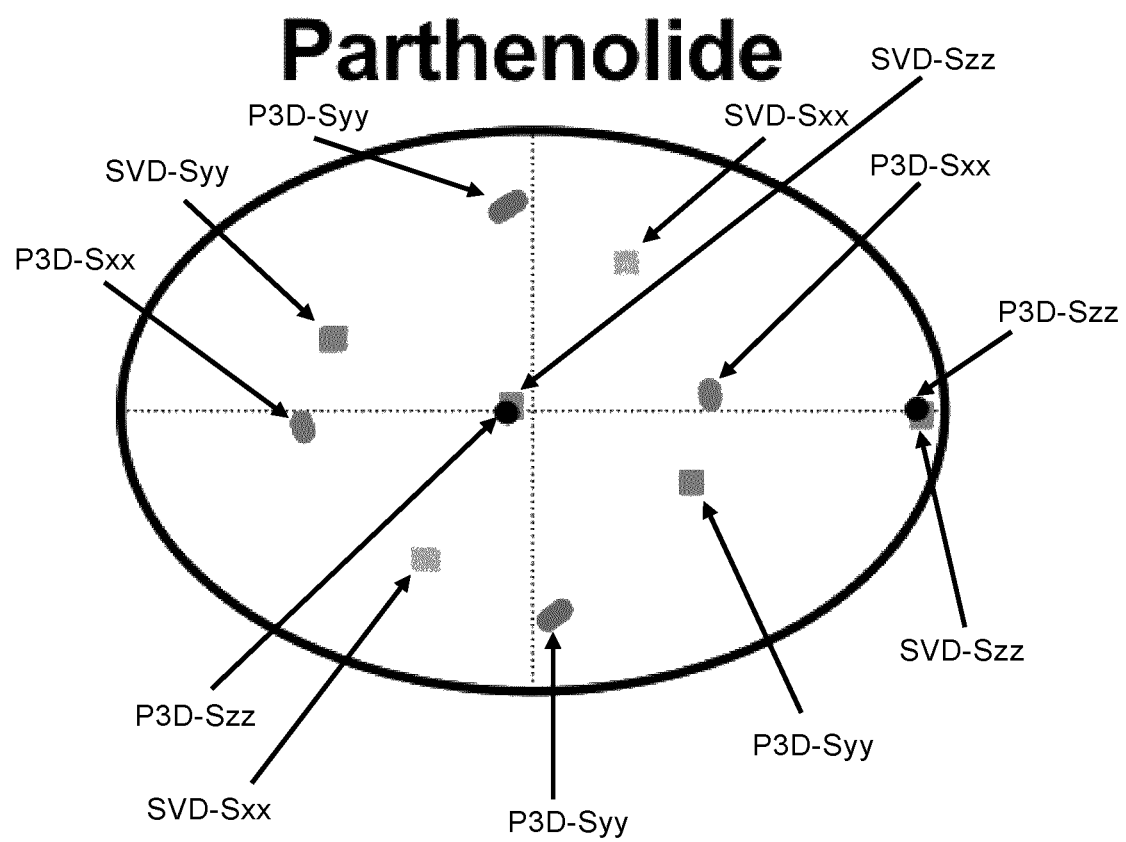

FIG. 26 shows a shape representation of the distribution of partial charges in DAHPA, IPC, strychnine, CPDMPPPC, caulamidine and parthenolide. The molecular properties of small molecules are analyzed by alignment simulations. Three different orientations are shown to illustrate differences in the shape and polarization of the six molecules.

FIGS. 27 to 31 show visualizations of the orientations of the alignment tensors predicted by the present invention (P3D) for the correct diastereomers of the small molecules IPC, strychnine, caulamidine, CPDMPPPC and parthenolide with those derived by prior art (SVD). When less than five one-bond CH RDCs were available, the complete set of RDCs were used for SVD. In the case of strychnine, CPDMPPPC and parthenolide, the SVD-derived orientation of the $S_{yy}$-axis according to the prior art was closer to the P3D-derived orientation of the $S_{xx}$-axis according to the present invention and vice versa. This is related to the definition of the parameters of the alignment tensor, i.e. the largest eigenvalue is labelled as $S_{zz}$, followed by the second largest eigenvalue $S_{yy}$, and then $S_{xx}$. When $S_{yy}$ and $S_{xx}$ have similar magnitude, inaccuracies in RDCs or alignment simulation can result in a "swap" of the $S_{yy}$- and $S_{xx}$-axis, which however has only a small influence on the back-calculation of RDCs from the alignment tensor.

Figure 32:
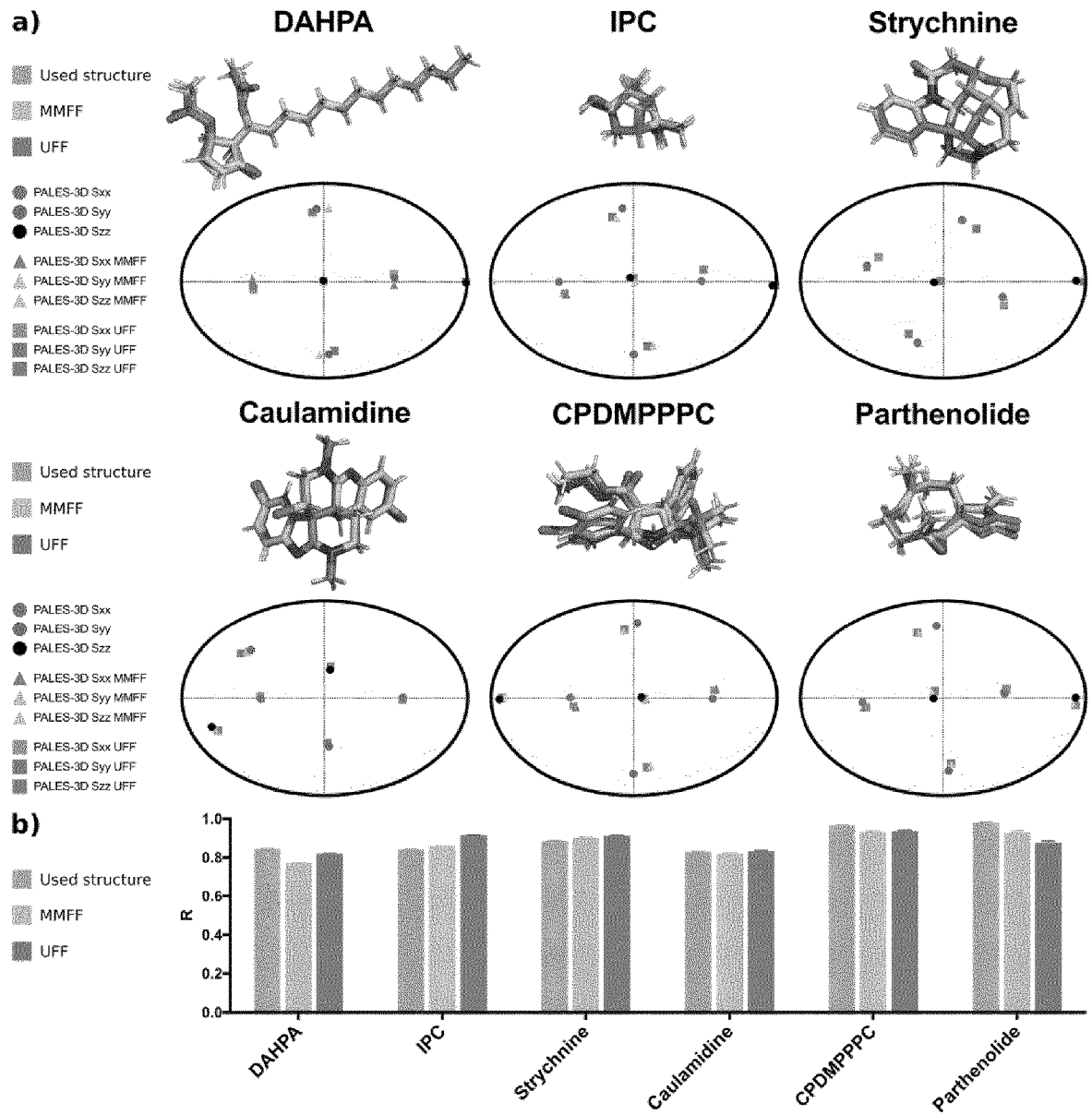

FIG. 32 shows the influence of the structures of the small molecules on alignment tensor prediction. In FIG. 32*a*, the structure of the correct diastereomer (green) of each molecule, which was used to obtain the results described above, is compared to the structures optimized with the RDKit software using two different force fields, MMFF (cyan) and UFF (magenta). Below, the orientations of the alignment tensors obtained in each case are compared. In FIG. 32*b*), $D^{exp}$ vs $D^{calc}$ Pearson correlation coefficients obtained for each molecule and structure are represented following the same colour scheme.

FIGS. 33*a*) to c) represent tables of the R and Qs quality parameters for different diastereomers and molecular alignment models using only CH RDCs. Correct diastereomers are labeled with a star (*).

It has been shown that NMR spectroscopy provides detailed insights into the constitution and configuration of small molecules and natural products, even if they do not crystallize. In contrast, the structural analysis of small molecules by X-ray and micro-electron diffraction strictly depends on the ability of crystallization. A challenge for NMR-based structural elucidation of organic molecules is, however, the presence of several stereogenic units of unknown relative and absolute configuration and the structural complexity that arises from them. To improve NMR-based structure elucidation of organic molecules, anisotropy-based NMR parameters were introduced and a wide range of alignment media compatible with organic solvents have been developed. Disruption of the isotropic motion of a small molecule by an alignment medium provides access to RDCs. However, the connection between the atomic structure of the alignment medium, the configuration of a small molecule and its RDCs has remained enigmatic.

The developed three-dimensional molecular alignment model uses the atomic structures of both the alignment medium and the solute, and calculates molecular interaction energies between the alignment particle and the small molecule based on continuum electrostatics. Comparison with the experimental NMR data of six small molecules showed that the alignment model predicts RDCs of small molecules aligned by PBLG in chloroform with good accuracy. Despite very different chemical structures, the Pearson correlation coefficient between the predicted and experimental RDCs exceeds 0.82 for the correct diastereomer of all six molecules and reaches 0.99 for parthenolide. Because the experimental RDCs of all six molecules are of high accuracy, the data suggest that additional interactions might be at work that contribute to residual deviations between experimental RDCs (and SVD-derived alignment tensors) and the RDCs predicted by the three-dimensional alignment simulation. In addition, inaccuracies in the electrostatic potential calculated for the PBLG particle and the charges assigned to the small molecules might contribute to the observed residual deviation. When considering the complexity of the problem, however, the high quality of the prediction achieved by the developed molecular alignment model is re-markable.

A key application of the ability to predict RDCs from the atomic structures of the small molecule and the alignment particle is to evaluate different structural propositions based for example on molecular mechanics-based conformer search. Analysis of a large number of different diastereomers for the six molecules showed that the developed alignment model reliably and unequivocally identifies the correct diastereomer. The most striking application is probably parthenolide, in which four CH RDCs were sufficient to select the correct diastereomer from 16 possible conformers. Indeed, for three out of the six analyzed molecules (parthenolide, DAHPA, CPDMPPPC) only four one-bond CH RDCs were experimentally available, excluding determination of the their correct diastereomer on the basis of these RDCs by mathematical minimization/SVD. The analysis of caulamidine further showed that when the number of RDCs approaches five, i.e. the number of independent elements of the alignment tensor, the variation in SVD-derived RDC parameters increases due to errors in the experimental RDCs and can therefore make SVD-based distinction of different diastereomers less reliable.

The present invention can be evaluated with a three-dimensional alignment model of PBLG, because PBLG has a well-defined, rigid conformation. However, a number of observations suggest that the same approach might be applicable to other solvents and alignment media, provided that appropriate structural models of these alignment media can be built. The first of these observations is that van der Waals interactions play an important role for the alignment of small molecules aligned by PBLG in chloroform, and thus might be equally important for other alignment media in organic sol-vents. The second observation is that the structural dynamics of PBLG had only little influence on the quality of the molecular alignment simulation. Thus, inaccuracies in the structural model and dynamics of the alignment medium might not preclude molecular alignment simulation. Molecular alignment simulations might in the future also enable the determination of the absolute configuration of small molecules via RDCs. This will require two further important developments. First, the design of alignment media, which have a well-defined molecular structure amenable to structural modeling and, secondly, induce strongly divergent alignment for different enantiomers. PBLG fulfills the first requirement, but the discriminative power of PBLG for different enantiomers on the basis of RDCs is limited. An additional requirement is the inclusion of specific interactions, such as salt bridges, into the molecular alignment simulation, as well as the consideration of both thermodynamic and kinetic contributions. Indeed, this step is tightly connected to the challenge of predicting stereoselective affinity of small molecule-binding to proteins.

In summary, a quantitative connection between the atomic structure of an alignment medium is established, the molecular structure of small molecules and anisotropy-based NMR parameters, and showed that this enables the unequivocal and reliable determination of complex molecular structures from extremely sparse NMR data.

The evaluation described above for the exemplary embodiments had been achieved as follows:

NMR Spectroscopy:

Parthenolide was prepared as described previously. To achieve an anisotropic environment, 20.5 mg of PBLG were added to a 170 μL $CDCl_3$ solution of parthenolide containing 3.5 mg of the sample. The sample was thoroughly mixed by vortexing (inverting the sample tube each time) to ensure a homogenous anisotropic solution. Coupling constants were recorded using two-dimensional $^{13}C$ J-resolved NMR experiments, acquired on a Bruker Avance III 500 MHz spectrometer equipped with a 5 mm TCI CryoProbe™ Prodigy. RDC values were measured as the difference between anisotropic and isotropic coupling constants.

Conformer Search and Geometry Optimization:

Conformer search for parthenolide was performed with the Maestro Schrödinger package using its OPLS3e force field implementation, which provides accurate geometries and adequate treatment of numerous functional groups and better represents lone electron pairs and charge distributions of drug-like molecules. Structures were kept in an energy window of 21 kJ/mol.

In the case of caulamidine, an in-house implementation of three conformer generation tools (ET, an in-house variant of distance geometry and OpenEye's OMEGA) was used. For each molecule, the maximum number of generated conformations was set to 3000. All generated conformers were then clustered, after initial MMFF94 energy minimization, based on rms of all atoms of 0.6 Å after superposition. Following a set of selection rules of the prior art representative conformers were selected from the clusters. The conformers generated for caulamidine were subsequently re-optimized at a B3LYP/6-31G level that uses the density functional theory—Hartree-Fock (HF) hybrid functional of B3LYP (Becke, three-parameter, Lee-Yang-Parr) and a split-valence double-zeta basis set 6-31G, in which the core orbital is described by a single-basis function consisting of six Gaussian-type orbitals (GTOs) and each valence orbital is described by two basis functions (double-zeta)—one consisting of three GTOs, the other of one GTO. The two asterisks in the basis set, sometimes also written as (d,p), indicate adding d polarization to non-hydrogen atoms and p polarization to hydrogens. Similarly, the con-formers generated for parthenolide were re-optimized at M062X/6-31+G level of theory, which uses the hybrid functional of Truhlar and Zhao with the split-valence double-zeta basis set but in this case including a diffuse function "+" (6-31+G). Strychnine structures were built.

For DAHPA, IPC and CPDMPPPC, the structures were generated using the CORINA algorithm, which combines monocentric fragments with standard bond lengths and angles. It handles rings and flexible chains separately in order to get an allowed set of torsion angles and minimize non-bonded interactions between flexible chain portions.

For the additional structures shown in FIG. 32, the RDKit software was used together with the force fields MMFF and UFF.

Molecular Alignment Simulation:

Prior to molecular alignment simulation, the structure of the PBLG particle was energy minimized and equilibrated in a chloroform box using GROMACS. The chloro-form solvent box was obtained from the list of equilibrated liquids validated for use with GROMACS and the OPLS/AA force field at virtualchemistry.org.

The potential file of the PBLG particle was obtained through the Adaptive Poisson-Boltzmann Solver (APBS) using the solvent dielectric constant of chloroform (4.8). Charges of the small molecules, for which RDCs were simulated, were calculated using AtomicChargeCalculator server via the electronegativity equalization method based on a common charge calculation scheme (atoms-in-molecules) and a robust quantum mechanical approach (HF/6-311G).

The three-dimensional molecular alignment simulation is based on a computationally fast method for deriving a molecular alignment tensor $A^{mol}$, which describes the average orientation of the solute molecule with respect to the magnetic field: the solute molecule is moved in steps on a three-dimensional grid that covers the central part of PBLG. At each step, an uniform distribution of different solute molecule orientations is sampled. This sampling is achieved in a two-step process. First, the z-axis of so-lute molecule samples points, which were determined by a double cubic lattice method, on a unit sphere. This sampling is highly uniform with the remaining deviation from completely uniform sampling corresponding to a residual alignment that is smaller than $10^{-7}$. With typical experimental alignment strength of ~$10^{-3}$ this introduces negligible errors into the calculations. In a second step, the molecule is rotated around the z-axis in steps of 20°. For each orientation, the simulation evaluates whether the distance between any atom of the solute molecule and any atom of the PBLG particle is smaller than the sum of the two van der Waals radii. If this is not the case, an alignment matrix A is calculated according to $A_{ij} = ½ (3 \cos \theta_i \cos \theta_j - \delta_{ij})$, where $\theta_i$ indicates the angle between the $i^{th}$ molecular axis and the z-axis (magnetic field direction) and $\delta_{ij}$ the Kronecker delta. In addition, the interaction energy between the solute molecule and the PBLG particle is calculated for each orientation/grid position on the basis of the precomputed potential file of the PBLG particle and the charges of the solute molecule. The interaction energy is converted into a Boltzmann weighing factor, which is multiplied to the alignment matrix A. All rescaled alignment matrices are added together to obtain the molecular alignment tensor $A^{mol}$. The imperfect alignment of PBLG is taken into account by multiplication of $A^{mol}$ with the fac-tor 0.8. In the final step, RDCs are calculated from $A^{mol}$ and compared to experimental values. The three-dimensional alignment model was implemented into the dipolar coupling analysis software PALES using the C++ programming language.

The convergence of the alignment simulation was tested with respect to the spacing of the three-dimensional grid along which the geometric center of the molecule is moved. Increasing the spacing between grid points from 0.2 to 1.6 Å changed the orientation of the alignment tensor predicted for strychnine by 11.74° so we selected a spacing of 0.4 Å, with only 1.26° difference. Similarly, sampling 500 instead of 100 orientations on the unit sphere and simultaneously increasing the sampling in the third dimension from 18 to 36, i.e., sampling a total of 18,000 instead of 1,800 orientations, changed the orientation of the alignment tensor predicted for strychnine by 0.61°. Therefore, for all results presented in this study, 1,800 orientations were used.

Molecular Dynamics Simulation:

Before the MD simulation, the PBLG model, prepared as described in the previous section, was equilibrated with 50,000 steps of initial energy minimization. To further equilibrate the system, 100 ps each of volume (NVT) and pressure (NPT) equilibration was performed. The MD simulation was carried out in a chloroform box using GROMACS (version 2018.2) along with the OPLS/AA force field at 300 K of temperature, 1 bar of pressure and with a coupling time (ζT) of 0.1 ps. The particle mesh Ewald algorithm was used for calculation of the electrostatic term, with a radius of 16 Å for the grid-spacing and Fast Fourier Transform. The cut-off algorithm was applied for the non-coulombic potential with a radius of 10 Å and LINCS algorithm was used to contain bonds and angles while carrying out the MD simulation. The simulation was performed during 1 ns in 2 fs steps and saving the coordinates of the system every 10 ps.

SVD of Experimental RDCs:

Experimental RDCs were best-fitted to the structures of the small molecules using SVD. Variations in the SVD-derived quality measures R and RQ were evaluated using a Monte Carlo noise method, in which random noise was added to the experimental RDCs according to their estimated accuracy.

In the following the evaluation of the partial alignment of P3D and different alignment media with two different solutes is explained.

Several different alignment media for organic solvents are nowadays available. In order to evaluate the alignment properties of these media, the two most widely studied molecules in the field are selected: strychnine and isopinocampheol (IPC).

Strychnine is a reference compound for relative configuration determination because of the high number of chiral centers (six chiral centers generating 13 diastereomers). In addition, the low flexibility of strychnine minimizes contributions from different conformations. IPC is also a rigid molecule, with little overlap in the two-dimensional proton-carbon correlation spectrum and with both enantiomers available. Because of these favorable properties, IPC was used intensively for the development of alignment media with enantiodifferentiation capabilities. There is no focus on the absolute configuration problem, so that the enantiomer (−)-IPC is selected for the analysis.

Figure 34:
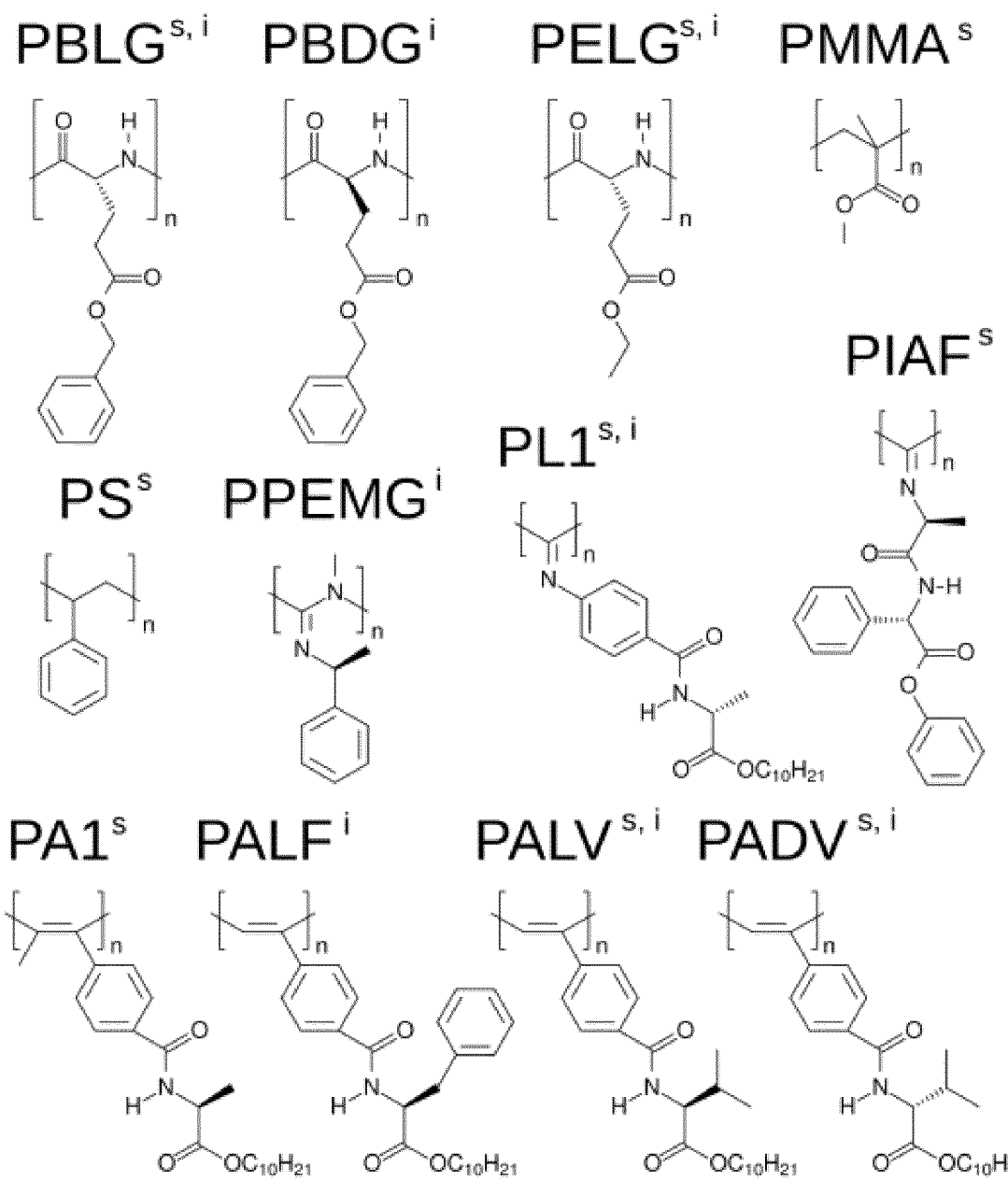

FIG. 34 represents the structures of the basic units of the anisotropic media used for the alignment of strychnine (s) and (−)-IPC (i). These are selected alignment media for which experimental RDCs of strychnine and (−)-IPC were reported.

A set of nine alignment media are extracted for each of the compounds from which five are shared.

In the following the 12 selected alignment media are listed for which experimental RDCs are available.

Alignment media for which experimental RDCs of strychnine are available are for example:
PBLG=poly(y-benzyl-L-glutamate);
PELG=poly(y-ethyl-L-glutamate);
PMMA=poly(methyl methacrylate);
PIAV=poly(L-isocyanoalanyl-L-phenylalaninie benzyl ester);
PS=Cross-linked polysterene;
PA1=Poly-A-1/L-alanine derived polyacetylene;
PL1=Poly-L-1/poly(phenylisocyanide);
PALV=L-valine derived polyacetylene;
PADV=D-valine derived polyacetylene.

Alignment media for which experimental RDCs of (−)-IPC are available are for example:
PBLG=poly(y-benzyl-L-glutamate);
PBDG=Poly(y-benzyl-D-glutamate)
PELG=poly(y-ethyl-L-glutamate);
PALF300=L-phenylalanine derived polyacetylene at 300 K;
PALV316=L-phenylalanine derived polyacetylene at 316 K;
PL1=Poly-L-1/poly(phenylisocyanide);
PALV=L-valine derived polyacetylene;
PADV=D-valine derived polyacetylene.

PPEMG=poly(N-methyl-N'—((R)-1-phenylethyl)guanidine)

From the 12 selected alignment media, ten form LLC phases. PMMA and PS were used as compressed and stretched gels, respectively. The bias towards LLC phases likely arises, because a major objective of the current development of new alignment media is on enantiodifferentiation where helical chiral nonracemic polymers, capable of forming LLC phases, are good candidates. The LLC-forming polymers include polyglutamates, polyisocyanates, polyacetylenes, polyisocyanides and polyguanidines.

Figure 35:
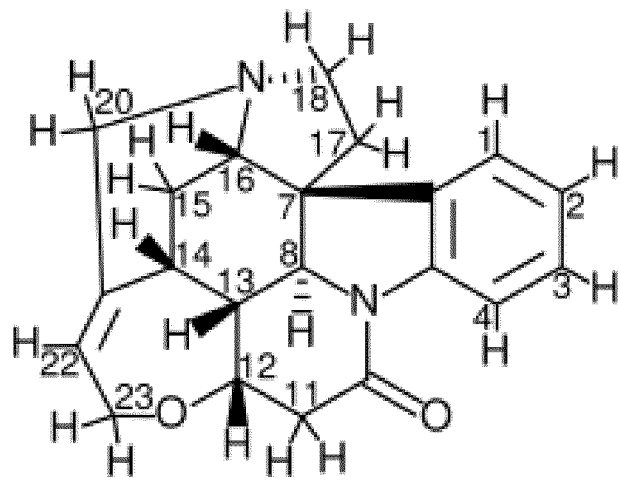
Figure 35:
Figure 36:
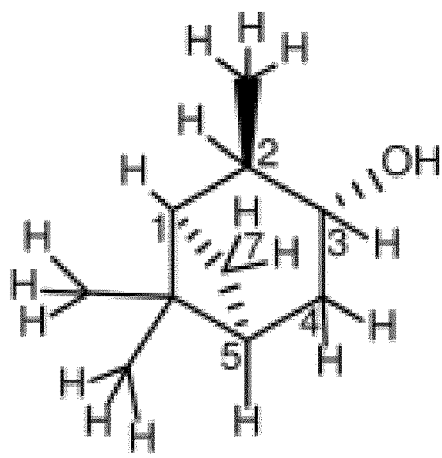

FIGS. 35 and 36 shows the strychnine and (−)-IPC structures together with the CH carbon labels and the correct configuration (top), as well as the respective lists of RDCs in the different alignment media (bottom).

The experimental one-bond CH RDCs observed for strychnine and (−)-IPC in these alignment media were compared both among each other and with the RDCs calculated by the P3D simulation using the PBLG model.

P3D simulations were performed as described above.

The alignment tensors for strychnine and (−)-IPC in the different alignment media and for the different conformers of sucrose were calculated by best-fitting experimental RDCs to the respective structures using singular value decomposition (SVD) as implemented in the software PALES. Variations in the SVD-derived quality measures R and RQ were evaluated using a Monte Carlo noise method, in which random noise was added to the experimental RDCs according to their estimated accuracy.

In the following, the RDCs and alignment comparison of different alignment media and P3D for strychnine and (−)-IPC are described.

Figure 37:
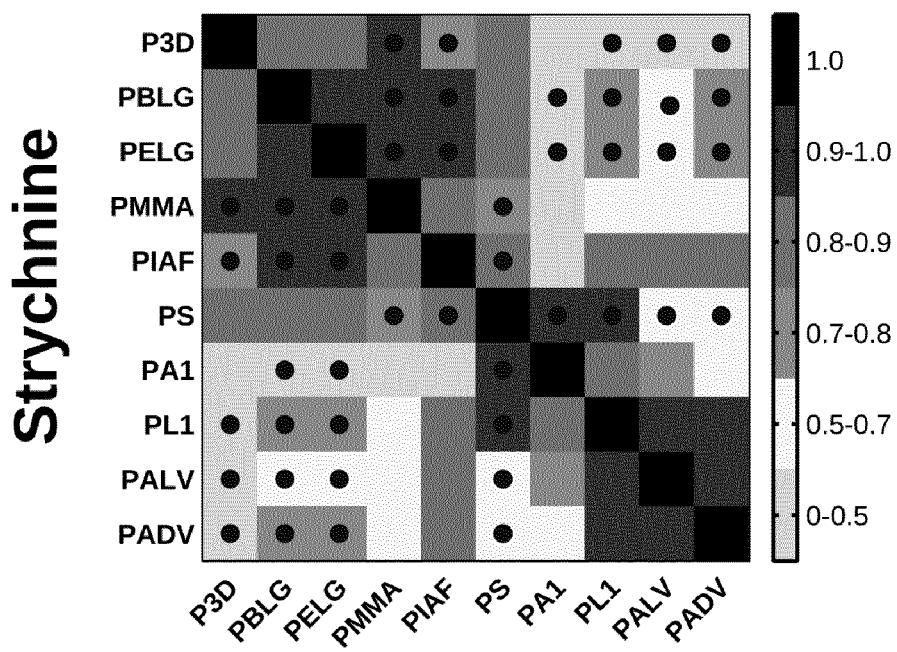
Figure 37:
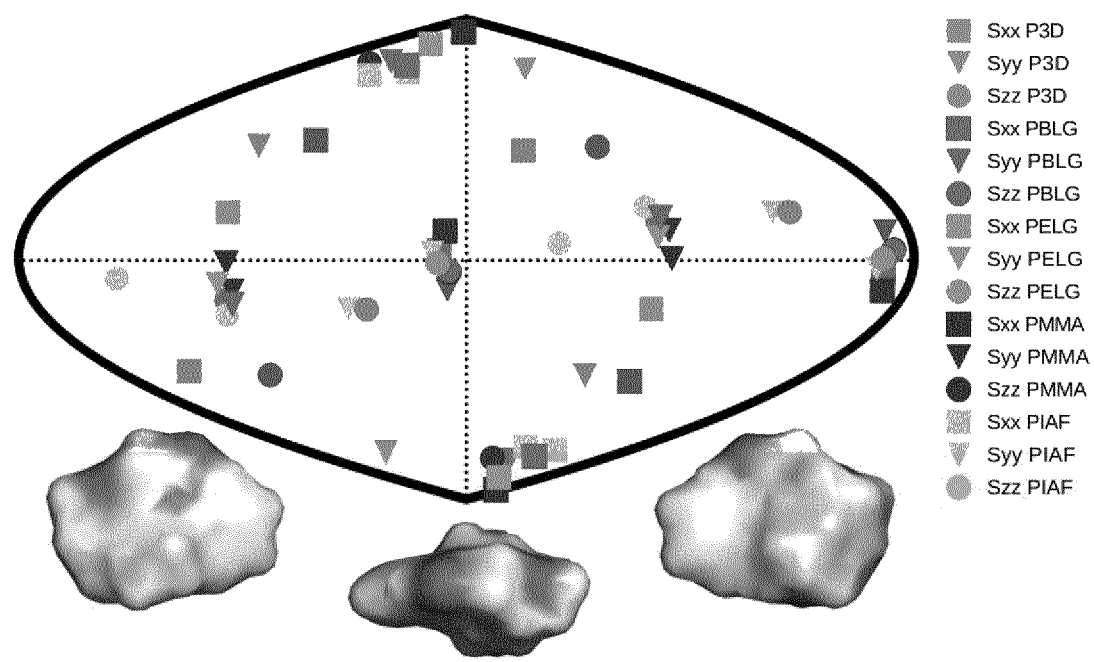

FIG. 37a) represents the matrix of the Pearson's correlation R between P3D-calculated RDCs and the experimental RDCs in different alignment media for strychnine. In the case of strychnine, half of the alignment media besides PBLG have a good correlation with the RDCs simulated by P3D on the basis of the PBLG alignment model. These alignment media are PELG, PMMA, PIAF and PS. The experimental RDCs in the second group of alignment media (PA1, PL1, PALV, PADV) also largely correlate among each other, but deviate more from the P3D-calculated RDCs.

This is confirmed by inspection of the alignment tensors shown in FIG. 37b).

FIG. 37b) shows a comparison of the orientation of the P3D-predicted alignment tensor (grey) with alignment tensors derived by SVD from experimental RDCs of the different alignment media for strychnine. The orientation of the three axes corresponding to the eigenvalues Szz (circle), Syy (triangle) and Sxx (square) of the diagonalized alignment tensor are projected onto a two-dimensional world map. Different orientations of the charged surface of strychnine are shown below.

The orientation of the z axis of the P3D-calculated alignment tensor is similar to those derived by singular-value decomposition (SVD) from the experimental RDCs in many of the alignment media, with the exception of PA1 and PL1. Notably, a smaller amount of RDCs were reported for PA1 and PL1 (five and six RDCs, respectively), which makes SVD-derived tensor orientations sensitive to the exact CH bond orientations in the employed structural models. It should be noted, that in some cases alignment tensor axes were swapped, e.g. the y-axis is positioned where in other alignment media the z axis is found as shown in FIG. 37b). This can occur when two consecutives axes/eigenvalues have similar magnitude such that inaccuracies in experimental RDCs or molecular alignment simulation result in an exchange/relabeling of these axes, which however has only little influence on the back-calculated RDCs.

Next, the same P3D-based analysis is described for (−)-IPC, which has different alignment properties when compared to strychnine.

Figure 38:
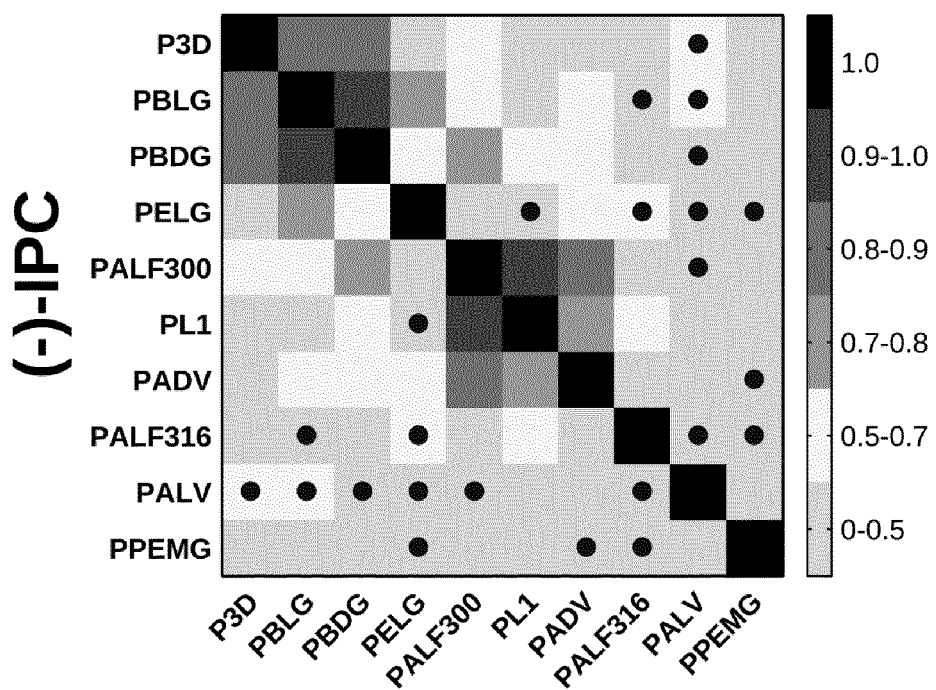
Figure 38:
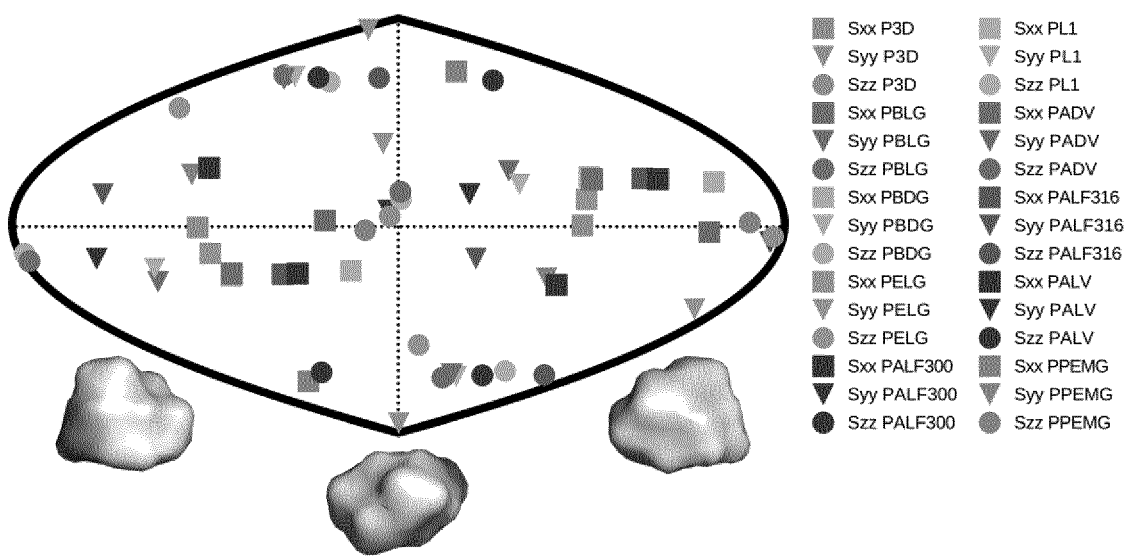

FIG. 38a) represents the matrix of the Pearson's correlation R between P3D-calculated RDCs and the experimental RDCs in different alignment media for (−)-IPC. The correlation matrix for (−)-IPC shows a strong correlation of P3D only with PBLG and PBDG. In agreement with a weaker enantiodiscrimination power of PBLG when com-pared to PELG, or the other helical chiral nonracemic polymers shown here, the experimental RDCs observed for (−)-IPC in PBLG and PELG differ.

On the other hand, PBLG and PBDG induce similar alignment such that the discrimination of different diastereomers of (−)-IPC was retained for PBDG. Notably, a change in the enantiomer of the alignment medium (e. g. from PBLG to PBDG) has the same effect as changing the enantiomer of the solute (e.g. from (−)-IPC to (+)-IPC).

FIG. 38b) shows a comparison of the orientation of the P3D-predicted alignment tensor (grey) with alignment tensors derived by SVD from experimental RDCs of the different alignment media for (−)-IPC. The orientation of the three axes corresponding to the eigenvalues Szz (circle), Syy (triangle) and Sxx (square) of the diagonalized alignment tensor are projected onto a two-dimensional world map. Different orientations of the charged surface of (−)-IPC (d) are shown below.

As far as correlations between experimental RDCs in different alignment media are concerned, only few media induce similar alignment of (−)-IPC. Only PL1, PALF300 and PADV form a small cluster in the correlation matrix. A correlation between experimental RDCs induced by PADV and PL1 was present for both (−)-IPC and strychnine with R values of 0.71 and 0.92, respectively. The pronounced differences in the alignment of (−)-IPC in different alignment media is also evident from the comparison of the respective alignment tensors: the projected axes orientations do not cluster in certain regions (FIG. 38b), in contrast to the alignment tensors of strychnine (FIG. 37b). Further notable are the RDC differences when (−)-IPC is aligned in PALF300 and PALF316 (R=0.45). This L-phenylalanine derived polyacetylene forms different LLC phases at different temperatures, with the helical structure severely disrupted at 316 K. The pronounced differences in the alignment of (−)-IPC in PALF300 and PALF316 indicates that for certain molecules/alignment media fine structural details of the alignment medium are critical for enantiodiscrimination.

In order to rationalize the distinct alignment properties of strychnine and IPC, the structural properties of the two molecules are analyzed as shown in FIGS. 37b) and 38b). While strychnine has an oval disc-like shape, the shape of IPC is quite spherical, and both molecules have asymmetric charge distributions. Comparison of the correlation coefficients of the experimental RDCs with RDCs predicted by molecular alignment simulation using P3D or only steric interactions (1D obstruction model) suggested that electrostatic interactions are more important for the alignment of strychnine: R values dropped from 0.88 to 0.64 in the case of strychnine and from 0.84 to 0.68 in the case of (−)-IPC, when replacing P3D simulations by 1D obstruction model simulations.

Figure 39:
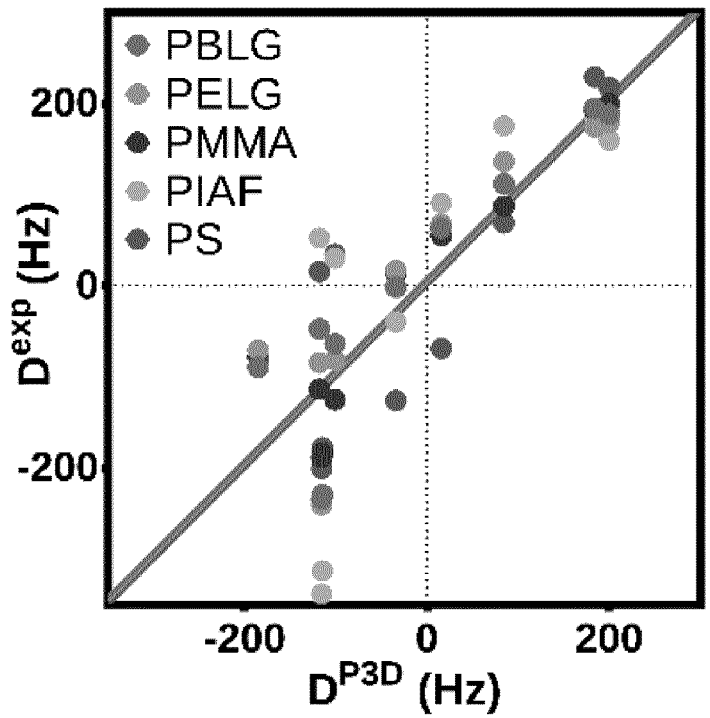
Figure 39:
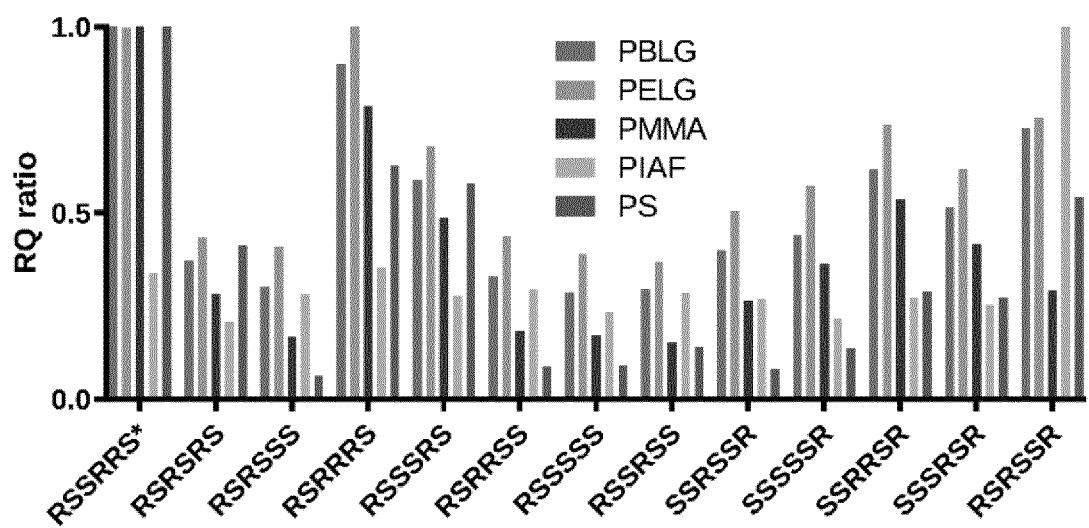
Figure 39:
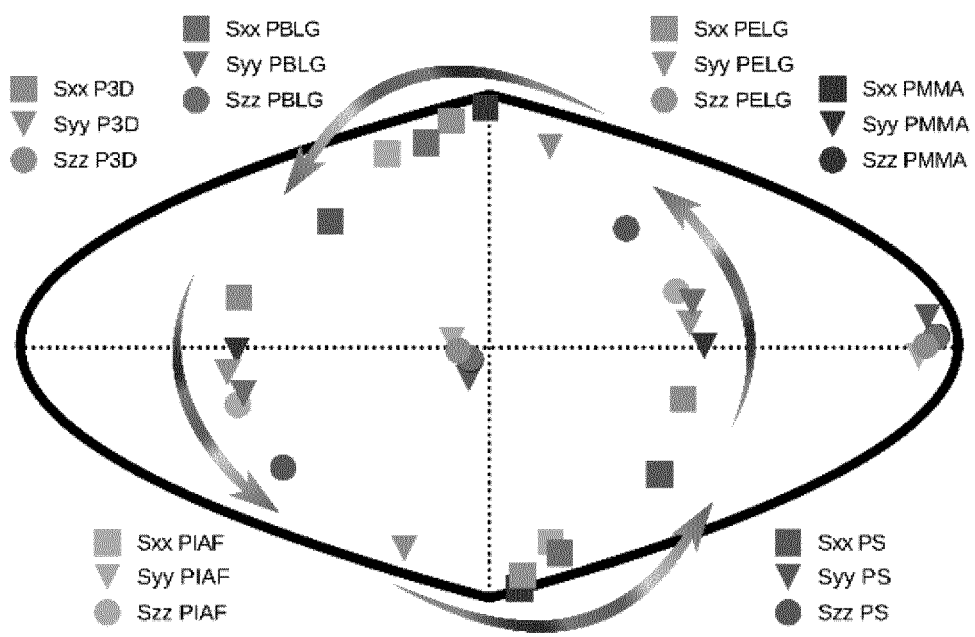
Figure 39:
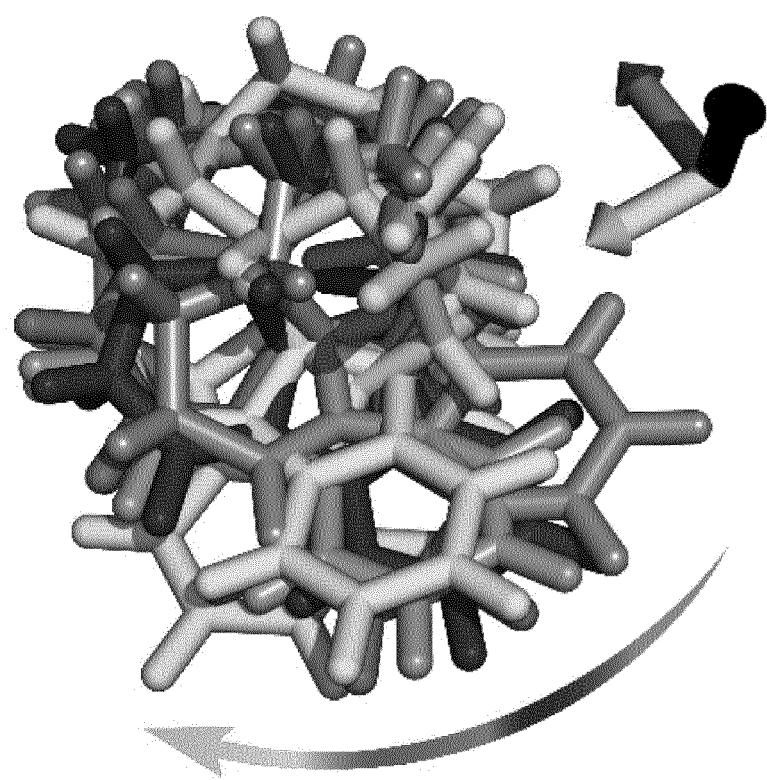

The alignment media that correlate better with the P3D prediction were further analyzed in FIG. 39a) to d).

FIG. 39a) is a diagram of the correlation between P3D-simulated RDCs)($D^{P3D}$) and experimental RDCs ($D^{exp}$)

with different alignment media for strychnine. Experimental values are normalized by the slope of the linear fitting.

FIG. 39b) is a diagram of the diastereomer discrimination power of different alignment media for strychnine based on the P3D simulation and using the RQ ratio for judging the quality of correlation. The ability of P3D-PBLG to select the correct diastereomer is retained for alignment of strychnine in PELG, PMMA and PS. This is not the case for PIAF, which has a smaller Pearson's R (0.71) when compared to PELG/PMMA/PS (all over 0.8) (FIG. 39a)). This suggests that R values larger than 0.8 are needed to identify the correct diastereomer.

FIG. 39c) represents a comparison of the orientation of the P3D-predicted alignment tensor (grey) of strychnine with alignment tensors derived by SVD from the experimental RDCs observed in different alignment media. The orientation of the three axes corresponding to the eigenvalues Szz (circle), Syy (triangle) and Sxx (square) of the diagonalized alignment tensor are projected onto a two-dimensional world map.

FIG. 39d) shows the oriented structures of strychnine according to the PBLG-based P3D simulation and the different experimentally analyzed alignment media. Axes colors are black (z), red (x) and green (y), and are rotated when the axes of the alignment tensor are swapped because of a similar magnitude of the corresponding eigenvalues. The arrows in (c) and (d) illustrate the change in the orientation of the x and y axes in different alignment media.

Comparison of P3D-predicted and experimental RDCs (FIG. 39a), as well as the alignment tensors projected onto a two-dimensional world map (FIG. 39c)) and the aligned strychnine structures (FIG. 39d)), show that the partial ordering of strychnine in these alignment media are very similar and well predicted by P3D.

Experimental RDCs observed in PMMA have a very good correlation with the P3D-calculated RDCs (FIG. 37a), 39a)) and also a very similar alignment tensor (FIG. 39c)), but the correlation is negative (FIG. 37a), dots). The negative slope indicates that the major alignment axis in PMMA is oriented orthogonal to the field, while PBLG aligns with its helix axis parallel to the magnetic field. Indeed, the PMMA gel was compressed, while the stretched PS gel displayed a positive correlation with the P3D-calculated RDCs. In other words, strychnine has in PMMA a highly similar alignment tensor as in PBLG/PS but with an opposite sign of the axial component of the alignment. For these reasons, when different alignment media are being compared, the absolute value of the Pearson's correlation coefficient R is used.

The excellent correlation between P3D-predicted and experimental RDCs of strychnine in PBLG indicates that the alignment of strychnine in PBLG is dominated by steric and electrostatic factors (FIG. 37a)+b), FIG. 38a)+b) and FIG. 39a)-c)). At the same time, the fine structural details of the alignment media appear to be less important, which results in similar alignment of strychnine in PBLG, PELG, PMMA and PS (FIG. 39a)-c)). On the other hand, the quite spherical shape of IPC suggests that steric obstruction is less important for its molecular alignment. Instead specific molecular interactions between IPC and the alignment medium become relevant and are responsible for the differences in RDC values observed in different alignment media. The difference in the alignment of IPC in PBLG and PELG might be correlated with the stronger enantiodifferentiating power of PELG, which has been linked to the change in the bulkiness and mobility of the lateral side chain. Due to these differences, IPC can have more and stronger diastereomorphous interactions with the chiral helical backbone of PELG. The importance of fine structural details for the alignment of IPC also provides a rationale for why IPC is an excellent test molecule to study the enantiodifferentiation properties of alignment media.

Analysis of Conformational Ensembles Using P3D:

Because the above tested molecules such as strychnine and IPC are rigid molecules, a single alignment tensor accurately describes their weak LLC/gel-induced alignment. However, for more flexible molecules it is necessary to determine alignment tensors for all the conformers or independently for every flexible part of the molecule. In order to simplify this problem, linearly independent alignment media would be needed, which, as shown in FIG. 37a)+b) and FIG. 38a)+b), is not always easy to achieve. When only one alignment medium is available, selection of energetically more promising structures and back-calculation of anisotropic NMR parameters to best-fit experimental values might be used. The latter approach, however, requires a large amount of anisotropic NMR parameters and becomes difficult when the alignment tensors of the conformers are different.

The described P3D alignment simulation is useful to solve the relative configuration problem. It had been demonstrated with the examples above that P3D can identify the correct diastereoisomer from a very small number of RDCs, even with less than five RDCs, the minimum number of RDCs required for SVD.

The method of P3D can also be used to address the problem of conformation. To this end, sucrose is selected as example, for which measurement data are available from analyses with anisotropic NMR in PBLG. Studies based on molecular dynamics (MD) simulations and solution NMR suggested the presence of multiple sucrose conformations. On the basis of 11 RDCs and 12 RCSAs, the conformational ensemble of sucrose in CDCl3/DMSO (70:30) was best described with three conformers, which were selected from a set of low energy DFT structures. The respective $\Delta G$ of con-formers 1, 2 and 3 were 0, 2.04 and 2.72 kcal/mol, with conformer 3 being highly similar to the crystal structure of sucrose.

In the following, the P3D-based validation of the conformational ensemble of sucrose using conformer populations determined in prior art is described.

Figure 40:
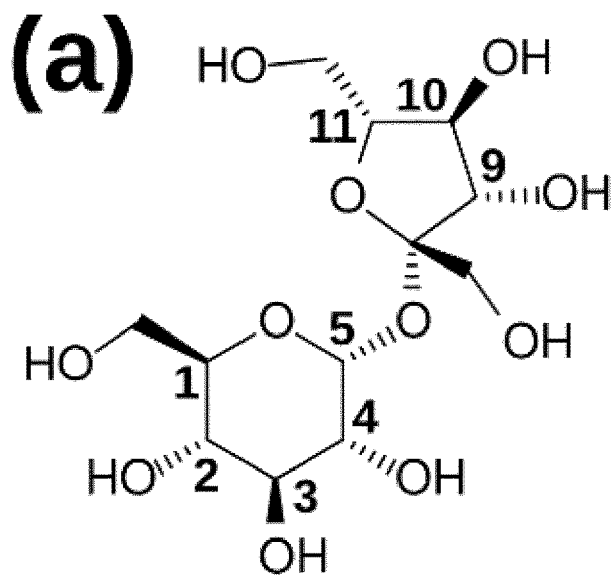
Figure 40:
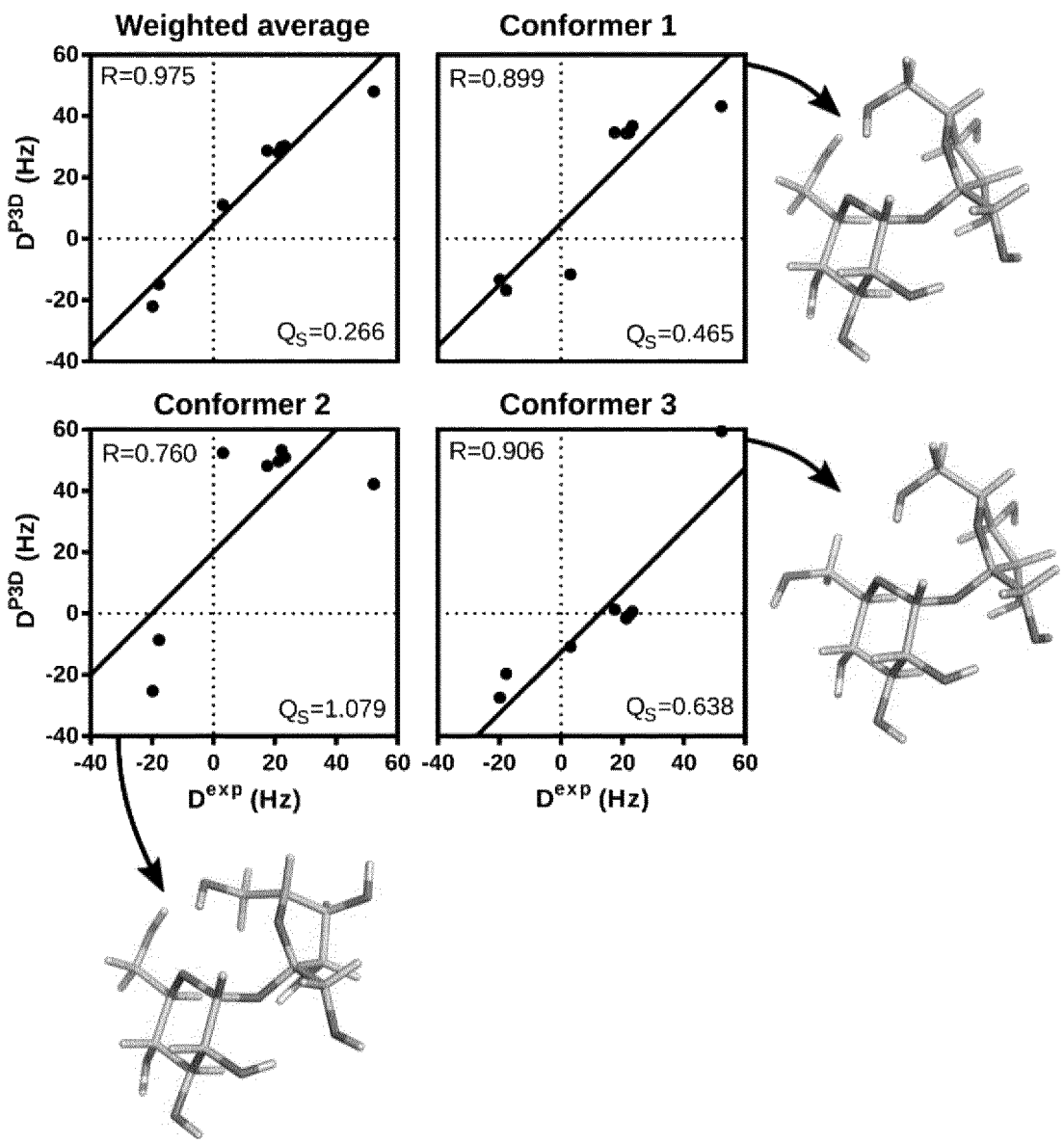
Figure 40:
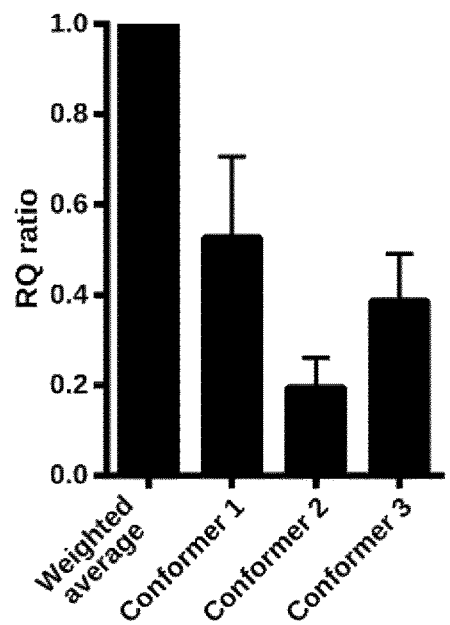
Figure 40:
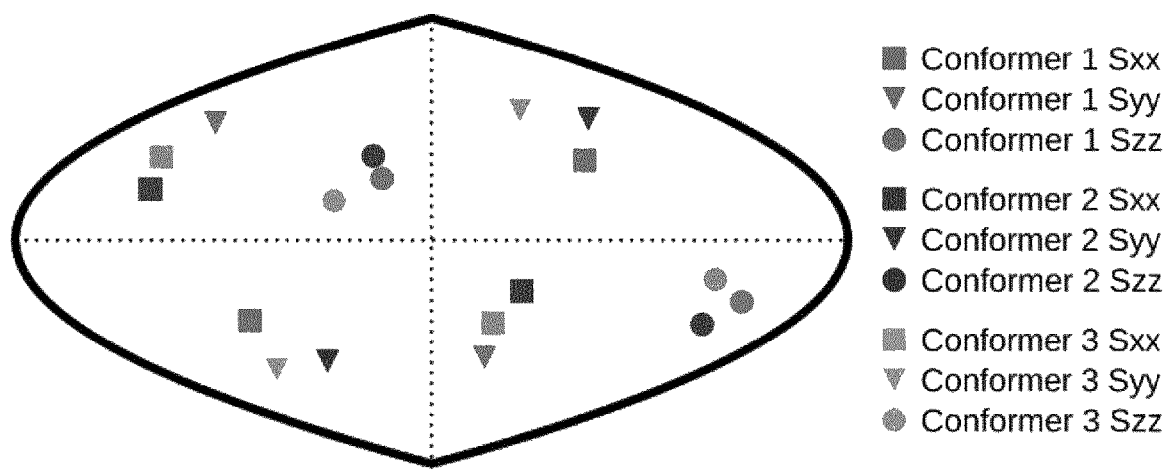

FIG. 40a) shows the sucrose structure with the CH carbons labeled.

FIG. 40b) is a list of P3D-simulated RDCs for the 3 conformers together with the average weighted RDCs and the experimental RDCs. Listed populations of the 3 conformers were determined in prior art.

FIG. 40c) shows diagrams of the correlations between the experimental RDCs ($D^{exp}$) and the P3D-simulated RDCs for the three conformers and the average de-rived through weighting according to populations determined in prior art.

FIG. 40d) shows the RQ ratios of the three different conformers in reference to the average derived through weighting according to populations determined in prior art. The error bars are calculated as the propagation of R and Qs errors and these errors are calculated from the std of 100 repetitions including noise in the RDCs.

FIG. 40e) represents a comparison of the orientation of the P3D-predicted alignment tensors for the three conformers. The orientation of the three axes corresponding to the eigenvalues Szz (circle), Syy (triangle) and Sxx (square) of the diagonalized alignment tensor are projected onto a two-dimensional world map.

Instead of the 23 anisotropic NMR parameters used in the prior art, here only the eight one-bond CH RDCs are used as shown in FIG. 40a) and b). Following the same rationale as before, the one-bond CH RDCs (FIG. 40b) are selected because they are the largest RDCs in small molecules, i.e. can be measured with high accuracy, and there is less ambiguity in the assignment. The three conformers of sucrose to P3D alignment simulation are selected. P3D-simulated RDCs were averaged over the three-member ensemble using conformer populations determined in the prior art, and compared with the experimental RDCs (FIG. 40b) and c)). The results indicate that the three-member ensemble of conformers improved the correlation reaching a R value of 0.975 (FIG. 40c)). The RQ of the weighted average is also significantly larger than the RQ values for any of the three individual conformers (FIG. 40d)).

The structures of the three conformers were aligned before the simulation in order to have the same molecular frame and be able to compare the alignment tensors (FIG. 40e)). The result shows that all the conformers have a similar but not identical alignment, indicating that the differences in RDCs come mainly from the structural differences, in agreement with the use of the variable-weight single-tensor SVD method to solve the conformational structure of the molecule.

Next, the refinement of the conformational ensemble of sucrose using P3D is explained. In order to refine the relative populations of each sucrose conformer from the P3D-predicted RDCs, RQ values were maximized by a grid search over the conformer populations using steps of 1%.

Figure 41:
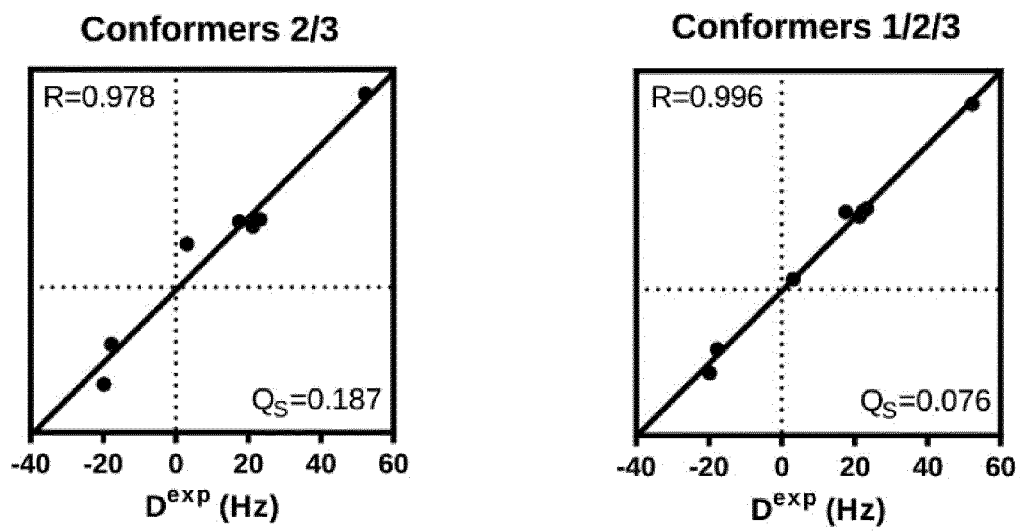
Figure 41:
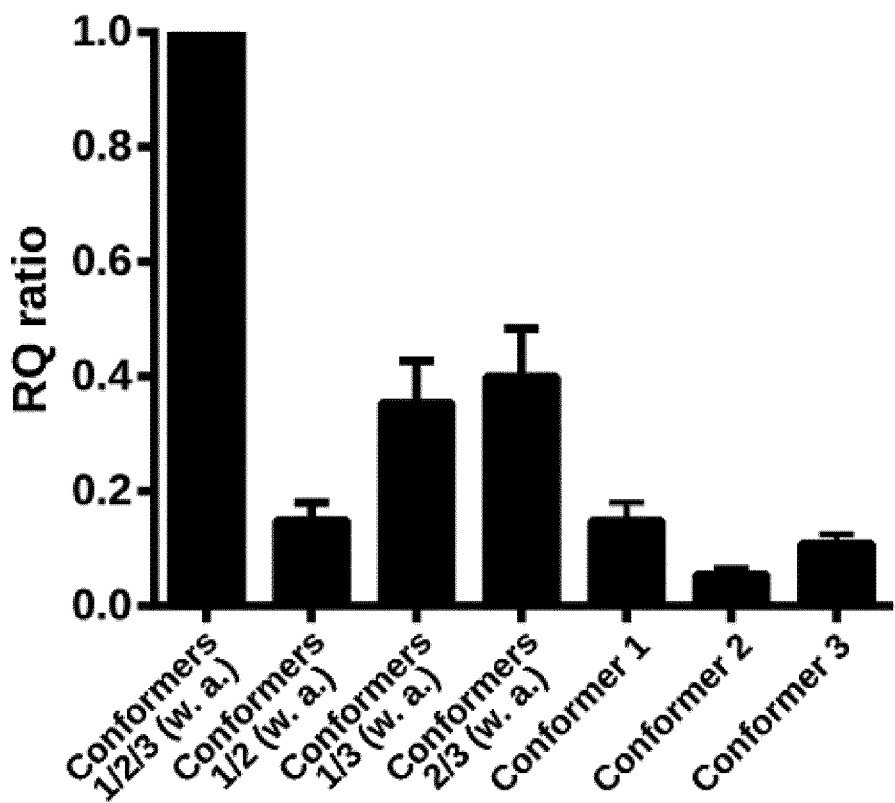

FIG. 41a) is a list of P3D-calculated RDCs for the 3 conformers together with the average weighted RDCs from the P3D-based RQ maximization for 2- and 3-conformer ensembles and the experimental RDCs.

FIG. 41b) represents diagrams of the correlation between the experimental RDCs ($D^{exp}$) and the P3D-calculated RDCs for the weighted average of the RQ maximization for 2- and 3-conformer ensembles.

FIG. 41c) shows the RQ ratios of the three different conformers in reference to their weighted average as 2- and 3-conformer ensembles. Error bars were calculated as the propagation of R and Qs errors and these errors are calculated from the std of 100 repetitions including noise in the RDCs.

While the variable-weight single-tensor SVD method strongly relies on the assumption that different conformers have similar alignment tensors, this is not required for the P3D-based conformational analysis. Therefore, the relative amounts of conform-ers by maximizing the P3D-based RQ parameter are determined (FIG. 41a) and b)). The comparison of the RQ ratios of the RQ maximized 3-conformer ensemble and the RQ maximized 2-conformer ensembles (FIG. 41c)) shows that three is the minimum number of conformers to get an almost perfect fit (R=0.996; QS=0.076). In addition, the contribution of conformer 3 was increased to 49% (compared to 32% in (Ndukwe, I. E., Wang, X., Pelczer, I., Reibarkh, M., Williamson, R. T., Liu, Y. and Martin, G. E.: PBLG as a Versatile Liquid Crystalline Medium for Anisotropic NMR Data Acquisition. Chem. Comm., 30, doi:10.1039/C9CC01130G, 2019)) in the refined 3-conformer ensemble (FIG. 41a) and b)). Notably, the most populated conformer (conformer 3) is closest to the crystal structure of sucrose.

The exemplary description above present the important role of molecular alignment simulations for the structural analysis of small molecules. The analysis supports the applicability of P3D simulations for the determination of the relative configurations, but also extends it to the analysis of conformational ensembles of small molecules. In addition, molecular alignment simulations can be used for the determination of the absolute configuration. While much progress has been made in the development of powerful chiral alignment media, this is restricted to the differentiation between enantiomers, similar to exposing small molecules to polarized light. To determine the absolute configuration, atomistic descriptions are required that link the NMR anisotropic parameters obtained from chiral alignment media with the correct enantiomer. A next step towards this goal is the inclusion of specific interactions between the solute and the alignment medium, for example salt bridges, into molecular alignment simulations.

Towards this next step, it is desired to define an alignment medium, which has a structure amenable to structural modeling and strong enantiodiscrimination capabilities. Therefore, different alignment media have been analyzed and compared them with the P3D alignment simulation model of PBLG. Two molecules, strychnine and IPC, are available for which RDCs in several different alignment media had been reported. The results of the exemplary analysis suggested that the weak alignment induced by LLC phases and gels critically depends on both the molecular properties of the alignment medium and the small molecule. The comparison further showed that the alignment of IPC varies more strongly across the available alignment media when compared to strychnine (FIG. 37a)+b) and FIG. 38a) and b)). This can be interpreted as a consequence of the more symmetrical/spherical shape of IPC such that more specific interactions with the alignment medium more strongly contribute to the alignment process. In the case of strychnine, on the other hand, steric obstruction together with electrostatic interactions dominate molecular ordering. This leads to less variability in the partial alignment of the small molecule allowing the application of the P3D-PBLG model to other alignment media (FIG. 39a)-d)). The choice of alignment medium should therefore take into account the structural properties of the small molecule of interest, especially its shape as well as the charge distribution.

Investigating the applicability of the P3D-PBLG simulation approach to the challenge of determining conformational ensembles of flexible small molecules on the example of sucrose, results in the finding, that P3D can be used to determine the populations of different conformers in an ensemble, with the advantage that it can work even when individual conformers have different alignment tensors. Through the P3D-based analysis the population of each conformer in the ensemble can be optimized.

The analysis resulted in an ensemble in which the population of conformer 3, which is closest to the crystal structure of sucrose, was increased to almost 50% (FIG. 41a)-c)). The lower population of conformer 3 in the SVD-based ensemble might arise from the slightly different alignment tensors of the three conformers (FIG. 40e)).

In summary, P3D alignment simulations establish a quantitative connection between the alignment medium, the molecular structure of small molecules and anisotropy-based NMR parameters. P3D can therefore predict RDCs for different alignment media depending on the structural details of both the alignment medium and the small molecule and thus enables the determination of conformational ensembles of flexible small molecules.

The invention claimed is:

1. A method for determination of molecular parameters for a configuration of a known single organic molecule embedded in an anisotropic environment generated by alignment media, said known single organic molecule comprising particles, comprising:

a) defining a three-dimensional grid that is aligned with a known atomic structure of an alignment medium;
b) placing the particles of the known single organic molecule on respective grid points of a three-dimensional grid in relation to at least one assigned atom of the alignment medium;
c) determining an interaction between the particles of the single organic molecule and the alignment medium for a set of orientations and a plurality of configurations of the particles; and
d) calculating anisotropic parameters, obtainable by measuring with nuclear magnetic resonance (NMR) spectroscopy, by use of the determined interactions for each of the plurality of configurations of the single organic molecule.

2. The method according to claim 1, wherein the determination of the interaction between the particles of the organic molecule and the alignment medium in step c) comprises evaluating steric effects and/or evaluating van der Waals forces and/or evaluating electrostatic forces acting between a respective organic molecule and the alignment medium.

3. The method according to claim 1, further comprising
e) comparing anisotropic parameters measured for the organic molecules embedded in the alignment medium with nuclear magnetic resonance (NMR) spectroscopy with each of the anisotropic parameters determined for each of the plurality of configurations of the organic molecule, and
f) determining a configuration of the organic molecule.

4. The method according to claim 3 wherein the step of comparing comprises calculating a quality parameter (RQ) with a term comprising the Pearson correlation coefficient (R) and a scaled quality factor, wherein the scaled quality factor is calculated with residual dipolar couplings (RDCs) scaled with a slope of the fitting (Qs), wherein the configuration related to the highest quality parameter is determined as the configuration of the organic molecule.

5. The method according to claim 4, wherein the quality parameter (RQ) is calculated by a formula $(R+1)^2/Qs$, wherein R is the Pearson correlation coefficient of a linear fitting of observed residual dipolar couplings (RDCs) measured by nuclear magnetic resonance (NMR) spectroscopy ($D^{exp}$) versus a calculated residual dipolar couplings (RDCs) obtained by simulation ($D^{calc}$), and wherein the scaled quality factor Qs is calculated by a slope of the fitting for a quality factor $Q=rms(D^{exp}-D^{calc})/rms(D^{exp})$, with rms indicating the root-mean-square.

6. The method according to claim 1 wherein the determination of the interaction in step c) comprises determining potential energies between the organic molecule and related atoms of the alignment medium by calculating a respective equation of steric obstruction and/or van der Waals interaction and/or continuum electrostatics.

7. The method according to claim 1 further comprising converting potential energies determined in step c) into probabilities for orientation of the respective organic molecule in front of a related atom of the alignment medium by use of the Boltzmann equation.

8. The method according to claim 1 further comprising placing a simulated organic molecule in step b) outside a radius defined by the van der Waals force of a related atom of the alignment medium in its three-dimensional atomic structure for determining interaction of the organic molecule and the related atom of the known alignment medium in step c).

9. The method according to claim 1 further comprising calculating alignment tensors of the organic molecule for the respective points of the three-dimensional grid by use of the probabilities for orientation.

10. The method according to claim 9 further comprising comparing of anisotropic NMR parameters calculated from alignment tensors with anisotropic NMR parameters measured by NMR spectroscopy.

11. The method according to claim 10 wherein the step of comparing comprises calculating a quality parameter (RQ) with a term comprising the Pearson correlation coefficient (R) and a scaled quality factor, wherein the scaled quality factor is calculated with residual dipolar couplings (RDCs) scaled with a slope of the fitting (Qs), wherein the configuration related to the highest quality parameter is determined as the configuration of the organic molecule.

12. The method according to claim 11, wherein the quality parameter (RQ) is calculated by a formula $(R+1)^2/Qs$, wherein R is the Pearson correlation coefficient of a linear fitting of the observed residual dipolar couplings (RDCs) measured by nuclear magnetic resonance (NMR) spectroscopy ($D^{exp}$) versus a calculated residual dipolar couplings (RDCs) obtained by simulation ($D^{calc}$), and wherein the scaled quality factor Qs is calculated by a slope of the fitting for a quality factor $Q=rms(D^{exp}-D^{calc})/rms(D^{exp})$, with rms indicating the root-mean-square.

13. A data processing apparatus comprising means for carrying out the steps of claim 1.

14. A computer program product comprising instructions for a computer program encoded on a non-transient computer readable storage medium which, when the computer program is executed by a computer, cause the computer to carry out the steps of claim 1.

15. A non-transient computer readable storage medium comprising instructions for a computer program which, when executed by a computer, cause a computer to carry out the method of claim 1.

* * * * *